(12) United States Patent
Gao et al.

(10) Patent No.: US 10,744,204 B2
(45) Date of Patent: Aug. 18, 2020

(54) CONJUGATED COMPOUNDS COMPRISING CYSTEINE-ENGINEERED ANTIBODIES

(71) Applicant: MedImmune, LLC, Gaithersburg, MD (US)

(72) Inventors: Changshou Gao, Gaithersburg, MD (US); Godfrey Rainey, Gaithersburg, MD (US); Cuihua Gao, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 36 days.

(21) Appl. No.: 15/302,036

(22) PCT Filed: Apr. 10, 2015

(86) PCT No.: PCT/US2015/025237
§ 371 (c)(1),
(2) Date: Oct. 5, 2016

(87) PCT Pub. No.: WO2015/157595
PCT Pub. Date: Oct. 15, 2015

(65) Prior Publication Data
US 2018/0169255 A1    Jun. 21, 2018

Related U.S. Application Data

(60) Provisional application No. 61/978,481, filed on Apr. 11, 2014.

(51) Int. Cl.
| | |
|---|---|
| *A61K 39/00* | (2006.01) |
| *A61K 47/68* | (2017.01) |
| *C07K 16/00* | (2006.01) |
| *C07K 16/30* | (2006.01) |

(52) U.S. Cl.
CPC .......... *A61K 47/68* (2017.08); *A61K 47/6803* (2017.08); *A61K 47/6811* (2017.08); *A61K 47/6817* (2017.08); *A61K 47/6889* (2017.08); *C07K 16/00* (2013.01); *C07K 16/30* (2013.01); *C07K 2317/40* (2013.01); *C07K 2317/52* (2013.01); *C07K 2317/524* (2013.01); *C07K 2317/526* (2013.01); *C07K 2317/71* (2013.01); *C07K 2317/73* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | |
|---|---|---|
| 2007/0111260 A1 | 5/2007 | Gao et al. |
| 2008/0050310 A1 | 2/2008 | Ebens et al. |
| 2011/0033378 A1 | 2/2011 | Dimasi et al. |
| 2012/0148580 A1 | 6/2012 | Chennamsetty et al. |
| 2017/0183414 A1* | 6/2017 | Dimasi .............. A61K 51/1027 |
| 2019/0040152 A1* | 2/2019 | Kinneer ............ A61K 47/6803 |

FOREIGN PATENT DOCUMENTS

| | | | | |
|---|---|---|---|---|
| WO | WO 2008/070593 A2 | 6/2008 | | |
| WO | WO-2011005481 A1 * | 1/2011 | ............. | C07K 16/00 |
| WO | WO 2013/055990 A1 | 4/2013 | | |
| WO | WO 2013/070565 A1 | 5/2013 | | |
| WO | WO 2014/124316 A2 | 8/2014 | | |

OTHER PUBLICATIONS

Dimasi et al, 2017, "Efficient Preparation of Site-Specific Antibody-Drug Conugates Using Cysteine Insertion", Molecular Pharmaceutics, 14:1501-1516.

* cited by examiner

*Primary Examiner* — Julie Wu

(57) ABSTRACT

This disclosure provides conjugate compounds comprising antibodies and fragments thereof engineered with one or more reactive cysteine residues and more specifically to conjugate compounds with therapeutic or diagnostic applications. The conjugate compounds comprise cysteine-engineered antibodies or fragments thereof conjugated, for example, with chemotherapeutic drugs, toxins, and detection labels such as radionuclides or fluorophores. The disclosure also provides methods of using the disclosed conjugate compounds for in vitro, in situ, ex vivo, and in vivo diagnosis or treatment of mammalian cells, or associated pathological conditions.

Figure 2B:
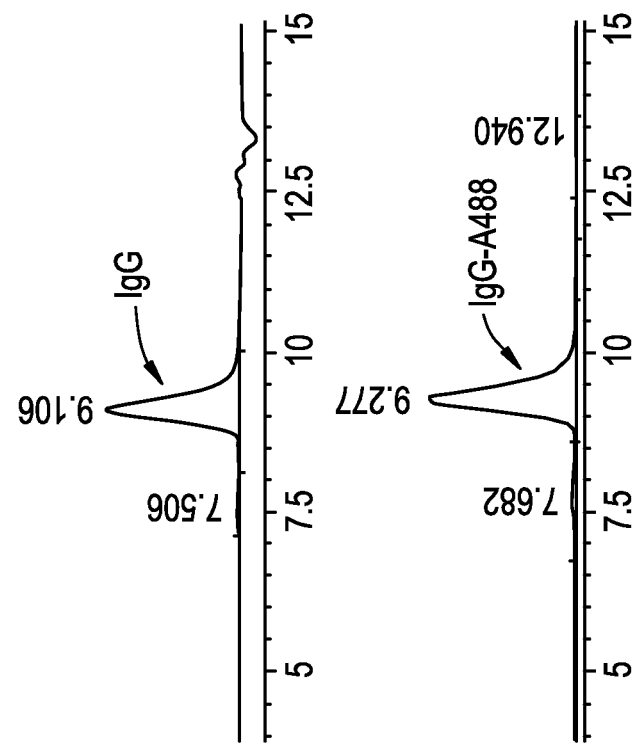

15 Claims, 24 Drawing Sheets
Specification includes a Sequence Listing.

CH2 Regions

FIG. 1A

*site of known allelic variation

CH3 Regions

| EU | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|---|---|---|---|---|---|---|---|
| IgG1 | G | Q | P | R | E | P | Q | V | Y | T | L | P | P | S | R | D* | E | L* | T | K | N | Q |
| IgG2 | G | Q | P | R | E | P | Q | V | Y | T | L | P | P | S | R | E | E | M | T | K | N | Q |
| IgG3 | G | Q | P | R | E | P | Q | V | Y | T | L | P | P | S | R | E | E | M | T | K | N | Q |
| IgG4 | G | Q | P | R | E | P | Q | V | Y | T | L | P | P | S | Q | E | E | M | T | K | N | Q |

| EU | 363 | 364 | 365 | 366 | 367 | 368 | 369 | 370 | 371 | 372 | 373 | 374 | 375 | 376 | 377 | 378 | 379 | 380 | 381 | 382 | 383 | 384 |
|---|---|---|---|---|---|---|---|---|---|---|---|---|---|---|---|---|---|---|---|---|---|---|
| IgG1 | V | S | L | T | C | L | V | K | G | F | Y | P | S | D | I | A | V | E | W | E | S | N |
| IgG2 | V | S | L | T | C | L | V | K | G | F | Y | P | S | D | I | S* | V | E | W | E | S | N |
| IgG3 | V | S | L | T | C | L | V | K | G | F | Y | P | S | D | I | A | V* | E | W | E | S | S* |
| IgG4 | V | S | L | T | C | L | V | K | G | F | Y | P | S | D | I | A | V | E | W | E | S | N |

| EU | 385 | 386 | 387 | 388 | 389 | 390 | 391 | 392 | 393 | 394 | 395 | 396 | 397 | 398 | 399 | 400 | 401 | 402 | 403 | 404 | 405 | 406 |
|---|---|---|---|---|---|---|---|---|---|---|---|---|---|---|---|---|---|---|---|---|---|---|
| IgG1 | G | Q | P | E | N | N | Y | K | T | T | P | P | V | L | D | S | D | G | S | F | F | L |
| IgG2 | G | Q | P | E | N | N | Y | K | T | T | P | P | M | L | D | S | D | G | S | F | F | L |
| IgG3 | G | Q | P | E | N | N* | Y | N | T | T | P | P | M* | L | D | S | D | G | S | F | F | L |
| IgG4 | G | Q | P | E | N | N | Y | K | T | T | P | P | V | L | D | S | D | G | S | F | F | L |

| EU | 407 | 408 | 409 | 410 | 411 | 412 | 413 | 414 | 415 | 416 | 417 | 418 | 419 | 420 | 421 | 422 | 423 | 424 | 425 | 426 | 427 | 428 |
|---|---|---|---|---|---|---|---|---|---|---|---|---|---|---|---|---|---|---|---|---|---|---|
| IgG1 | Y | S | K | L | T | V | D | K | S | R | W | Q | Q | G | N | V | F | S | C | S | V | M |
| IgG2 | Y | S | K | L | T | V | D | K | S | R | W | Q | Q | G | N | V | F | S | C | S | V | M |
| IgG3 | Y | S | K* | L | T | V | D | K | S | R | W | Q | Q | G | N | I* | F | S | C | S | V | M |
| IgG4 | Y | S | K | L | T | V | D | K | S | R | W | Q | E | G | N | V | F | S | C | S | V | M |

| EU | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|
| IgG1 | H | E | A | L | H | N | H | Y | T | Q | K | S | L | S | L | S | P | G | K |
| IgG2 | H | E | A | L | H | N | H | Y | T | Q | K | S | L | S | L | S | P | G | K |
| IgG3 | H | E | A | L | H | N | R | F | T | Q | K | S | L | S | L | S | P | G | K |
| IgG4 | H | E | A | L | H | N | H | Y | T | Q | K | S | L | S | L | S | L | G | K |

*site of known allelic variation

FIG. 1B

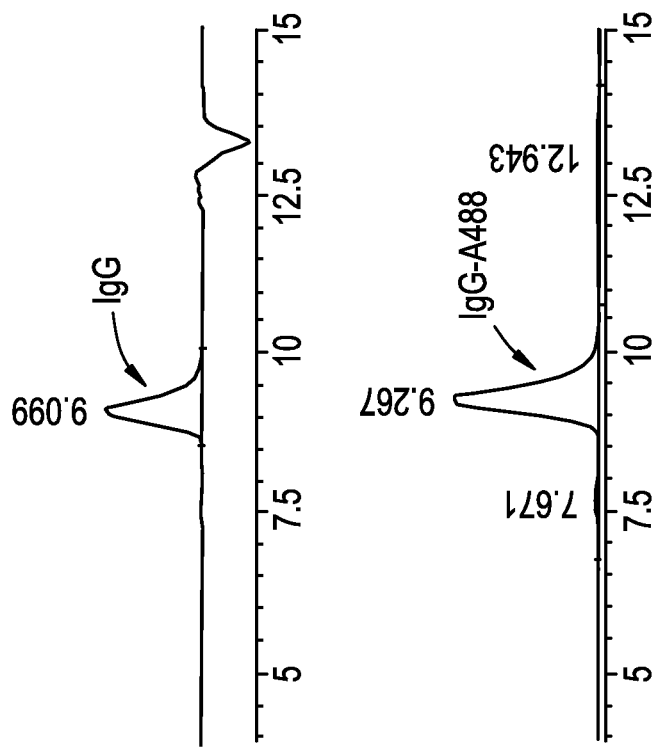
FIG. 2D E258C PBS 7 days
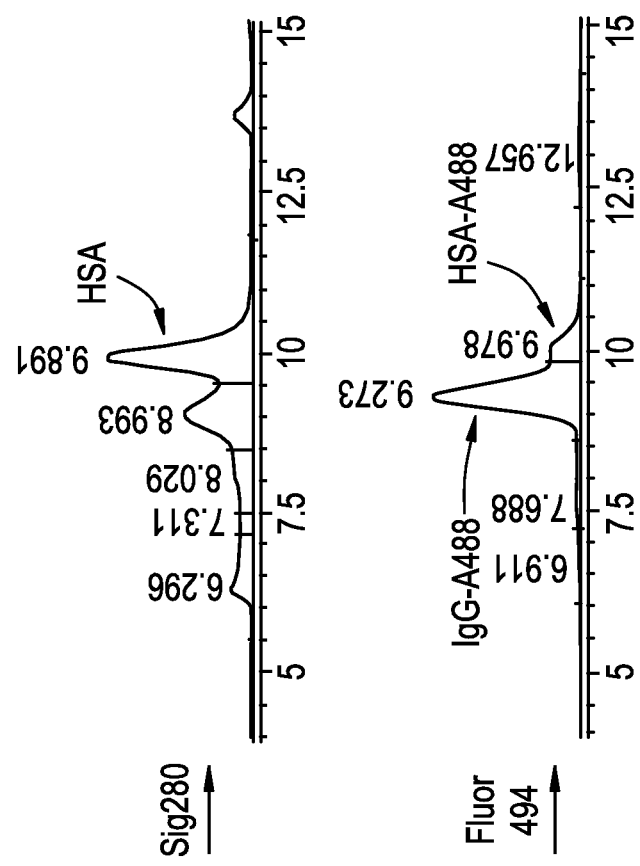
FIG. 2C E258C NHS 7 days

H435C PBS 0 day

H435C NHS 0 day

H435C PBS 7 days

H435C NHS 7 days

L443C PBS 0 day

L443C NHS 0 day

L443C PBS 7 days

L443C NHS 7 days

C239ins PBS 0 days

C239ins NHS 0 days

C239ins PBS 7 days

C239ins NHS 7 days

S239C PBS 0 day

S239C NHS 0 day

S239C NHS 7 days

S239C PBS 7 days

LC-V205C PBS 0 day

LC-V205C NHS 0 day

LC-V205C PBS 7 days

LC-V205C NHS 7 days

T289C PBS 0 day

T289C NHS 0 day

T289C PBS 7 days

T289C NHS 7 days

| FcR | wt (K_D, nM) | C239ins (K_D, nM) | S442C (K_D, nM) | L234F/S239A/S442C (K_D, nM) |
|---|---|---|---|---|
| huFcγRI | ~9 | ~133 | ~9 | ~16 |
| huFcγRIIA | 568 | N/A | 487 | 2540 |
| huFcγRIIb | 3360 | N/A | 2590 | 6310 |
| huFcγRIIIA-158V | 265 | N/A | 289 | 1455 |
| huFcγRIIIA-158F | 1300 | N/A | 1600 | 5700 |
| huFcRn (pH6) | 890 | 1050 | 1200 | 976 |

FIG. 11

SEQUENCE LISTING

<160> NUMBER OF SEQ ID NOS: 18

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(4)
<223> OTHER INFORMATION: This region may encompass 1-4 residues, wherein
      some positions may be absent
<220> FEATURE:
<221> NAME/KEY: MISC_FEATURE
<222> LOCATION: (5)..(5)
<223> OTHER INFORMATION: May or may not be present
<220> FEATURE:
<221> NAME/KEY: MISC_FEATURE
<222> LOCATION: (6)..(9)
<223> OTHER INFORMATION: This region may encompass 1-4 residues, wherein
      some positions may be absent
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(14)
<223> OTHER INFORMATION: This region may encompass 1-4 residues, wherein
      some positions may be absent
<220> FEATURE:
<221> NAME/KEY: MISC_FEATURE
<222> LOCATION: (15)..(15)
<223> OTHER INFORMATION: May or may not be present
<220> FEATURE:
<221> NAME/KEY: MISC_FEATURE
<222> LOCATION: (16)..(19)
<223> OTHER INFORMATION: This region may encompass 1-4 residues, wherein
      some positions may be absent
<220> FEATURE:
<221> NAME/KEY: MISC_FEATURE
<222> LOCATION: (20)..(20)
<223> OTHER INFORMATION: May or may not be present
<220> FEATURE:
<221> NAME/KEY: MISC_FEATURE
<222> LOCATION: (21)..(24)
<223> OTHER INFORMATION: This region may encompass 1-4 residues, wherein
      some positions may be absent
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MISC_FEATURE
<222> LOCATION: (26)..(29)
<223> OTHER INFORMATION: This region may encompass 1-4 residues, wherein
      some positions may be absent
<220> FEATURE:
<221> NAME/KEY: MISC_FEATURE
<222> LOCATION: (30)..(30)
<223> OTHER INFORMATION: May or may not be present
<220> FEATURE:

-continued

```
<221> NAME/KEY: MISC_FEATURE
<222> LOCATION: (31)..(34)
<223> OTHER INFORMATION: This region may encompass 1-4 residues, wherein
      some positions may be absent
<220> FEATURE:
<221> NAME/KEY: MISC_FEATURE
<222> LOCATION: (35)..(35)
<223> OTHER INFORMATION: May or may not be present
<220> FEATURE:
<221> NAME/KEY: MISC_FEATURE
<222> LOCATION: (36)..(39)
<223> OTHER INFORMATION: This region may encompass 1-4 residues, wherein
      some positions may be absent
<220> FEATURE:
<221> NAME/KEY: MISC_FEATURE
<222> LOCATION: (40)..(40)
<223> OTHER INFORMATION: May or may not be present
<220> FEATURE:
<221> NAME/KEY: MISC_FEATURE
<222> LOCATION: (41)..(44)
<223> OTHER INFORMATION: This region may encompass 1-4 residues, wherein
      some positions may be absent
<220> FEATURE:
<221> NAME/KEY: MISC_FEATURE
<222> LOCATION: (45)..(45)
<223> OTHER INFORMATION: May or may not be present
<220> FEATURE:
<221> NAME/KEY: MISC_FEATURE
<222> LOCATION: (46)..(49)
<223> OTHER INFORMATION: This region may encompass 1-4 residues, wherein
      some positions may be absent
<220> FEATURE:
<221> NAME/KEY: MISC_FEATURE
<222> LOCATION: (50)..(50)
<223> OTHER INFORMATION: May or may not be present
<220> FEATURE:
<221> NAME/KEY: MISC_FEATURE
<222> LOCATION: (51)..(54)
<223> OTHER INFORMATION: This region may encompass 1-4 residues, wherein
      some positions may be absent
<220> FEATURE:
<221> NAME/KEY: MISC_FEATURE
<222> LOCATION: (55)..(55)
<223> OTHER INFORMATION: May or may not be present
<220> FEATURE:
<221> NAME/KEY: MISC_FEATURE
<222> LOCATION: (56)..(59)
<223> OTHER INFORMATION: This region may encompass 1-4 residues, wherein
      some positions may be absent
<220> FEATURE:
<221> NAME/KEY: MISC_FEATURE
<222> LOCATION: (60)..(60)
<223> OTHER INFORMATION: May or may not be present
<220> FEATURE:
<221> NAME/KEY: MISC_FEATURE
<222> LOCATION: (61)..(64)
<223> OTHER INFORMATION: This region may encompass 1-4 residues, wherein
      some positions may be absent
<220> FEATURE:
<221> NAME/KEY: MISC_FEATURE
<222> LOCATION: (65)..(65)
<223> OTHER INFORMATION: May or may not be present
<220> FEATURE:
<221> NAME/KEY: MISC_FEATURE
<222> LOCATION: (66)..(69)
<223> OTHER INFORMATION: This region may encompass 1-4 residues, wherein
      some positions may be absent
<220> FEATURE:
<221> NAME/KEY: MISC_FEATURE
<222> LOCATION: (70)..(70)
<223> OTHER INFORMATION: May or may not be present
<220> FEATURE:
<221> NAME/KEY: MISC_FEATURE
<222> LOCATION: (71)..(74)
<223> OTHER INFORMATION: This region may encompass 1-4 residues, wherein
      some positions may be absent
<220> FEATURE:
<221> NAME/KEY: MISC_FEATURE
<222> LOCATION: (75)..(75)
```

```
<223> OTHER INFORMATION: May or may not be present
<220> FEATURE:
<221> NAME/KEY: MISC_FEATURE
<222> LOCATION: (76)..(79)
<223> OTHER INFORMATION: This region may encompass 1-4 residues, wherein
      some positions may be absent
<220> FEATURE:
<221> NAME/KEY: MISC_FEATURE
<222> LOCATION: (80)..(80)
<223> OTHER INFORMATION: May or may not be present
<220> FEATURE:
<221> NAME/KEY: MISC_FEATURE
<222> LOCATION: (81)..(84)
<223> OTHER INFORMATION: This region may encompass 1-4 residues, wherein
      some positions may be absent
<220> FEATURE:
<221> NAME/KEY: MISC_FEATURE
<222> LOCATION: (85)..(85)
<223> OTHER INFORMATION: May or may not be present
<220> FEATURE:
<221> NAME/KEY: MISC_FEATURE
<222> LOCATION: (86)..(89)
<223> OTHER INFORMATION: This region may encompass 1-4 residues, wherein
      some positions may be absent
<220> FEATURE:
<221> NAME/KEY: MISC_FEATURE
<222> LOCATION: (90)..(90)
<223> OTHER INFORMATION: May or may not be present
<220> FEATURE:
<221> NAME/KEY: MISC_FEATURE
<222> LOCATION: (91)..(94)
<223> OTHER INFORMATION: This region may encompass 1-4 residues, wherein
      some positions may be absent
<220> FEATURE:
<221> NAME/KEY: MISC_FEATURE
<222> LOCATION: (95)..(95)
<223> OTHER INFORMATION: May or may not be present
<220> FEATURE:
<221> NAME/KEY: MISC_FEATURE
<222> LOCATION: (96)..(99)
<223> OTHER INFORMATION: This region may encompass 1-4 residues, wherein
      some positions may be absent
<220> FEATURE:
<221> NAME/KEY: MISC_FEATURE
<222> LOCATION: (100)..(100)
<223> OTHER INFORMATION: May or may not be present
<220> FEATURE:
<221> NAME/KEY: MISC_FEATURE
<222> LOCATION: (101)..(104)
<223> OTHER INFORMATION: This region may encompass 1-4 residues, wherein
      some positions may be absent
<220> FEATURE:
<221> NAME/KEY: MISC_FEATURE
<222> LOCATION: (105)..(105)
<223> OTHER INFORMATION: May or may not be present
<220> FEATURE:
<221> NAME/KEY: MISC_FEATURE
<222> LOCATION: (106)..(109)
<223> OTHER INFORMATION: This region may encompass 1-4 residues, wherein
      some positions may be absent
<220> FEATURE:
<221> NAME/KEY: MISC_FEATURE
<222> LOCATION: (110)..(110)
<223> OTHER INFORMATION: May or may not be present
<220> FEATURE:
<221> NAME/KEY: MISC_FEATURE
<222> LOCATION: (111)..(114)
<223> OTHER INFORMATION: This region may encompass 1-4 residues, wherein
      some positions may be absent
<220> FEATURE:
<221> NAME/KEY: MISC_FEATURE
<222> LOCATION: (115)..(115)
<223> OTHER INFORMATION: May or may not be present
<220> FEATURE:
<221> NAME/KEY: MISC_FEATURE
<222> LOCATION: (116)..(119)
<223> OTHER INFORMATION: This region may encompass 1-4 residues, wherein
      some positions may be absent
<220> FEATURE:
```

-continued

```
<221> NAME/KEY: MISC_FEATURE
<222> LOCATION: (120)..(120)
<223> OTHER INFORMATION: May or may not be present
<220> FEATURE:
<221> NAME/KEY: MISC_FEATURE
<222> LOCATION: (121)..(124)
<223> OTHER INFORMATION: This region may encompass 1-4 residues, wherein
      some positions may be absent
<220> FEATURE:
<221> NAME/KEY: MISC_FEATURE
<222> LOCATION: (125)..(125)
<223> OTHER INFORMATION: May or may not be present
<220> FEATURE:
<221> NAME/KEY: MISC_FEATURE
<222> LOCATION: (126)..(129)
<223> OTHER INFORMATION: This region may encompass 1-4 residues, wherein
      some positions may be absent
<220> FEATURE:
<221> NAME/KEY: MISC_FEATURE
<222> LOCATION: (130)..(130)
<223> OTHER INFORMATION: May or may not be present
<220> FEATURE:
<221> NAME/KEY: MISC_FEATURE
<222> LOCATION: (131)..(134)
<223> OTHER INFORMATION: This region may encompass 1-4 residues, wherein
      some positions may be absent
<220> FEATURE:
<221> NAME/KEY: MISC_FEATURE
<222> LOCATION: (135)..(135)
<223> OTHER INFORMATION: May or may not be present
<220> FEATURE:
<221> NAME/KEY: MISC_FEATURE
<222> LOCATION: (136)..(139)
<223> OTHER INFORMATION: This region may encompass 1-4 residues, wherein
      some positions may be absent
<220> FEATURE:
<221> NAME/KEY: MISC_FEATURE
<222> LOCATION: (140)..(140)
<223> OTHER INFORMATION: May or may not be present
<220> FEATURE:
<221> NAME/KEY: MISC_FEATURE
<222> LOCATION: (141)..(144)
<223> OTHER INFORMATION: This region may encompass 1-4 residues, wherein
      some positions may be absent
<220> FEATURE:
<221> NAME/KEY: MISC_FEATURE
<222> LOCATION: (145)..(145)
<223> OTHER INFORMATION: May or may not be present
<220> FEATURE:
<221> NAME/KEY: MISC_FEATURE
<222> LOCATION: (146)..(149)
<223> OTHER INFORMATION: This region may encompass 1-4 residues, wherein
      some positions may be absent
<220> FEATURE:
<221> NAME/KEY: MISC_FEATURE
<222> LOCATION: (150)..(150)
<223> OTHER INFORMATION: May or may not be present
<220> FEATURE:
<221> NAME/KEY: MISC_FEATURE
<222> LOCATION: (151)..(154)
<223> OTHER INFORMATION: This region may encompass 1-4 residues, wherein
      some positions may be absent
<220> FEATURE:
<221> NAME/KEY: MISC_FEATURE
<222> LOCATION: (155)..(155)
<223> OTHER INFORMATION: May or may not be present
<220> FEATURE:
<221> NAME/KEY: MISC_FEATURE
<222> LOCATION: (156)..(159)
<223> OTHER INFORMATION: This region may encompass 1-4 residues, wherein
      some positions may be absent
<220> FEATURE:
<221> NAME/KEY: MISC_FEATURE
<222> LOCATION: (160)..(160)
<223> OTHER INFORMATION: May or may not be present
<220> FEATURE:
<221> NAME/KEY: MISC_FEATURE
<222> LOCATION: (161)..(164)
<223> OTHER INFORMATION: This region may encompass 1-4 residues, wherein
```

```
      some positions may be absent
<220> FEATURE:
<221> NAME/KEY: MISC_FEATURE
<222> LOCATION: (165)..(165)
<223> OTHER INFORMATION: May or may not be present
<220> FEATURE:
<221> NAME/KEY: MISC_FEATURE
<222> LOCATION: (166)..(169)
<223> OTHER INFORMATION: This region may encompass 1-4 residues, wherein
      some positions may be absent
<220> FEATURE:
<221> NAME/KEY: MISC_FEATURE
<222> LOCATION: (170)..(170)
<223> OTHER INFORMATION: May or may not be present
<220> FEATURE:
<221> NAME/KEY: MISC_FEATURE
<222> LOCATION: (171)..(174)
<223> OTHER INFORMATION: This region may encompass 1-4 residues, wherein
      some positions may be absent
<220> FEATURE:
<221> NAME/KEY: MISC_FEATURE
<222> LOCATION: (175)..(175)
<223> OTHER INFORMATION: May or may not be present
<220> FEATURE:
<221> NAME/KEY: MISC_FEATURE
<222> LOCATION: (176)..(179)
<223> OTHER INFORMATION: This region may encompass 1-4 residues, wherein
      some positions may be absent
<220> FEATURE:
<221> NAME/KEY: MISC_FEATURE
<222> LOCATION: (180)..(180)
<223> OTHER INFORMATION: May or may not be present
<220> FEATURE:
<221> NAME/KEY: MISC_FEATURE
<222> LOCATION: (181)..(184)
<223> OTHER INFORMATION: This region may encompass 1-4 residues, wherein
      some positions may be absent
<220> FEATURE:
<221> NAME/KEY: MISC_FEATURE
<222> LOCATION: (185)..(185)
<223> OTHER INFORMATION: May or may not be present
<220> FEATURE:
<221> NAME/KEY: MISC_FEATURE
<222> LOCATION: (186)..(189)
<223> OTHER INFORMATION: This region may encompass 1-4 residues, wherein
      some positions may be absent
<220> FEATURE:
<221> NAME/KEY: MISC_FEATURE
<222> LOCATION: (190)..(190)
<223> OTHER INFORMATION: May or may not be present
<220> FEATURE:
<221> NAME/KEY: MISC_FEATURE
<222> LOCATION: (191)..(194)
<223> OTHER INFORMATION: This region may encompass 1-4 residues, wherein
      some positions may be absent
<220> FEATURE:
<221> NAME/KEY: MISC_FEATURE
<222> LOCATION: (195)..(195)
<223> OTHER INFORMATION: May or may not be present
<220> FEATURE:
<221> NAME/KEY: MISC_FEATURE
<222> LOCATION: (196)..(199)
<223> OTHER INFORMATION: This region may encompass 1-4 residues, wherein
      some positions may be absent
<220> FEATURE:
<221> NAME/KEY: MISC_FEATURE
<222> LOCATION: (200)..(200)
<223> OTHER INFORMATION: May or may not be present
<220> FEATURE:
<221> NAME/KEY: MISC_FEATURE
<222> LOCATION: (201)..(204)
<223> OTHER INFORMATION: This region may encompass 1-4 residues, wherein
      some positions may be absent
<220> FEATURE:
<221> NAME/KEY: MISC_FEATURE
<222> LOCATION: (205)..(205)
<223> OTHER INFORMATION: May or may not be present
<220> FEATURE:
<221> NAME/KEY: MISC_FEATURE
```

```
<222> LOCATION: (206)..(209)
<223> OTHER INFORMATION: This region may encompass 1-4 residues, wherein
      some positions may be absent
<220> FEATURE:
<221> NAME/KEY: MISC_FEATURE
<222> LOCATION: (210)..(210)
<223> OTHER INFORMATION: May or may not be present
<220> FEATURE:
<221> NAME/KEY: MISC_FEATURE
<222> LOCATION: (211)..(214)
<223> OTHER INFORMATION: This region may encompass 1-4 residues, wherein
      some positions may be absent
<220> FEATURE:
<221> NAME/KEY: MISC_FEATURE
<222> LOCATION: (215)..(215)
<223> OTHER INFORMATION: May or may not be present
<220> FEATURE:
<221> NAME/KEY: MISC_FEATURE
<222> LOCATION: (216)..(219)
<223> OTHER INFORMATION: This region may encompass 1-4 residues, wherein
      some positions may be absent
<220> FEATURE:
<221> NAME/KEY: MISC_FEATURE
<222> LOCATION: (220)..(220)
<223> OTHER INFORMATION: May or may not be present
<220> FEATURE:
<221> NAME/KEY: MISC_FEATURE
<222> LOCATION: (221)..(224)
<223> OTHER INFORMATION: This region may encompass 1-4 residues, wherein
      some positions may be absent
<220> FEATURE:
<221> NAME/KEY: MISC_FEATURE
<222> LOCATION: (225)..(225)
<223> OTHER INFORMATION: May or may not be present
<220> FEATURE:
<221> NAME/KEY: MISC_FEATURE
<222> LOCATION: (226)..(229)
<223> OTHER INFORMATION: This region may encompass 1-4 residues, wherein
      some positions may be absent
<220> FEATURE:
<221> NAME/KEY: MISC_FEATURE
<222> LOCATION: (230)..(230)
<223> OTHER INFORMATION: May or may not be present
<220> FEATURE:
<221> NAME/KEY: MISC_FEATURE
<222> LOCATION: (231)..(234)
<223> OTHER INFORMATION: This region may encompass 1-4 residues, wherein
      some positions may be absent
<220> FEATURE:
<221> NAME/KEY: MISC_FEATURE
<222> LOCATION: (235)..(235)
<223> OTHER INFORMATION: May or may not be present
<220> FEATURE:
<221> NAME/KEY: MISC_FEATURE
<222> LOCATION: (236)..(239)
<223> OTHER INFORMATION: This region may encompass 1-4 residues, wherein
      some positions may be absent
<220> FEATURE:
<221> NAME/KEY: MISC_FEATURE
<222> LOCATION: (240)..(240)
<223> OTHER INFORMATION: May or may not be present
<220> FEATURE:
<221> NAME/KEY: MISC_FEATURE
<222> LOCATION: (241)..(244)
<223> OTHER INFORMATION: This region may encompass 1-4 residues, wherein
      some positions may be absent
<220> FEATURE:
<221> NAME/KEY: MISC_FEATURE
<222> LOCATION: (245)..(245)
<223> OTHER INFORMATION: May or may not be present
<220> FEATURE:
<221> NAME/KEY: MISC_FEATURE
<222> LOCATION: (246)..(249)
<223> OTHER INFORMATION: This region may encompass 1-4 residues, wherein
      some positions may be absent
<220> FEATURE:
<221> NAME/KEY: MISC_FEATURE
<222> LOCATION: (250)..(250)
<223> OTHER INFORMATION: May or may not be present
```

-continued

```
<220> FEATURE:
<221> NAME/KEY: MISC_FEATURE
<222> LOCATION: (1)..(250)
<223> OTHER INFORMATION: This sequence may encompass 1-50
      "(Gly)x-(Ser)y" repeating units, where x is from 1 to 4, y is 0 or
      1
<220> FEATURE:
<223> OTHER INFORMATION: See specification as filed for detailed
      description of substitutions and preferred embodiments

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser
                245                 250

<210> SEQ ID NO 3
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-100 residues,
      wherein some positions may be absent

<400> SEQUENCE: 3

Gly Gly Gly Gly Gly Gly Gly Gly Gly Gly Gly Gly Gly Gly Gly Gly
1               5                   10                  15
```

```
Gly Gly Gly Gly Gly Gly Gly Gly Gly Gly Gly Gly
            20                  25                  30

Gly Gly Gly Gly Gly Gly Gly Gly Gly Gly Gly Gly
        35                  40                  45

Gly Gly Gly Gly Gly Gly Gly Gly Gly Gly Gly Gly
    50                  55                  60

Gly Gly Gly Gly Gly Gly Gly Gly Gly Gly Gly Gly
65                  70                  75                  80

Gly Gly Gly Gly Gly Gly Gly Gly Gly Gly Gly Gly
            85                  90                  95

Gly Gly Gly Gly
        100

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly
1

<210> SEQ ID NO 5
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(200)
<223> OTHER INFORMATION: This sequence may encompass 1-100 "Gly Ala"
      repeating units, wherein some positions may be absent

<400> SEQUENCE: 5

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala Gly Ala Gly Ala Gly Ala Gly Ala
        35                  40                  45

Gly Ala Gly Ala Gly Ala Gly Ala Gly Ala Gly Ala Gly Ala Gly Ala
    50                  55                  60

Gly Ala Gly Ala Gly Ala Gly Ala Gly Ala Gly Ala Gly Ala Gly Ala
65                  70                  75                  80

Gly Ala Gly Ala Gly Ala Gly Ala Gly Ala Gly Ala Gly Ala Gly Ala
            85                  90                  95

Gly Ala Gly Ala Gly Ala Gly Ala Gly Ala Gly Ala Gly Ala Gly Ala
            100                 105                 110

Gly Ala Gly Ala Gly Ala Gly Ala Gly Ala Gly Ala Gly Ala Gly Ala
        115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

Gly Ala Gly Ala Gly Ala Gly Ala Gly Ala Gly Ala Gly Ala Gly Ala
```

```
                165                 170                 175
Gly Ala Gly Ala Gly Ala Gly Ala Gly Ala Gly Ala Gly Ala Gly Ala
        180                 185                 190
Gly Ala Gly Ala Gly Ala Gly Ala
        195                 200

<210> SEQ ID NO 6
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This sequence may encompass 1-100 "Gly Gly Ser"
      repeating units, wherein some positions may be absent

<400> SEQUENCE: 6

Gly Gly Ser Gly Gly Ser Gly Gly Ser Gly Gly Ser Gly Gly Ser Gly
1               5                   10                  15
Gly Ser Gly Gly Ser Gly Gly Ser Gly Gly Ser Gly Gly Ser Gly Gly
            20                  25                  30
Ser Gly Gly Ser Gly Gly Ser Gly Gly Ser Gly Gly Ser Gly Gly Ser
        35                  40                  45
Gly Gly Ser Gly Gly Ser Gly Gly Ser Gly Gly Ser Gly Gly Ser Gly
    50                  55                  60
Gly Ser Gly Gly Ser Gly Gly Ser Gly Gly Ser Gly Gly Ser Gly Gly
65                  70                  75                  80
Ser Gly Gly Ser Gly Gly Ser Gly Gly Ser Gly Gly Ser Gly Gly Ser
                85                  90                  95
Gly Gly Ser Gly Gly Ser Gly Gly Ser Gly Gly Ser Gly Gly Ser Gly
            100                 105                 110
Gly Ser Gly Gly Ser Gly Gly Ser Gly Gly Ser Gly Gly Ser Gly Gly
        115                 120                 125
Ser Gly Gly Ser Gly Gly Ser Gly Gly Ser Gly Gly Ser Gly Gly Ser
    130                 135                 140
Gly Gly Ser Gly Gly Ser Gly Gly Ser Gly Gly Ser Gly Gly Ser Gly
145                 150                 155                 160
Gly Ser Gly Gly Ser Gly Gly Ser Gly Gly Ser Gly Gly Ser Gly Gly
                165                 170                 175
Ser Gly Gly Ser Gly Gly Ser Gly Gly Ser Gly Gly Ser Gly Gly Ser
            180                 185                 190
Gly Gly Ser Gly Gly Ser Gly Gly Ser Gly Gly Ser Gly Gly Ser Gly
        195                 200                 205
Gly Ser Gly Gly Ser Gly Gly Ser Gly Gly Ser Gly Gly Ser Gly Gly
    210                 215                 220
Ser Gly Gly Ser Gly Gly Ser Gly Gly Ser Gly Gly Ser Gly Gly Ser
225                 230                 235                 240
Gly Gly Ser Gly Gly Ser Gly Gly Ser Gly Gly Ser Gly Gly Ser Gly
                245                 250                 255
Gly Ser Gly Gly Ser Gly Gly Ser Gly Gly Ser Gly Gly Ser Gly Gly
            260                 265                 270
Ser Gly Gly Ser Gly Gly Ser Gly Gly Ser Gly Gly Ser Gly Gly Ser
        275                 280                 285
Gly Gly Ser Gly Gly Ser Gly Gly Ser Gly Gly Ser
```

290                 295                 300

<210> SEQ ID NO 7
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(400)
<223> OTHER INFORMATION: This sequence may encompass 1-100 "Gly Gly Gly
      Ser" repeating units, wherein some positions may be absent

<400> SEQUENCE: 7

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
    130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
                165                 170                 175

Gly Gly Gly Ser Gly Gly Gly Ser Gly Gly Gly Ser Gly Gly Gly Ser
            180                 185                 190

Gly Gly Gly Ser Gly Gly Gly Ser Gly Gly Gly Ser Gly Gly Gly Ser
        195                 200                 205

Gly Gly Gly Ser Gly Gly Gly Ser Gly Gly Gly Ser Gly Gly Gly Ser
    210                 215                 220

Gly Gly Gly Ser Gly Gly Gly Ser Gly Gly Gly Ser Gly Gly Gly Ser
225                 230                 235                 240

Gly Gly Gly Ser Gly Gly Gly Ser Gly Gly Gly Ser Gly Gly Gly Ser
                245                 250                 255

Gly Gly Gly Ser Gly Gly Gly Ser Gly Gly Gly Ser Gly Gly Gly Ser
            260                 265                 270

Gly Gly Gly Ser Gly Gly Gly Ser Gly Gly Gly Ser Gly Gly Gly Ser
        275                 280                 285

Gly Gly Gly Ser Gly Gly Gly Ser Gly Gly Gly Ser Gly Gly Gly Ser
    290                 295                 300

Gly Gly Gly Ser Gly Gly Gly Ser Gly Gly Gly Ser Gly Gly Gly Ser
305                 310                 315                 320

Gly Gly Gly Ser Gly Gly Gly Ser Gly Gly Gly Ser Gly Gly Gly Ser

```
                       325                 330                 335
Gly Gly Gly Ser Gly Gly Gly Ser Gly Gly Gly Ser Gly Gly Gly Ser
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Ser Gly Gly Gly Ser Gly Gly Gly Ser
    370                 375                 380

Gly Gly Gly Ser Gly Gly Gly Ser Gly Gly Gly Ser Gly Gly Gly Ser
385                 390                 395                 400

<210> SEQ ID NO 8
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(300)
<223> OTHER INFORMATION: This region may encompass 1-100 "Gly Gly Ser"
      repeating units, wherein some positions may be absent
<220> FEATURE:
<221> NAME/KEY: MISC_FEATURE
<222> LOCATION: (301)..(800)
<223> OTHER INFORMATION: This region may encompass 1-100 "Gly Gly Gly
      Gly Ser" repeating units, wherein some positions may be absent

<400> SEQUENCE: 8

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
        100                 105                 110

Gly Ser Gly Gly Ser Gly Gly Ser Gly Gly Ser Gly Gly Ser Gly Gly
    115                 120                 125

Ser Gly Gly Ser Gly Gly Ser Gly Gly Ser Gly Gly Ser Gly Gly Ser
130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
            165                 170                 175

Ser Gly Gly Ser Gly Gly Ser Gly Gly Ser Gly Gly Ser Gly Gly Ser
        180                 185                 190

Gly Gly Ser Gly Gly Ser Gly Gly Ser Gly Gly Ser Gly Gly Ser Gly
    195                 200                 205

Gly Ser Gly Gly Ser Gly Gly Ser Gly Gly Ser Gly Gly Ser Gly Gly
    210                 215                 220

Ser Gly Gly Ser Gly Gly Ser Gly Gly Ser Gly Gly Ser Gly Gly Ser
225                 230                 235                 240
```

```
Gly Gly Ser Gly Gly Ser Gly Ser Gly Gly Ser Gly Gly Ser Gly
            245                 250                 255
Gly Ser Gly Gly Ser Gly Gly Ser Gly Gly Ser Gly Gly Ser Gly Gly
        260                 265                 270
Ser Gly Gly Ser Gly Gly Ser Gly Gly Ser Gly Gly Ser Gly Gly Ser
    275                 280                 285
Gly Gly Ser Gly Gly Ser Gly Gly Ser Gly Gly Ser Gly Gly Gly
        290                 295                 300
Ser Gly Gly Gly Gly Ser Gly Gly Gly Gly Ser Gly Gly Gly Gly Ser
305                 310                 315                 320
Gly Gly Gly Gly Ser Gly Gly Gly Gly Ser Gly Gly Gly Gly Ser Gly
                325                 330                 335
Gly Gly Gly Ser Gly Gly Gly Gly Ser Gly Gly Gly Ser Gly Gly
            340                 345                 350
Gly Gly Ser Gly Gly Gly Gly Ser Gly Gly Gly Gly Ser Gly Gly Gly
        355                 360                 365
Gly Ser Gly Gly Gly Gly Ser Gly Gly Gly Gly Ser Gly Gly Gly Gly
    370                 375                 380
Ser Gly Gly Gly Gly Ser Gly Gly Gly Gly Ser Gly Gly Gly Gly Ser
385                 390                 395                 400
Gly Gly Gly Gly Ser Gly Gly Gly Gly Ser Gly Gly Gly Gly Ser Gly
                405                 410                 415
Gly Gly Gly Ser Gly Gly Gly Gly Ser Gly Gly Gly Gly Ser Gly Gly
            420                 425                 430
Gly Gly Ser Gly Gly Gly Gly Ser Gly Gly Gly Gly Ser Gly Gly Gly
        435                 440                 445
Gly Ser Gly Gly Gly Gly Ser Gly Gly Gly Gly Ser Gly Gly Gly Gly
    450                 455                 460
Ser Gly Gly Gly Gly Ser Gly Gly Gly Gly Ser Gly Gly Gly Gly Ser
465                 470                 475                 480
Gly Gly Gly Gly Ser Gly Gly Gly Gly Ser Gly Gly Gly Gly Ser Gly
                485                 490                 495
Gly Gly Gly Ser Gly Gly Gly Ser Gly Gly Gly Gly Ser Gly Gly
            500                 505                 510
Gly Gly Ser Gly Gly Gly Gly Ser Gly Gly Gly Gly Ser Gly Gly Gly
        515                 520                 525
Gly Ser Gly Gly Gly Gly Ser Gly Gly Gly Gly Ser Gly Gly Gly Gly
    530                 535                 540
Ser Gly Gly Gly Gly Ser Gly Gly Gly Gly Ser Gly Gly Gly Gly Ser
545                 550                 555                 560
Gly Gly Gly Gly Ser Gly Gly Gly Gly Ser Gly Gly Gly Gly Ser Gly
                565                 570                 575
Gly Gly Gly Ser Gly Gly Gly Gly Ser Gly Gly Gly Gly Ser Gly Gly
            580                 585                 590
Gly Gly Ser Gly Gly Gly Gly Ser Gly Gly Gly Gly Ser Gly Gly Gly
        595                 600                 605
Gly Ser Gly Gly Gly Gly Ser Gly Gly Gly Gly Ser Gly Gly Gly Gly
    610                 615                 620
Ser Gly Gly Gly Gly Ser Gly Gly Gly Gly Ser Gly Gly Gly Gly Ser
625                 630                 635                 640
Gly Gly Gly Gly Ser Gly Gly Gly Gly Ser Gly Gly Gly Gly Ser Gly
                645                 650                 655
```

Gly Gly Gly Ser Gly Gly Gly Ser Gly Gly Gly Ser Gly Gly Gly
            660                 665                 670

Gly Gly Ser Gly Gly Gly Ser Gly Gly Gly Ser Gly Gly Gly
        675                 680                 685

Gly Ser Gly Gly Gly Ser Gly Gly Gly Ser Gly Gly Gly Gly
    690                 695                 700

Ser Gly Gly Gly Ser Gly Gly Gly Ser Gly Gly Gly Gly Ser
705                 710                 715                 720

Gly Gly Gly Ser Gly Gly Gly Ser Gly Gly Gly Ser Gly
            725                 730                 735

Gly Gly Gly Ser Gly Gly Gly Ser Gly Gly Gly Ser Gly Gly
            740                 745                 750

Gly Gly Ser Gly Gly Gly Ser Gly Gly Gly Ser Gly Gly Gly
        755                 760                 765

Gly Ser Gly Gly Gly Ser Gly Gly Gly Ser Gly Gly Gly Gly
    770                 775                 780

Ser Gly Gly Gly Ser Gly Gly Gly Ser Gly Gly Gly Gly Ser
785                 790                 795                 800

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Gly Ser Gly Gly Ser
1               5

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Gly Gly Ser Gly Gly Ser Gly Gly Ser Gly Gly Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ser Gly Gly Ser Gly Gly Gly Gly Ser Gly Gly Gly Gly Ser
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Gly Gly Ser Gly Gly Ser Gly Gly Ser Gly
1               5                   10                  15

Gly Ser

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(400)
<223> OTHER INFORMATION: This sequence may encompass 1-100 "Gly Gly Gly
      Gly" repeating units, wherein some positions may be absent

<400> SEQUENCE: 14

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly Gly Gly Gly Gly Gly Gly Gly
        195                 200                 205

Gly Gly Gly Gly Gly Gly Gly Gly Gly Gly Gly Gly Gly Gly Gly
    210                 215                 220

Gly Gly Gly Gly Gly Gly Gly Gly Gly Gly Gly Gly Gly Gly Gly

```
                225                 230                 235                 240
Gly Gly Gly Gly Gly Gly Gly Gly Gly Gly Gly Gly Gly
                245                 250                 255
Gly Gly Gly Gly Gly Gly Gly Gly Gly Gly Gly Gly Gly
                260                 265                 270
Gly Gly Gly Gly Gly Gly Gly Gly Gly Gly Gly Gly Gly
                275                 280                 285
Gly Gly Gly Gly Gly Gly Gly Gly Gly Gly Gly Gly Gly
                290                 295                 300
Gly Gly Gly Gly Gly Gly Gly Gly Gly Gly Gly Gly Gly
305                 310                 315                 320
Gly Gly Gly Gly Gly Gly Gly Gly Gly Gly Gly Gly Gly
                325                 330                 335
Gly Gly Gly Gly Gly Gly Gly Gly Gly Gly Gly Gly Gly
                340                 345                 350
Gly Gly Gly Gly Gly Gly Gly Gly Gly Gly Gly Gly Gly
                355                 360                 365
Gly Gly Gly Gly Gly Gly Gly Gly Gly Gly Gly Gly Gly
                370                 375                 380
Gly Gly Gly Gly Gly Gly Gly Gly Gly Gly Gly Gly Gly
385                 390                 395                 400

<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 16
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Pro Pro Val Ala Gly Pro Ser Val Phe Leu Phe Pro Lys Pro
1                5                  10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 17
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Pro Glu Leu Leu Gly Gly Pro Ser Val Phe Leu Phe Pro Pro Lys
1                5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
 50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
210                 215

<210> SEQ ID NO 18
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

```
Phe Ser Cys Ser Val Met His Glu Ala Leu His Asn His Tyr Thr Gln
        195             200                 205
Lys Ser Leu Ser Leu Ser Leu Gly Lys
    210             215
```

CONJUGATED COMPOUNDS COMPRISING CYSTEINE-ENGINEERED ANTIBODIES

CROSS-REFERENCE TO RELATED APPLICATIONS

This application is a U.S. National Stage application of International Application No. PCT/US2015/025237, filed on Apr. 10, 2015, said International Application No. PCT/US2015/025237 claims benefit under 35 U.S.C. § 119(e) of the U.S. Provisional Application No. 61/978,481, filed Apr. 11, 2014. Each of the above listed applications is incorporated by reference herein in its entirety for all purposes.

REFERENCE TO THE SEQUENCE LISTING

This application incorporates by reference a Sequence Listing submitted with this application as text file entitled CYS-115WO1_SL, created on Aug. 4, 2016, and having a size of 43.4 kilobytes.

BACKGROUND

The present disclosure provides cysteine-engineered antibodies and Fc fusion protein, and conjugate compounds comprising such cysteine-engineered molecules. Such conjugates can be utilized for diagnostic and therapeutic applications.

The use of antibodies has been established for the diagnosis and targeted treatment of patients with cancer, immunological and angiogenic disorders. The use of antibody-drug conjugates (ADC), i.e., immunoconjugates, for the local delivery of cytotoxic or cytostatic agents, i.e., drugs to kill or inhibit tumor cells in the treatment of cancer (Lambert (2005) Curr. Opinion in Pharmacology 5:543-549; Wu et al (2005) Nature Biotechnology 23:1137-1146; Payne (2003) Cancer Cell 3:207-21) theoretically allows targeted delivery of the drug moiety to tumors, where they bind to the target and may be internalized resulting in intracellular accumulation therein, where systemic administration of these unconjugated drug agents can result in unacceptable levels of toxicity to normal cells as well as the tumor cells sought to be eliminated. Efforts to design and refine ADC have focused on the selectivity of monoclonal antibodies (mAbs) as well as drug-linking and drug-releasing properties (Lambert, J. (2005) Curr. Opinion in Pharmacology 5:543-549). These methods include the conjugation of antibodies to drugs, toxins, radioisotopes, peptides, other antibodies, etc.

Conventional means of attaching, i.e., linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture.

Cysteine residues have been introduced into proteins by genetic engineering techniques to form covalent attachments to ligands or to form new intramolecular disulfide bonds. However, engineering cysteine thiol groups by the mutation of various amino acid residues of a protein to cysteine amino acids is potentially problematic, particularly in the case of unpaired (free cysteines) residues or those that are relatively accessible for reaction or oxidation. For example, formation of intramolecular or intermolecular disulfides can cause protein aggregation. The location of the engineered cysteine can affect the accessibility of the drugs during conjugation resulting in low yields. The introduction of new cysteines can render the antibody inactive or cause loss of binding specificity to its target due to misfolding or loss of tertiary structure (Zhang et al (2002) Anal. Biochem. 311:1-9). Also, the conjugated compounds can have poor serum stability, leading to loss of activity and degradation (e.g., by proteolytic degradation or clearance of the antibody moiety, or by hydrolysis of the drug moiety). Thus, it is an object of the present disclosure to provide improved cysteine engineering strategies capable of yielding conjugate compounds with enhanced stability, e.g., serum stability.

BRIEF SUMMARY

The present disclosure provides conjugate compounds comprising a cysteine-engineered antibody or Fc fusion protein and at least one heterologous moiety, wherein (i) the Fc domain of the antibody or Fc fusion protein thereof comprises at least one engineered cysteine amino acid selected from cysteine amino acid substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, a cysteine amino acid insertion between positions 239 and 240, and combinations thereof, wherein the amino acid position numbering is according to the EU index as set forth in Kabat (1991, NIH Publication 91-3242, National Technical Information Service, Springfield, Va.); and (ii) wherein at least one heterologous moiety is conjugated to one of the engineered cysteines.

In some aspects, the conjugate compound comprises 2 or more engineered cysteine amino acids.

In some aspects, the conjugate compounds have high stability in serum.

Another aspect of the disclosure provides nucleic acids, vectors and host cells for the generation of antibodies or Fc fusion proteins having at least one engineered cysteine amino acid as described herein.

Another aspect of the disclosure provides methods of making conjugate compounds comprising a cysteine-engineered antibody or Fc fusion protein and at least one heterologous moiety. In one embodiment, the heterologous moiety is a drug where the drug is chosen from cytotoxic agent, chemotherapeutic agent, peptide, peptidomimetic, protein scaffold, enzyme, toxin, radionuclide, DNA, RNA, siRNA, microRNA, peptidonucleic acid, fluorescent tag, or biotin.

Another aspect of the disclosure provides conjugate compounds of the disclosure, wherein the conjugate compounds are capable of internalizing when bound to cell surface receptors. In such aspects, conjugate compounds of the disclosure are useful for intracellular delivery of cargo molecules and/or agents.

Another aspect of the disclosure provides methods of treating, detecting, and diagnosing cancer, autoimmune, inflammatory, or infectious diseases with the conjugate compounds of the disclosure.

Another aspect of the disclosure provides compositions comprising the conjugate compounds of the disclosure.

BRIEF DESCRIPTION OF THE DRAWINGS/FIGURES

Figure 1A:
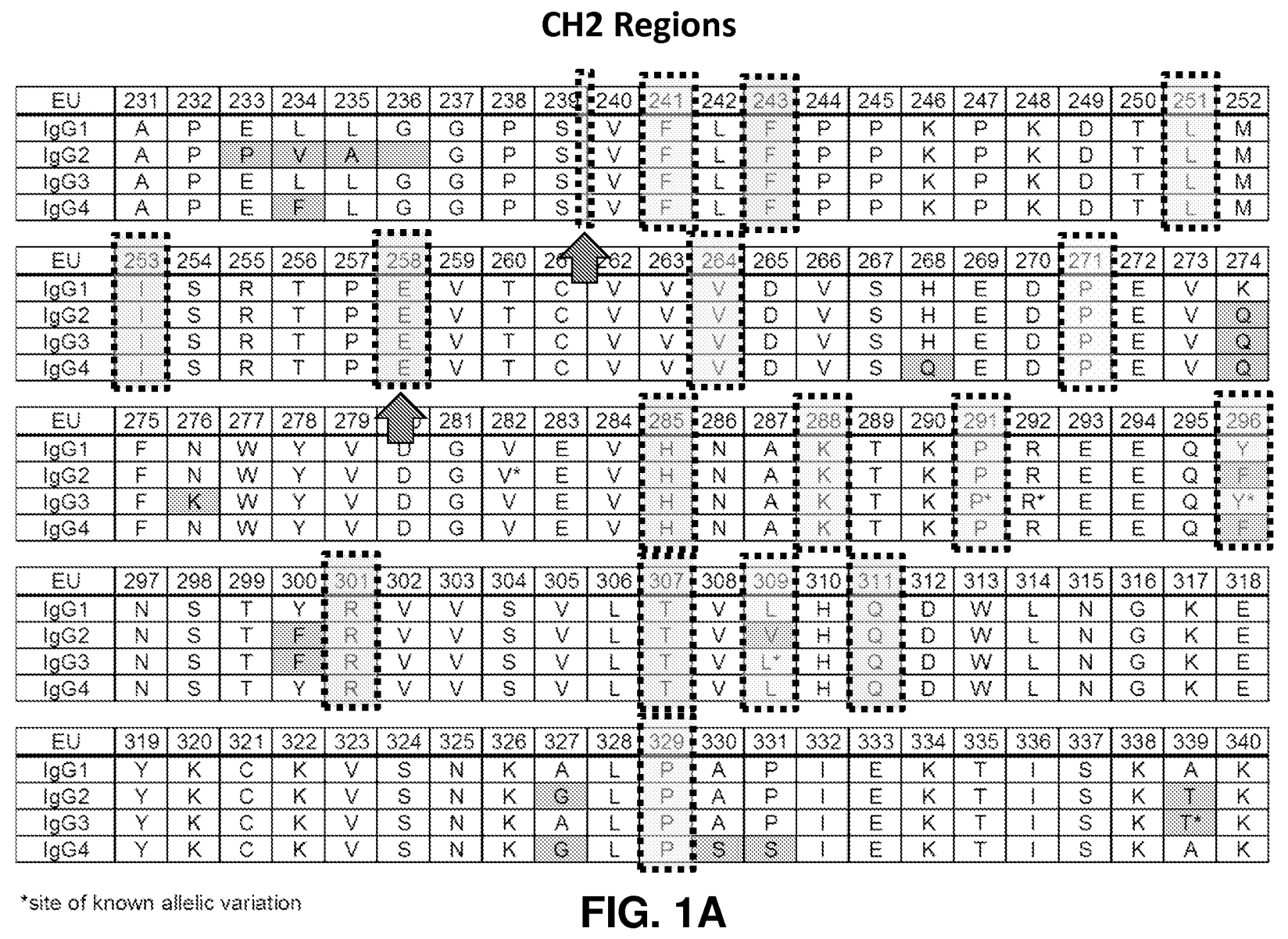

FIGS. 1A and 1B show the amino acid sequences and numbering for the CH2 and CH3 regions, respectively, of IgG heavy chains (IgG1, IgG2, IgG3 and IgG4) according to the EU index as set forth in Kabat (Kabat et al., Sequences of Proteins of Immunological Interest, 5th Ed. Public Health Service, National Institutes of Health, Bethesda, Md. (1991). Residues that differ from IgG1 are shaded and sites of known allelic variation are indicated by an asterisk (*). Shaded boxes indicate several of the cysteine substitution/insertion sites identified in Example 1 and arrows indicate the cysteine substitution/insertion sites tested for serum stability in the Examples provided herein.

Figure 2A:
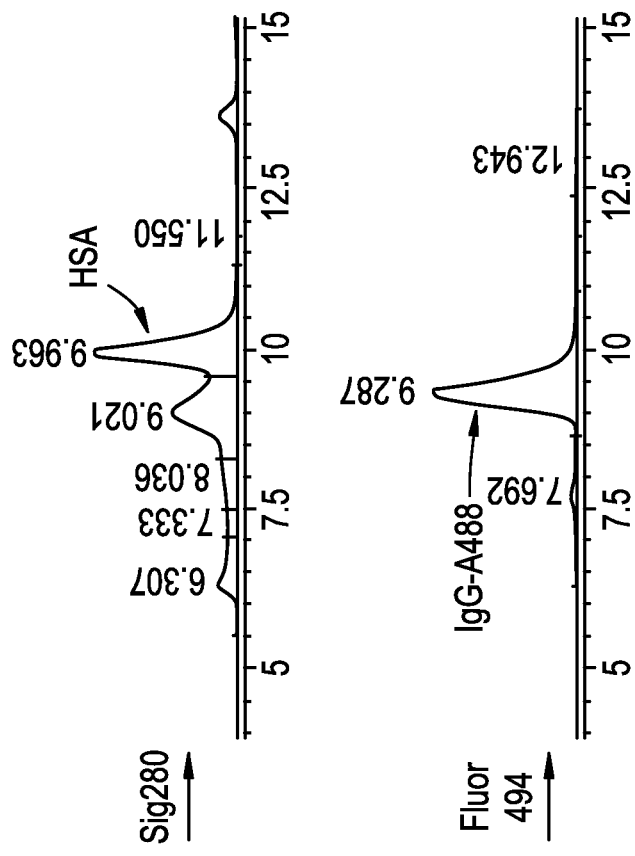
Figure 3B:
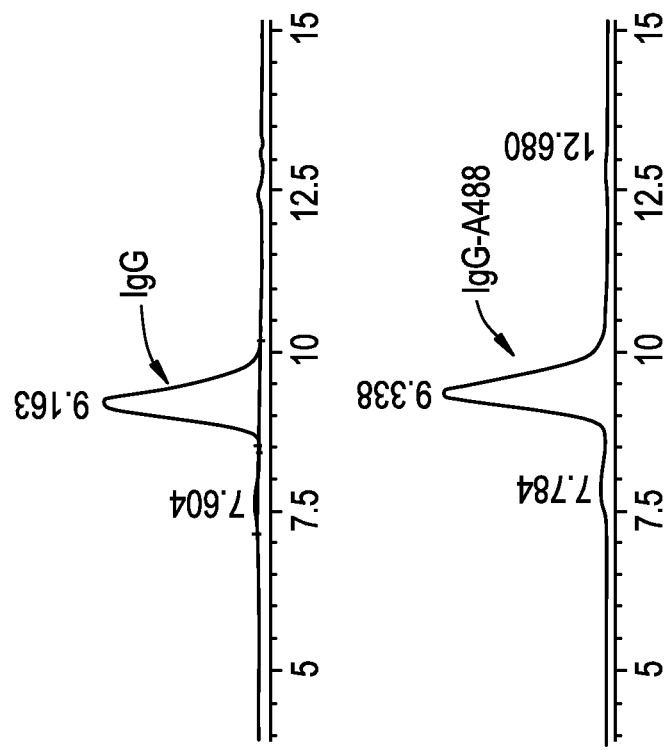
Figure 3A:
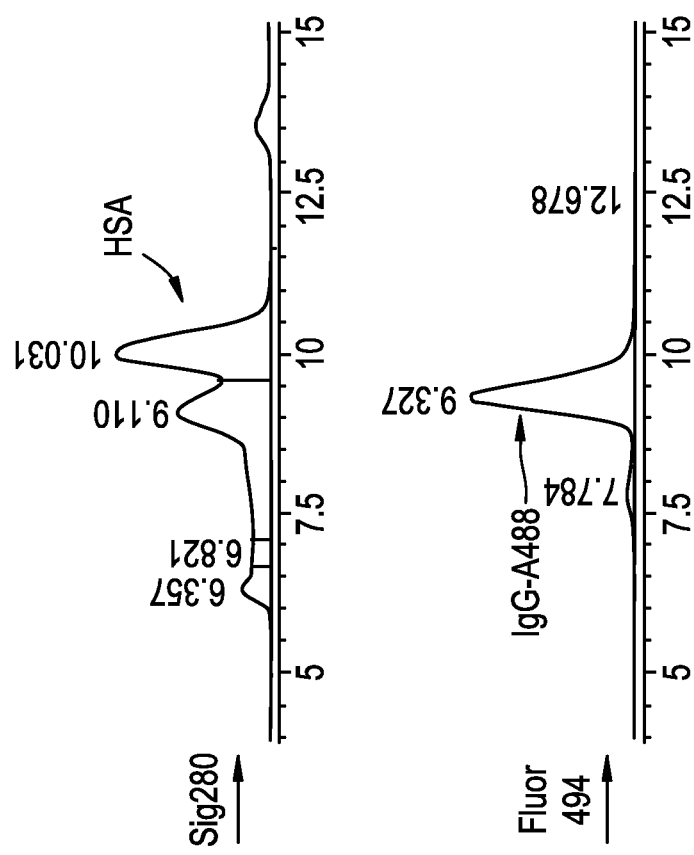
Figure 3D:
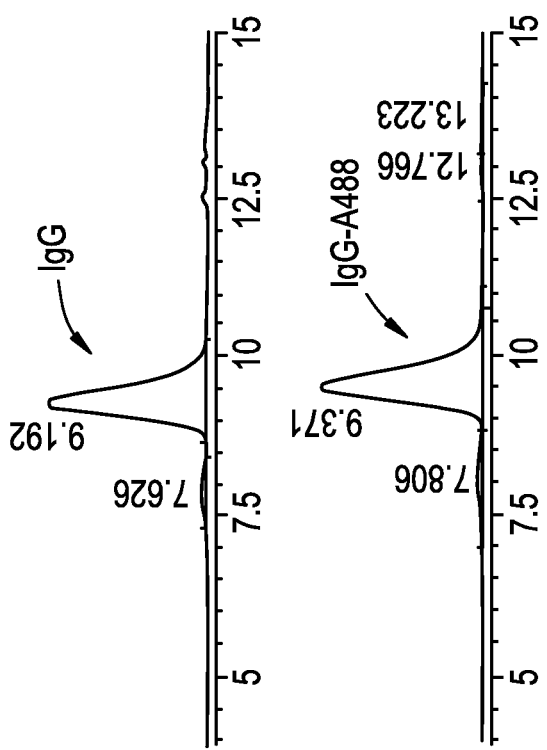
Figure 3C:
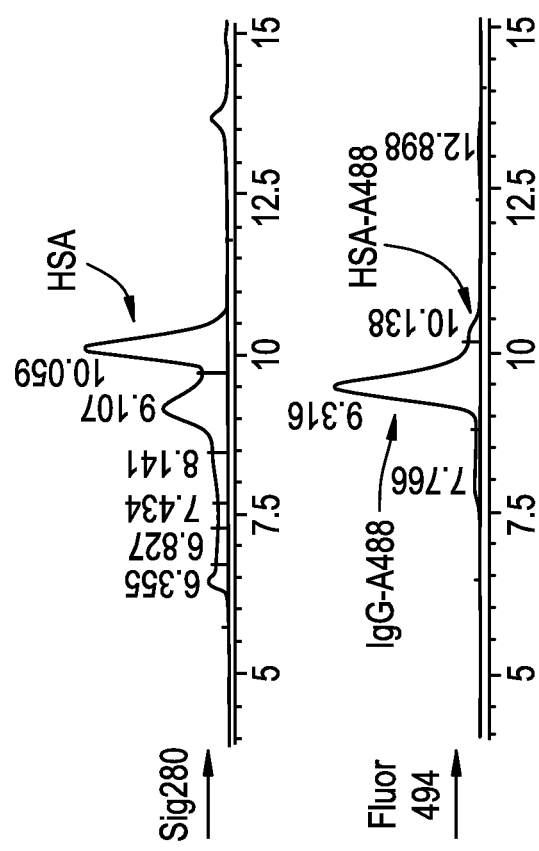
Figure 4B:
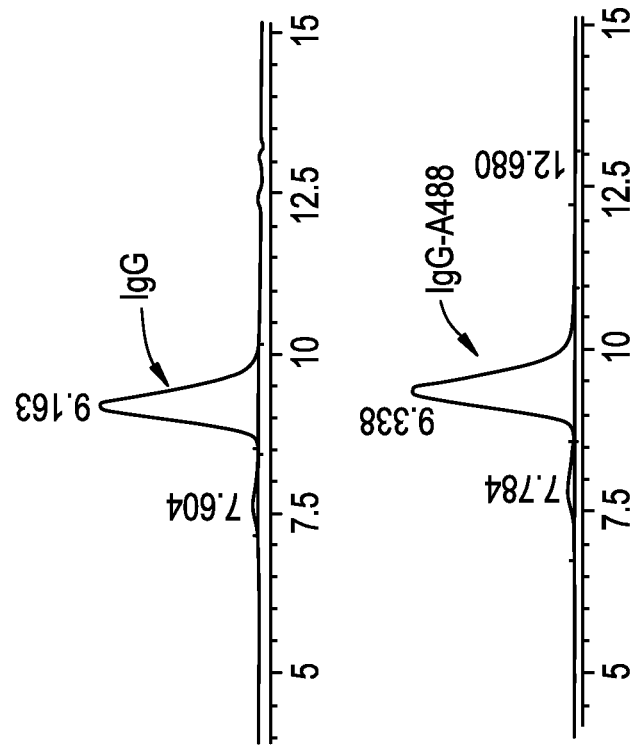
Figure 4A:
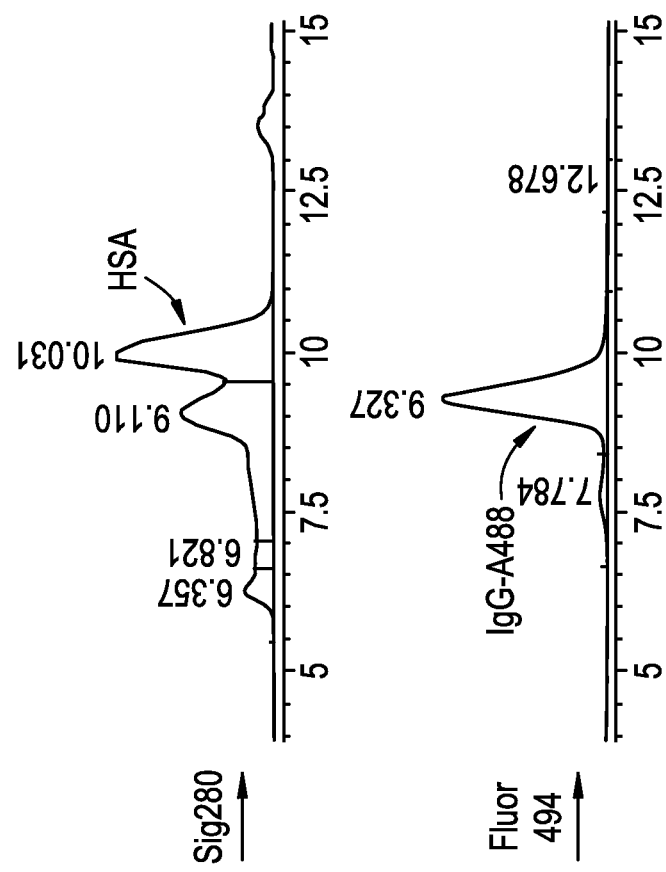
Figure 4D:
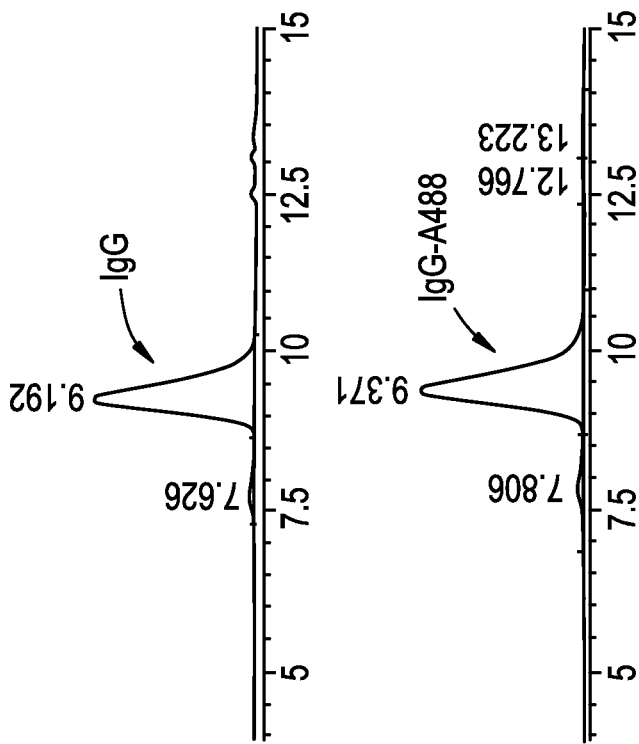
Figure 4C:
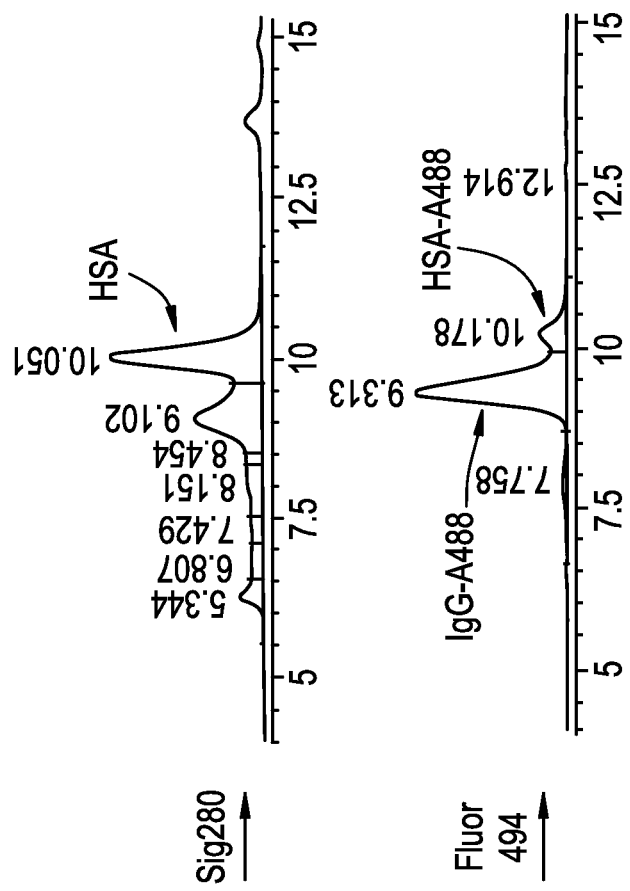
Figure 5B:
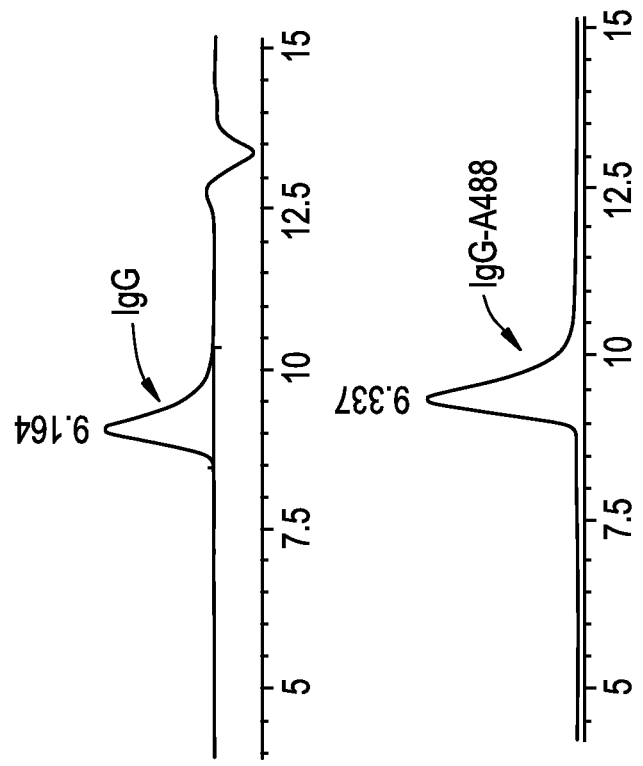
Figure 5A:
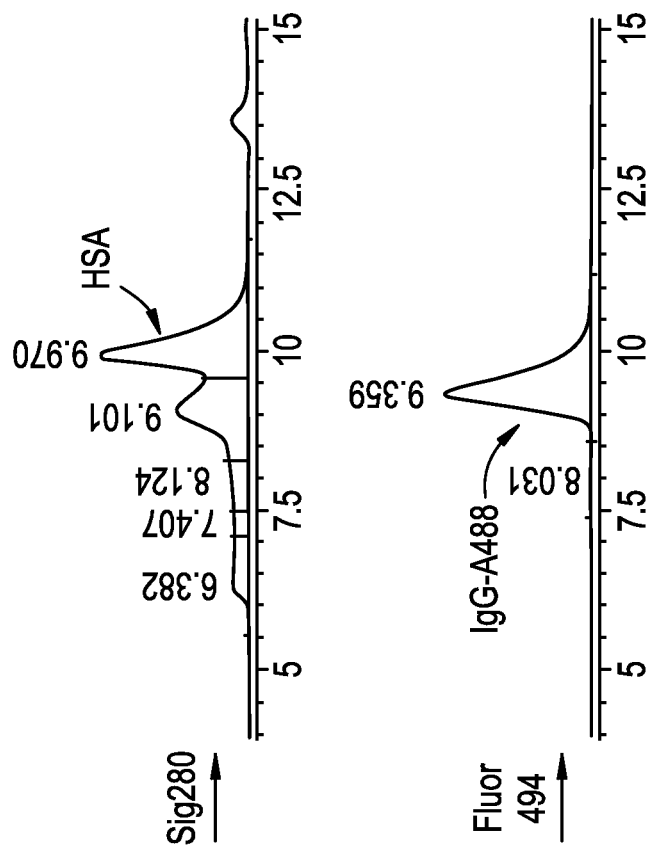
Figure 5D:
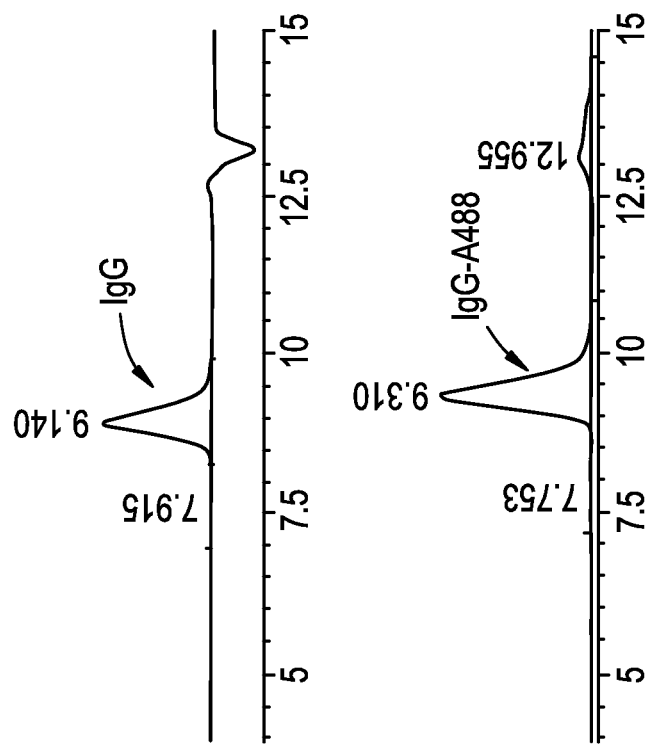
Figure 5C:
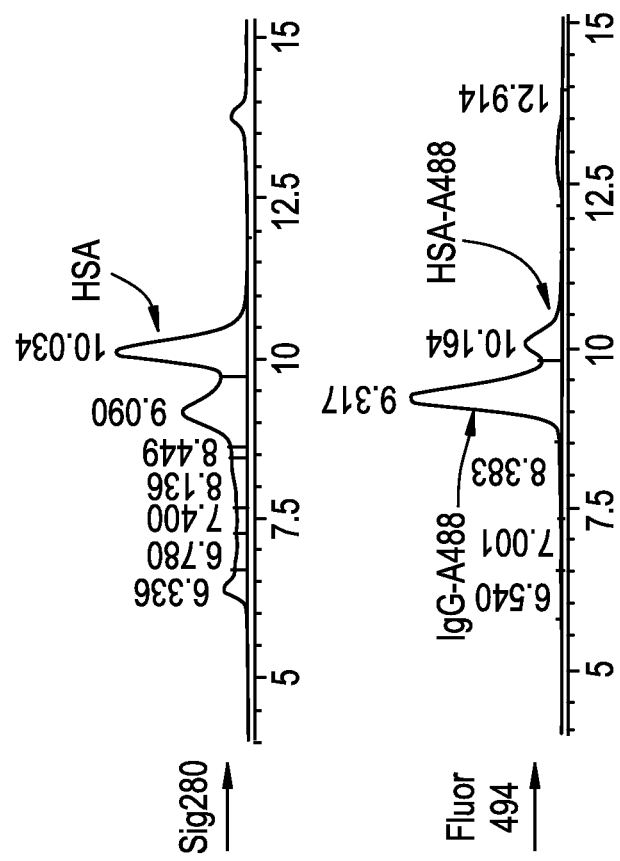
Figure 6B:
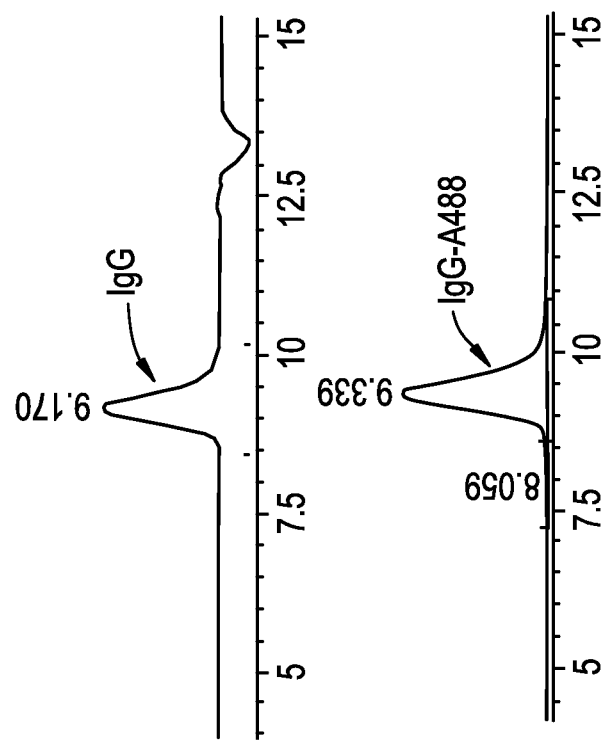
Figure 6A:
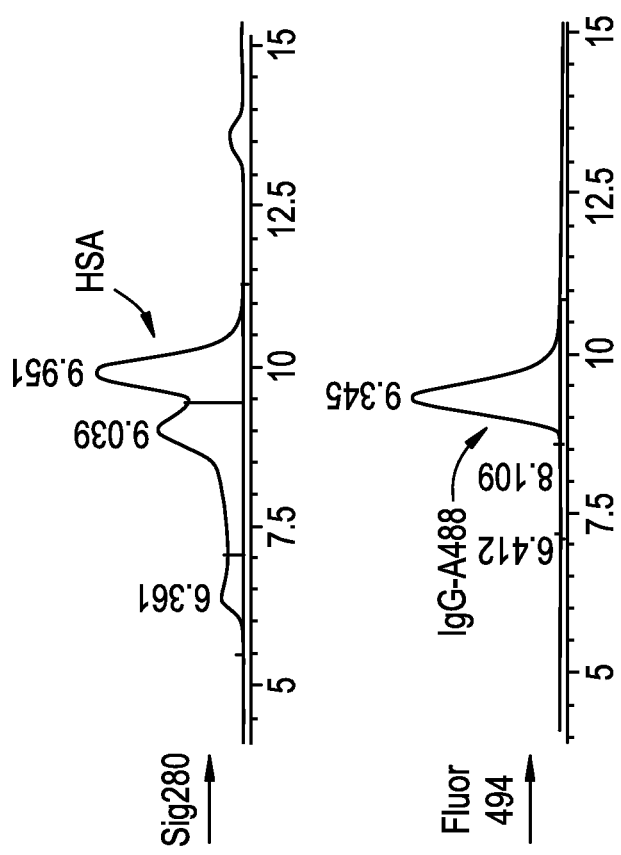
Figure 6C:
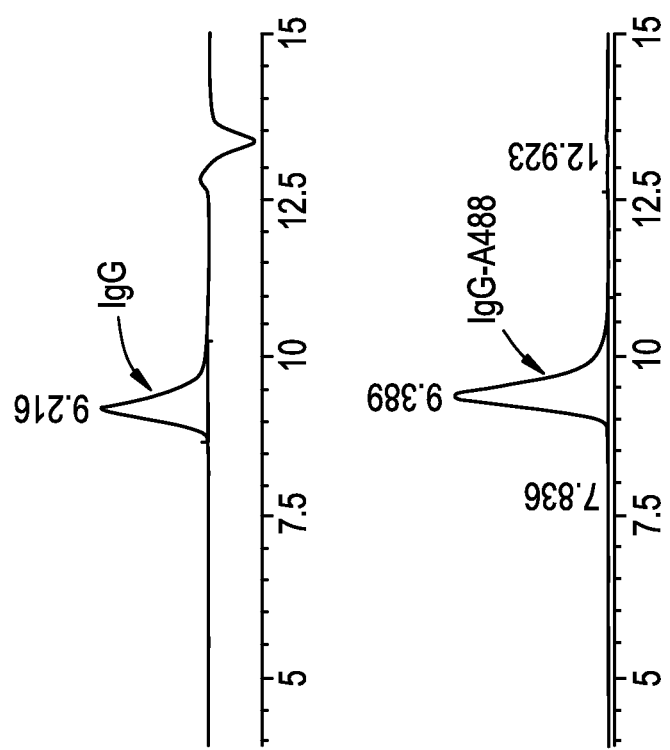
Figure 6D:
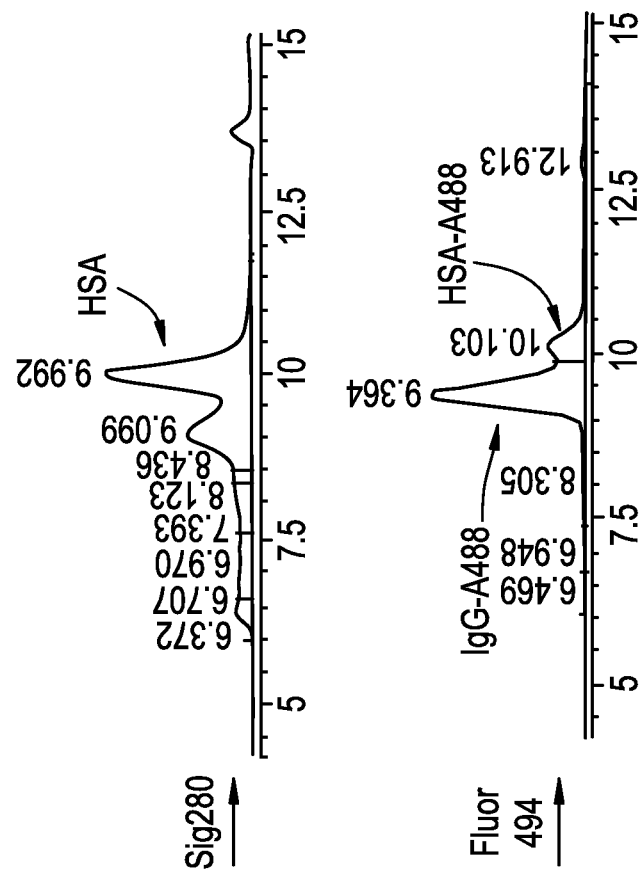
Figure 7B:
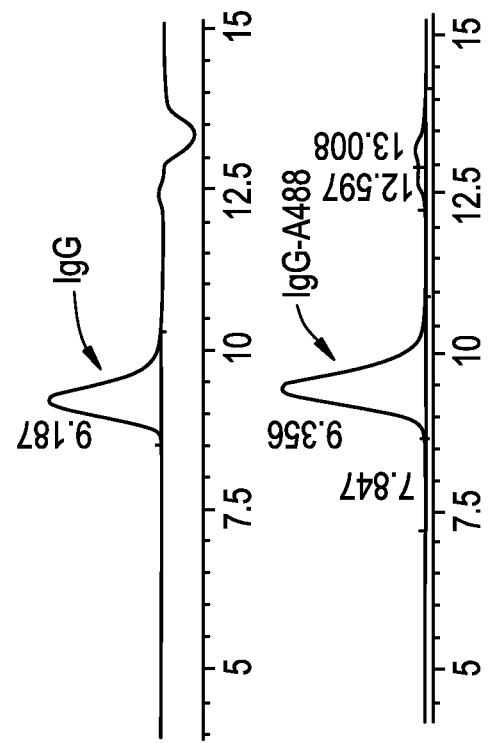
Figure 7A:
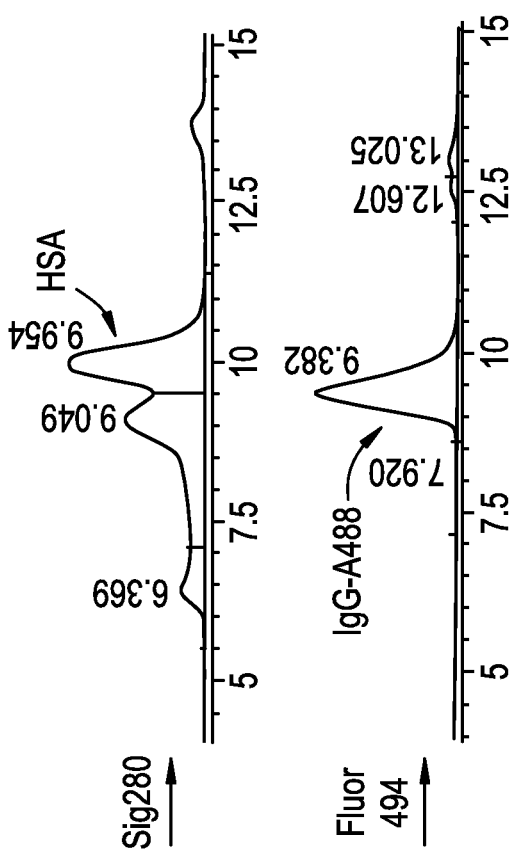
Figure 7D:
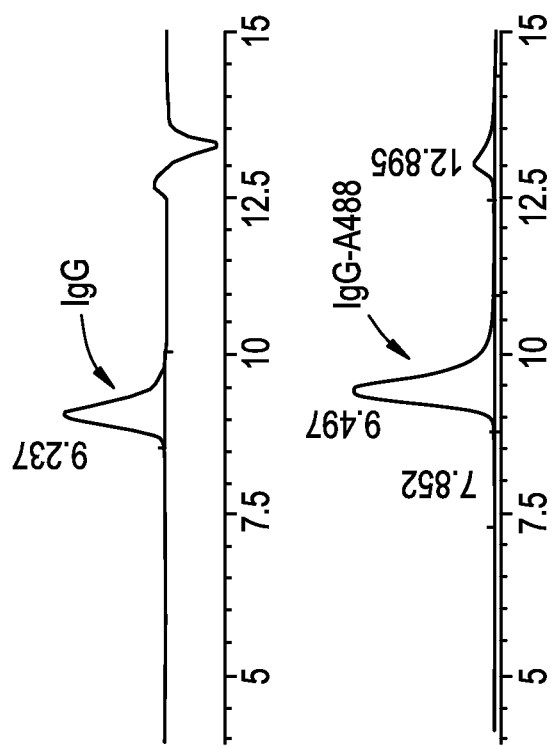
Figure 7C:
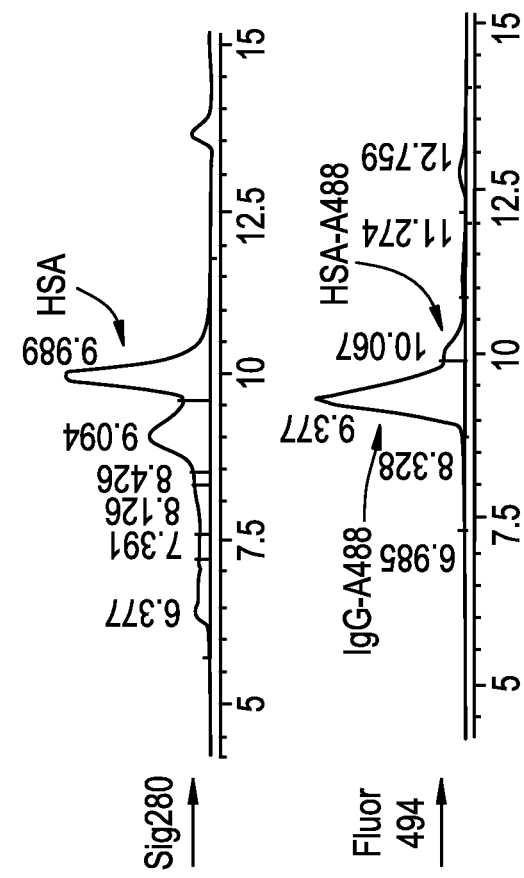
Figure 8B:
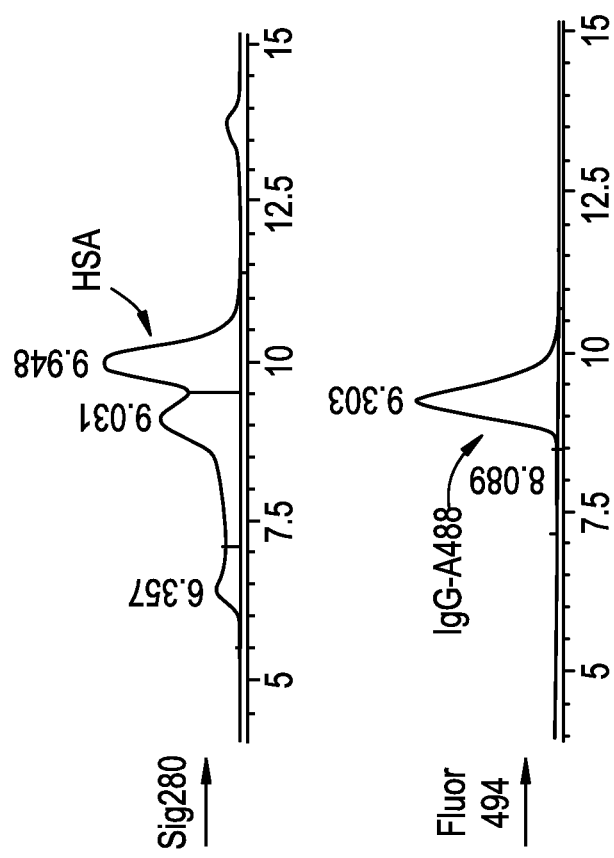
Figure 8A:
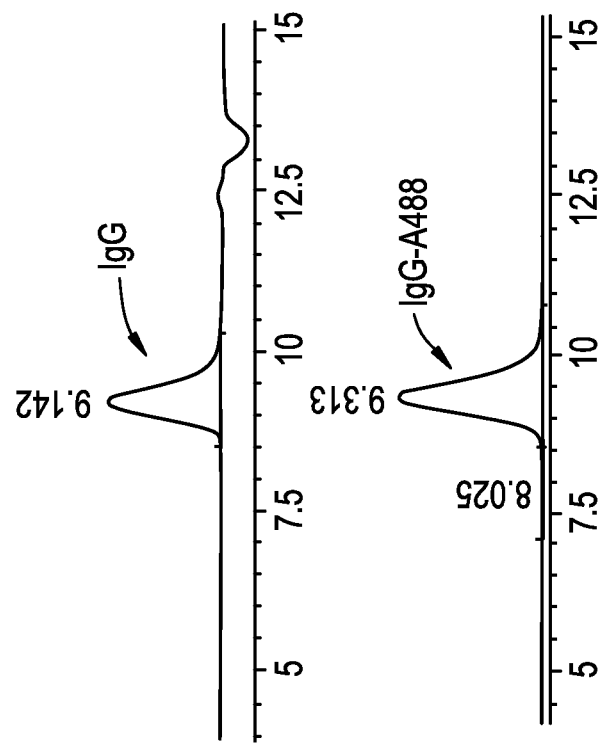
Figure 8D:
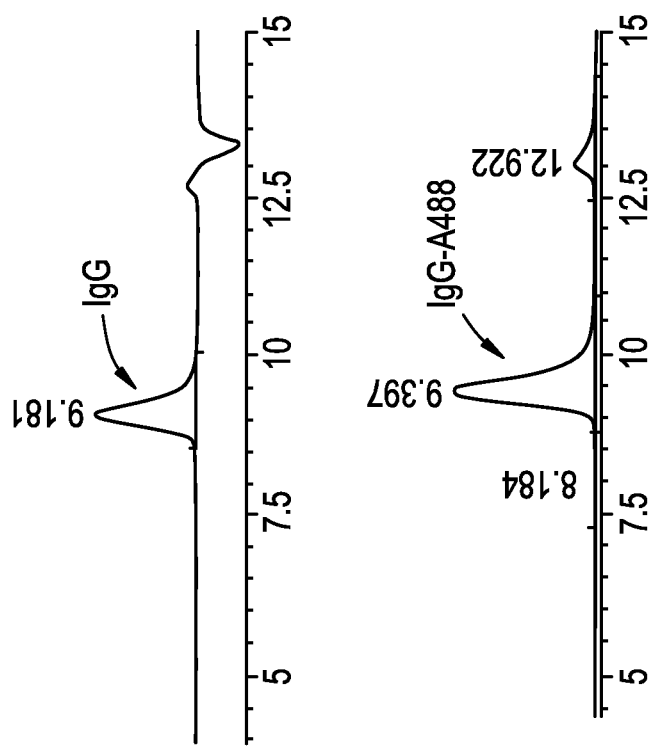
Figure 8C:
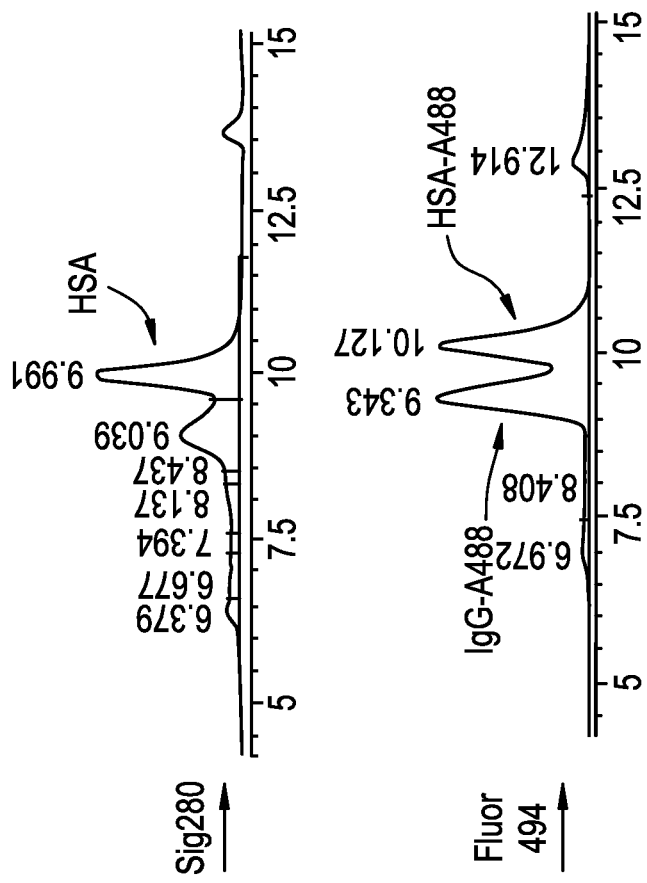

FIG. 2 shows size exclusion chromatography (SEC) profiles corresponding to a conjugate compound comprising the 1C1 antibody with a cysteine-engineered at EU position 258 (E258C) conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. The signal at 280 is total protein content in the sample and the signal at 494 is protein conjugated to the AF488. Only a small portion of AF488 was transferred to HSA after seven days of serum incubation.

FIG. 3 shows size exclusion chromatography (SEC) profiles corresponding to a conjugate compound comprising the 1C1 antibody with a cysteine-engineered at EU position 435 (H435C) conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. Only a small portion of AF488 was transferred to HSA after seven days of serum incubation.

FIG. 4 shows size exclusion chromatography (SEC) profiles corresponding to a conjugate compound comprising the 1C1 antibody with a cysteine-engineered at EU position 443 (L443C) conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. Only a small portion of AF488 was transferred to HSA after seven days of serum incubation.

FIG. 5 shows size exclusion chromatography (SEC) profiles corresponding to a conjugate compound comprising the 1C1 antibody with a cysteine-engineered at an insertion point between EU positions 239 and 240 (C239ins) conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. Only a small portion of AF488 was transferred to HSA after seven days of serum incubation.

FIG. 6 shows size exclusion chromatography (SEC) profiles corresponding to a conjugate compound comprising the 1C1 antibody with a cysteine-engineered at EU position 239 (S239C) conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. Only a small portion of AF488 was transferred to HSA after seven days of serum incubation.

FIG. 7 shows size exclusion chromatography (SEC) profiles corresponding to a conjugate compound comprising the 1C1 antibody with a cysteine-engineered in its light chain (LC) at EU position 205 (LC-V205C), a highly stabilizing mutation, conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. Only a small portion of AF488 was transferred to HSA after seven days of serum incubation.

FIG. 8 shows size exclusion chromatography (SEC) profiles corresponding to a conjugate compound comprising the 1C1 antibody with a cysteine-engineered at EU position 289 (T289C), a destabilizing mutation, conjugated to Alexa Fluor 488 (AF488) using maleimide chemistry. The conjugate compound was incubated with human serum (NHS) or phosphate buffered saline (PBS). Panel A shows NHS incubation at day 0, Panel B shows PBS incubation at day 0, Panel C shows NHS incubation after seven days, and Panel D shows PBS incubation after seven days. The majority of A488 was transferred to HSA after seven days of serum incubation.

Figure 9A:
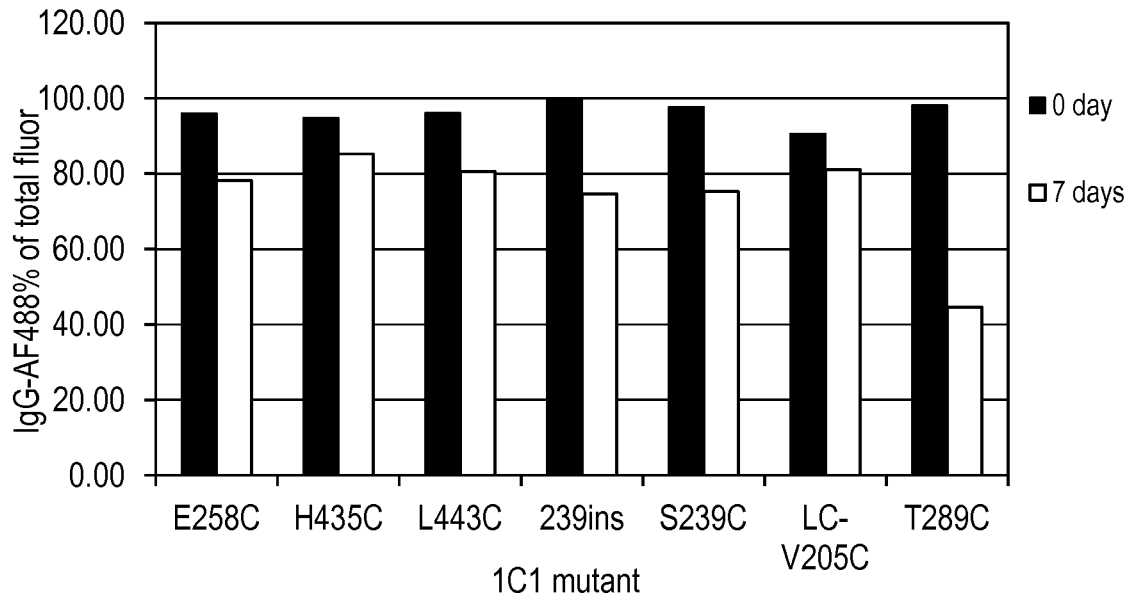
Figure 9B:
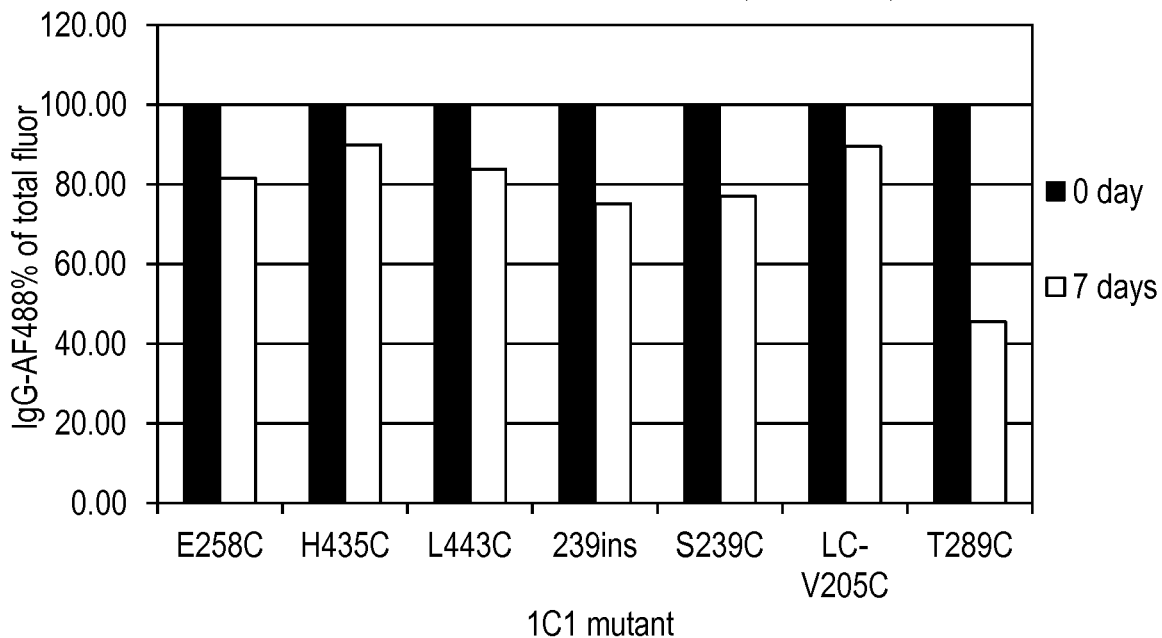

FIG. 9 shows raw data (Panel A) and data normalized with respect to day 0 (Panel B) corresponding to the experimental data provided in FIGS. 2 to 8. The new cysteine-engineered 1C1 antibodies comprising the E258C, H435, L443 and C239ins mutations and conjugated with AF488 were stable after 7 days of serum incubation. The stability of the newly engineered compounds was comparable to that of the 1C1-LC-V205C-AF488 stable site control. The 1C1-T289C-AF488 conjugate compound was a comparator site control.

Figure 10:
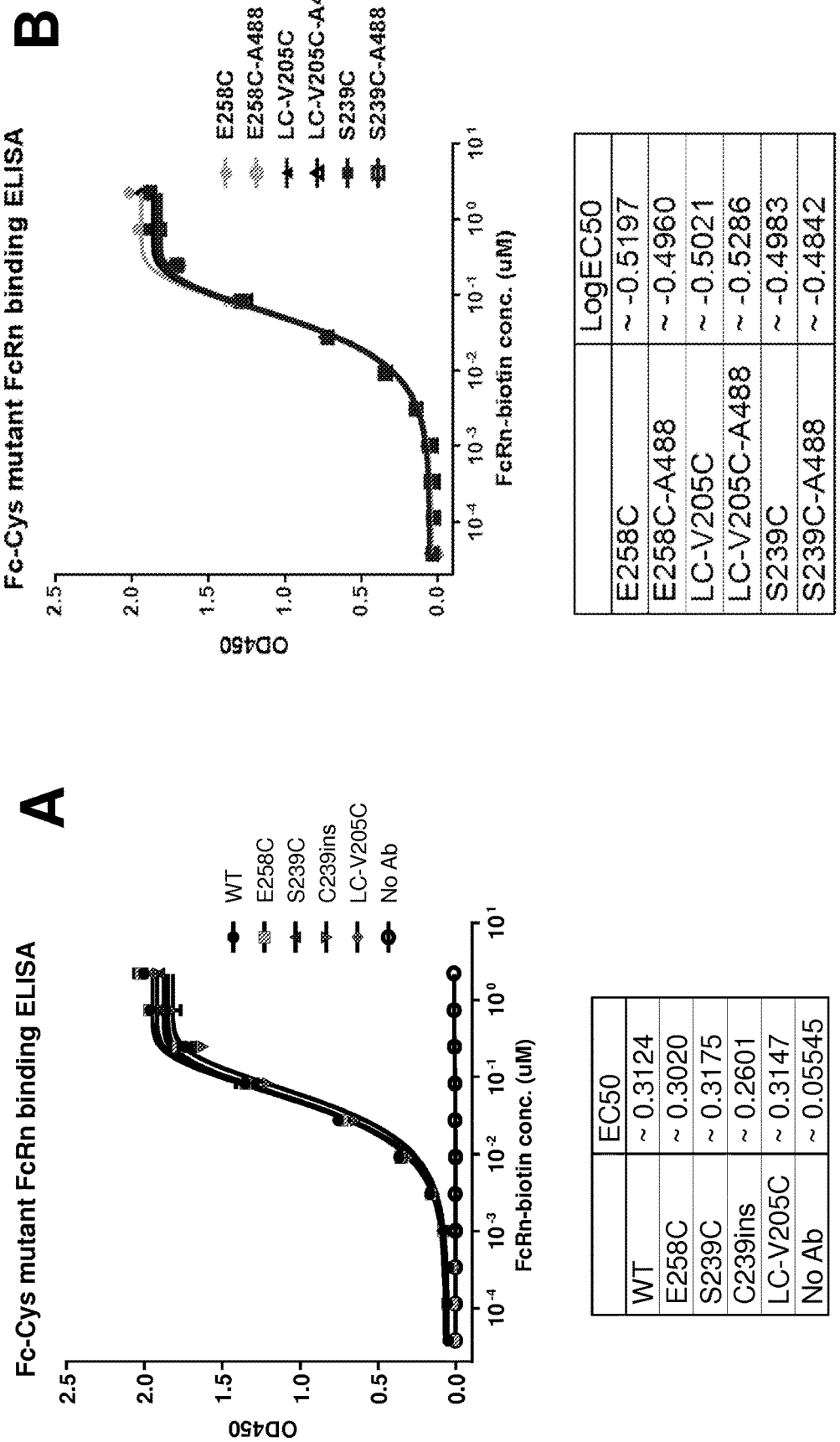

FIG. 10 shows that the EU E258C and C239ins mutations did not affect FcRn binding. FIG. 10A shows that when antibodies bearing the indicated mutations at the indicated positions are immobilized on an ELISA plate, FcRn is capable of binding to a similar level compared to an antibody bearing a WT IgG1 Fc. FIG. 10B shows that when antibodies bearing the indicated mutations at the indicated positions with or without conjugation to AF488 using maleimide chemistry are immobilized on an ELISA plate, FcRn is capable of binding to a similar level compared to an antibody bearing a WT IgG1 Fc. Tables presenting the $LogEC_{50}$ values for each one of the curves are also shown.

FIG. 11 shows the binding affinity of an antibody having a wild type Fc region or a cysteine engineered Fc region to the human Fc Receptors, FcγRI, FcγRIIa, FcγRIIb, FcγRIIIa (both the 158V and 158F alleles) and FcRn. "N/A" denotes that binding was too weak to obtain a reliable estimate for KD. Binding to FcRn at pH6 is provided.

Figure 12:
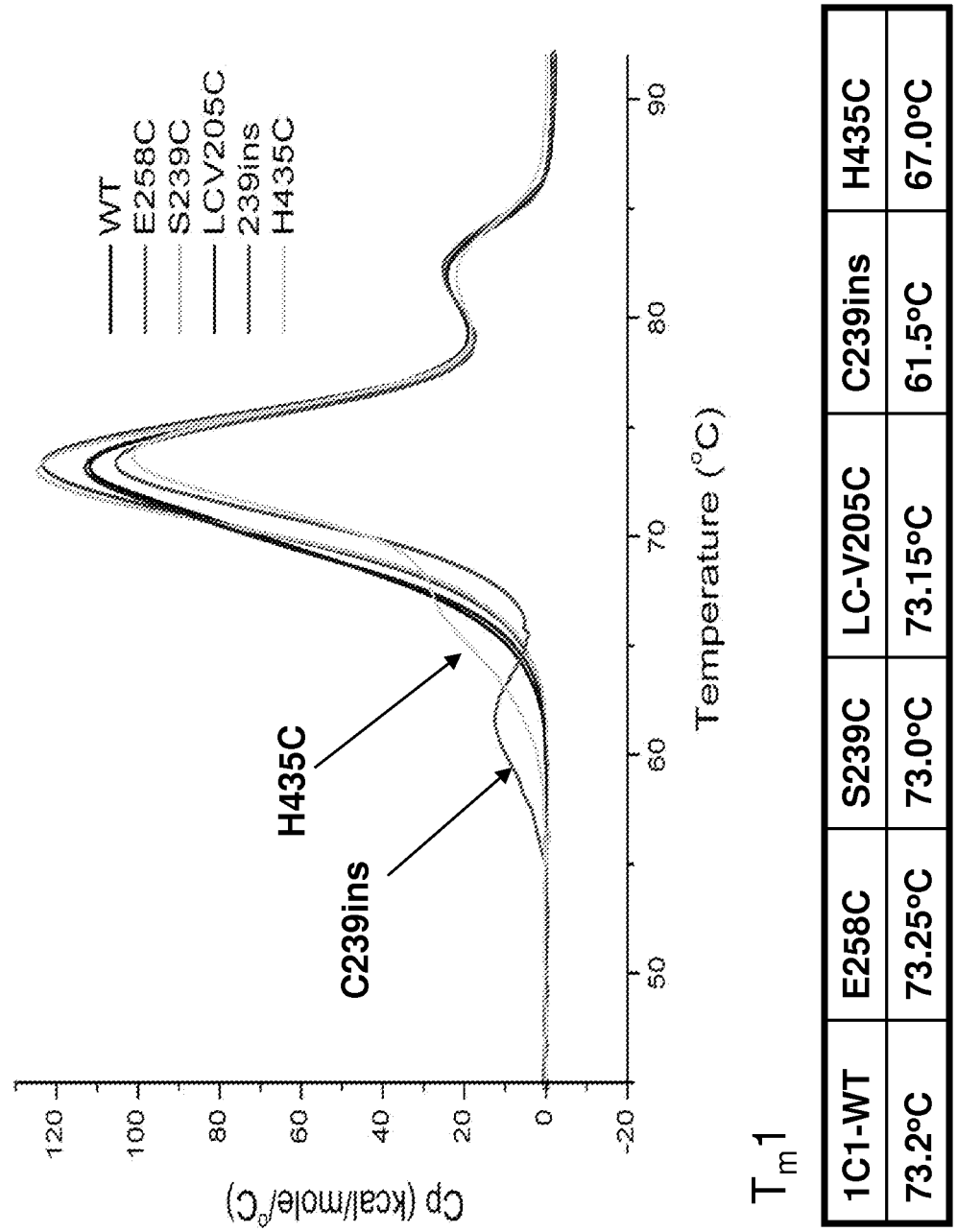

FIG. 12 shows the differential scanning calorimetry (DSC) profiles of the wild-type (WT), E258C, S239C, C239ins, H435C, and Lc-V205C mutation. The profiles of E258C, S239C, and Lc-V205C are similar to that of WT while a new lower melting peak appears for both the C239ins and H435C mutants. Also shown is a table presenting $T_m1$ values derived from the DSC thermograms.

Figure 13:
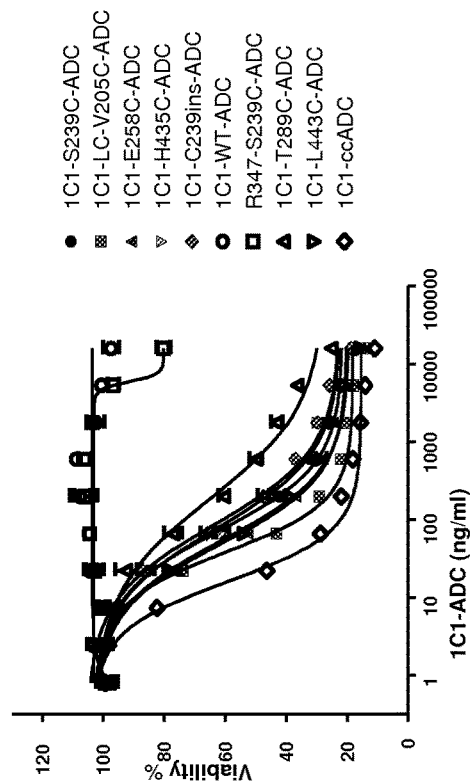
Figure 13:
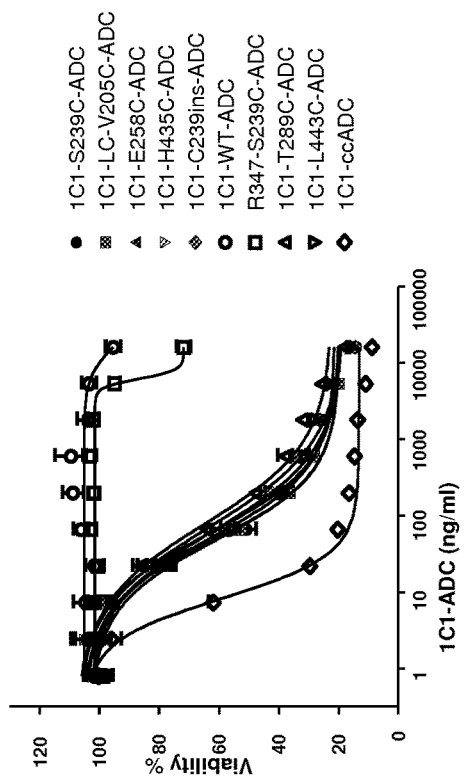
Figure 13:
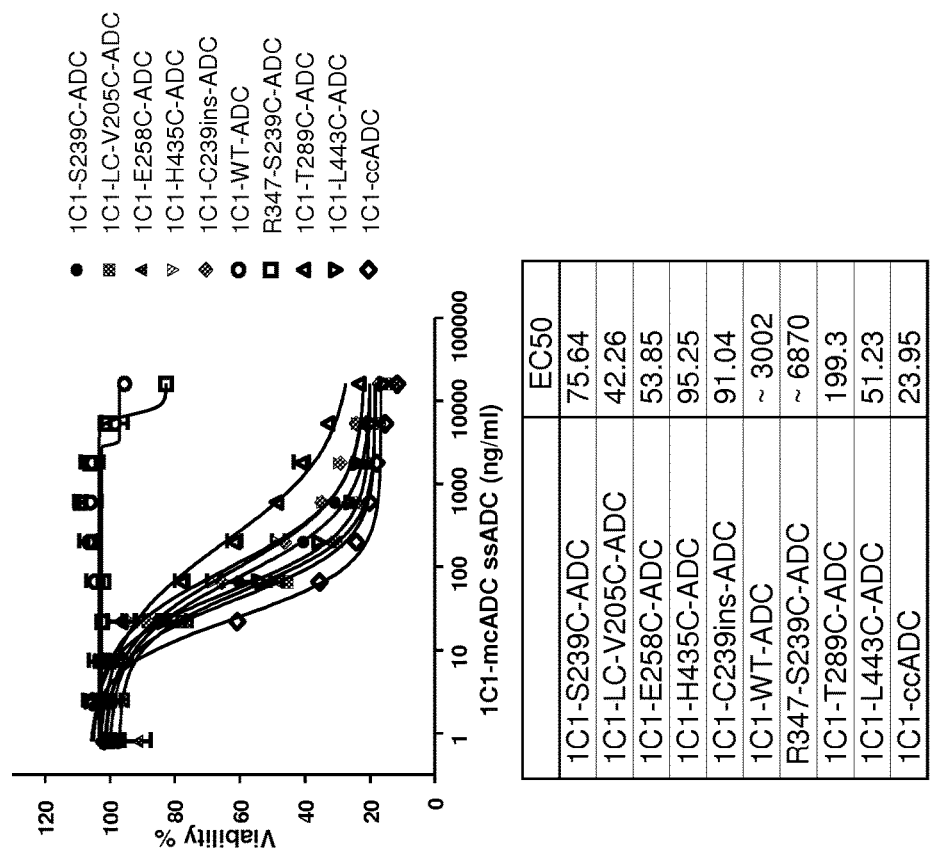

FIG. 13A-C shows cytotoxicity of the single Cys mutation antibody drug conjugates (ADCs) derived from the 1C1 antibody comprising an auristatin based cytotoxic drug on DU145 cells. Plotted are the cytoxicity curves for 1C1-S239C-ADC, 1C1-LC-V205C-ADC, 1C1-E258C-ADC, C1-H435C-ADC, 1C1-239ins-ADC, 1C1-T289C-ADC, 1C1-L443C-ADC, 1C1-ccADC (using a random conjugation approach) and the 1C1-WT-ADC (mock conjugation) and R347-S239C-ADC negative controls. Panel A shows the effect at day 0. Panel B shows the effect at day 3. Panel C shows the effect at day 7. Tables presenting the $EC_{50}$ values for each one of the curves are also shown.

Figure 14:
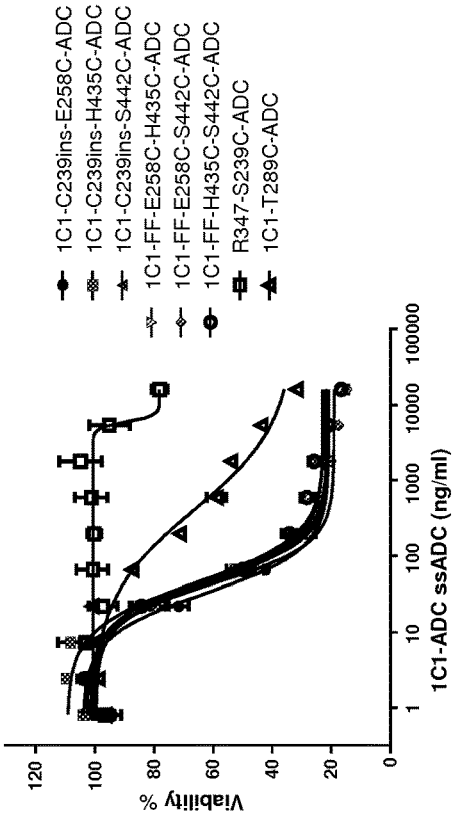
Figure 14:
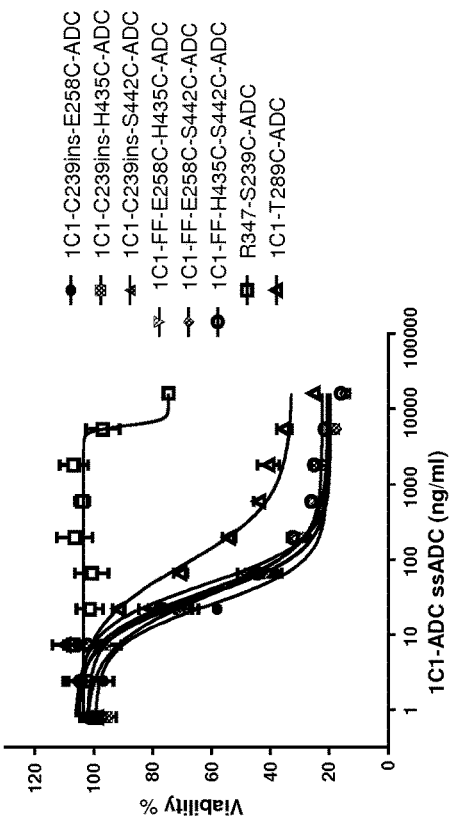
Figure 14:
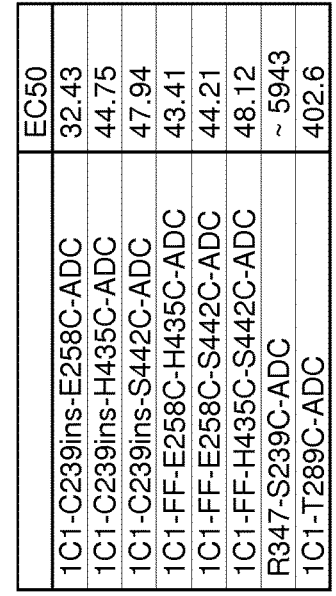
Figure 14:
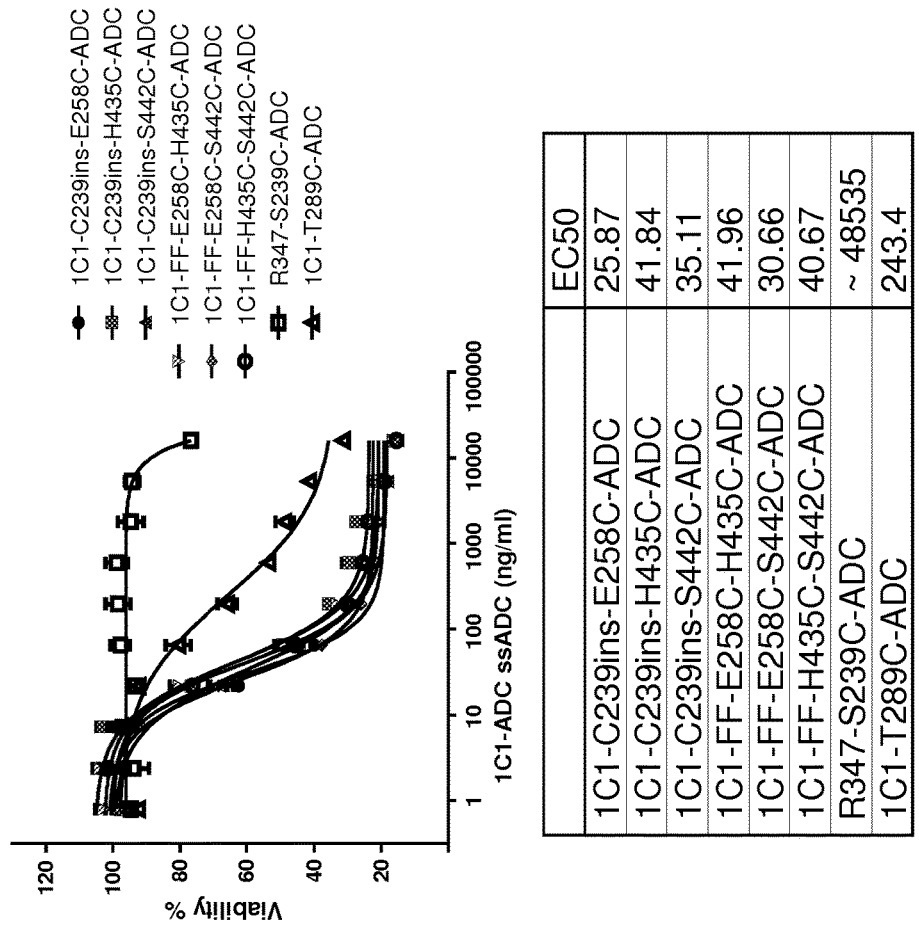

FIG. 14A-C shows cytotoxicity of ADCs derived from the 1C1 antibody comprising two engineered cysteines and an auristatin based cytotoxic drug on DU145 cells. Plotted are the cytotoxicity curves for 1C1-239ins-E258C-ADC, C1-239ins-H435C-ADC, 1C1-239ins-S442C-ADC, 1C1-FF-E258C-S435C-ADC, 1C1-FF-E258C-S442C-ADC, 1C1-FF-H435C-S442C-ADC (note that "FF" indicates this construct contains additional mutations EU L234F/L235F to ablate Fc-mediated effector function) and 1C1-T289C-ADC. Panel A shows the effect at day 0. Panel B shows the effect at day 3. Panel C shows the effect at day 7. Tables presenting the $EC_{50}$ values for each one of the curves are also shown.

DETAILED DESCRIPTION

The present disclosure provides conjugate compounds comprising cysteine-engineered antibodies and Fc fusion proteins wherein one or more amino acid residues have been substituted with reactive cysteine residues, and more specifically to conjugate compounds with therapeutic or diagnostic applications. The conjugate compounds disclosed herein comprise cysteine-engineered antibodies or Fc fusion proteins conjugated, for example, to chemotherapeutic drugs, toxins, radionuclides, and detection labels such as radionuclides or fluorophores. The disclosure also relates to methods of using the disclosed conjugate compounds for in vitro, in situ, ex vivo, and in vivo diagnosis or treatment of mammalian cells, or associated pathological conditions.

In order that the present disclosure can be more readily understood, certain terms are first defined. Additional definitions are set forth throughout the detailed description.

I. Definitions

Before describing the provided embodiments in detail, it is to be understood that this disclosure is not limited to specific compositions or process steps, and as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "antibody" or "immunoglobulin," as used interchangeably herein, include whole antibodies and any antigen binding fragment or single chains thereof.

A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three or four constant domains, CH1, CH2, CH3, CH4. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary cysteine-engineered antibodies of the present disclosure include typical antibodies, fusion proteins, and constructs comprising an antibody or an antigen-binding fragment thereof, for example, a construct comprising an Fc domain and an scFv covalently linked (for example, via peptidic bonds or via a chemical linker) to the N-terminus of a CH2 domain or the C-terminus of a CH3 domain of a heavy chain of a typical antibody.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc., to form Antibody Drug Conjugates (ADC).

The terms "antigen-binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FW) residues of a human immunoglobulin are replaced with the corresponding residues in an antibody from a non-human species that has the desired specificity, affinity, and capability.

The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are human. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g.,Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used herein the Fc region includes the polypeptides comprising the constant region of an antibody excluding the first constant region immunoglobulin domain, and fragments thereof. Thus Fc refers to the last two constant region immunoglobulin domains of IgA, IgD, and IgG, and the last three constant region immunoglobulin domains of IgE and IgM, and optionally the flexible hinge region N-terminal to these domains. For IgA and IgM the Fc region can include the J chain. For IgG, Fc comprises immunoglobulin domains Cgamma2 and Cgamma3 (Cγ2 and Cγ3) and optionally the hinge region between Cgamma1 (Cγ1) and Cgamma2 (Cγ2). Although the boundaries of the Fc region can vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc can refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

As used herein, the term "Fc fusion protein" encompasses proteins (e.g., conjugate compounds of the present disclosure) comprising a full length Fc domain as well as proteins comprising Fc domain fragments (e.g., a full CH2 domain, a full CH3 domain, a CH2 fragment, a CH3 fragment, or combinations thereof). An Fc fusion protein may also comprise all or a portion of the hinge region.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition that is "isolated" is a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition that is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" can be used interchangeably in reference to a human subject.

The term "pharmaceutical composition" refers to a preparation which is in such form as to permit the biological activity of the active ingredient (e.g., a conjugate compound disclosed herein) to be effective, and which contains no additional components which are unacceptably toxic to a subject to which the composition would be administered. Such composition may comprise one or more pharmaceutically acceptable excipients. Such composition can be sterile.

An "effective amount" of a conjugate compound as disclosed herein is an amount sufficient to carry out a specifically stated purpose. An "effective amount" can be determined empirically and in a routine manner, in relation to the stated purpose.

The term "therapeutically effective amount" refers to an amount of conjugate compound disclosed herein or other drug effective to "treat" a disease or disorder in a subject or mammal.

The word "label" when used herein refers to a detectable compound or composition which is conjugated directly or indirectly to an cysteine-engineered antibody or fragment thereof disclosed herein so as to generate a "labeled" conjugate compound. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for a disease or condition, for example, cancer, according to the methods of the present disclosure if the patient shows, e.g., total, partial, or transient remission of the disease or condition, for example, a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways can participate to different degrees in the pathology of autoimmune diseases. An autoimmune disease can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly produced polypeptides and proteins expressed in engineered host cells are considered isolated for the purpose of this disclosure, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. Substitution patterns can described according to the schema AXY, wherein A is the single letter code corresponding to the amino acid naturally present at position X, and A is the substituting amino acid residue. Accordingly, L234F would refer to the substitution of the leucine amino acid (L) at position 234 with a phenylalanine (F).

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrase "insertion between positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AX-ins, wherein A is the single letter code corresponding to the amino acid being inserted, and X is the position preceeding the insertion. Accordingly, C239ins would refer to the insertion of a cysteine amino acid (C) after position 239 (i.e., an insertion between position 239 and 240). The C239ins may also be referred to herein by the shorter abbreviation "239ins".

The terms "engineered cysteine" or "cysteine-engineered at position . . . " or grammatical variants thereof refer to a cysteine (C) amino acid that has been engineered into an antibody or part of an antibody (e.g., an Fc domain or a fragment thereof), and has a thiol functional group (—SH).

II. Conjugate Compounds Comprising Engineered Cysteines

The present disclosure provides conjugate compounds comprising a cysteine-engineered antibody or Fc fusion protein and at least one heterologous moiety, wherein (i) the Fc domain of the antibody or Fc fusion protein thereof comprises at least one engineered cysteine amino acid selected from cysteine amino acid substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, a cysteine amino acid insertion between positions 239 and 240, and combinations thereof, wherein the amino acid position numbering is according to the EU index as set forth in Kabat (1991, NIH Publication 91-3242, National Technical Information Service, Springfield, Va.); and (ii) wherein at least one heterologous moiety is conjugated to one of the engineered cysteines.

In some aspects, the engineered cysteine amino acid is selected from cysteine amino acid substitutions at amino acid positions 241, 243, 251, 253, 258, 264, 271, 285, 288, 291, 296, 301, 307, 309, 311, 329, 385, 387, 433, or 435, a cysteine amino acid insertion between positions 239 and 240, and combinations thereof.

In other aspects, the engineered cysteine amino acid is selected from cysteine amino acid substitutions at amino acid positions 258, or 435 a cysteine amino acid insertion between positions 239 and 240, and combinations thereof.

In some aspects, the conjugate compounds disclosed herein comprise at least one engineered cysteine amino acid at one or more positions disclosed herein (e.g., positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240), and optionally comprise additional engineered cysteines at additional positions suitable for cysteine-engineering described in the art including, but not limited to, positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446.

The sites suitable for cysteine engineering disclosed herein were identified on the exemplary antibody 1C1. These positions are located in the CH2 and CH3 domains of the antibody, which are domains well conserved across all species of antibodies. These sites should be broadly applicable to other antibodies, without further need of structural design or knowledge of specific antibody structures, and without interference in the antigen binding properties inherent to the variable domains of the antibody.

In some aspects, the conjugate compound comprises (i) an engineered cysteine amino acid at amino acid position 241 and (ii) a second engineered cysteine amino acid at amino acid position 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises an engineered cysteine amino acid at amino acid position 243 and a second engineered cysteine amino acid at amino acid position 241, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 251 and (ii) a second engineered cysteine amino acid at amino acid position 241, 243, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 253 and (ii) a second engineered cysteine amino acid at amino acid position 241, 243, 251, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 258 and (ii) a second engineered cysteine amino acid at amino acid position 241, 243, 251, 253, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 264 and (ii) a second engineered cysteine amino acid at amino acid position 241, 243, 251, 253, 258, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 269 and (ii) a second engineered cysteine amino acid at amino acid position 241, 243, 251, 253, 258, 264, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 271 and (ii) a second engineered cysteine amino acid at amino acid position 241, 243, 251, 253, 258, 264, 269, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 272 and (ii) a second engineered cysteine amino acid at amino acid position 241, 243, 251, 253, 258, 264, 269, 271, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 274 and (ii) a second engineered cysteine amino acid at amino acid position 241, 243, 251, 253, 258, 264, 269, 271, 272, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 280 and (ii) a second engineered cysteine amino acid at amino acid position 241, 243, 251, 253, 258, 264, 269, 271, 272, 274, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 281 and (ii) a second engineered cysteine amino acid at amino acid position 241, 243, 251, 253, 258, 264, 269, 271, 272, 274, 280, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 285 and (ii) a second engineered cysteine amino acid at amino acid position 241, 243, 251, 253, 258, 264, 269, 271, 272, 274, 280, 281, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 288 and (ii) a second engineered cysteine amino acid at amino acid position 241, 243, 251, 253, 258, 264, 269, 271, 272, 274, 280, 281, 285, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 291 and (ii) a second engineered cysteine amino acid at amino acid position 241, 243, 251, 253, 258, 264, 269, 271, 272, 274, 280, 281, 285, 288, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 293 and (ii) a second engineered cysteine amino acid at amino acid position 241, 243, 251, 253, 258, 264, 269, 271, 272, 274, 280, 281, 285, 288, 291, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 294 and (ii) a second engineered cysteine amino acid at amino acid position 241, 243, 251, 253, 258, 264, 269, 271, 272, 274, 280, 281, 285, 288, 291, 293, 296, 301, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 296 and (ii) a second engineered cysteine amino acid at amino acid position 241, 243, 251, 253, 258, 264, 269, 271, 272, 274, 280, 281, 285, 288, 291, 293, 294, 301, 307, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 301 and (ii) a second engineered cysteine amino acid at amino acid position 241, 243, 251, 253, 258, 264, 269, 271, 272, 274, 280, 281, 285, 288, 291, 293, 294, 296, 307, 309, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 307 and (ii) a second engineered cysteine amino acid at amino acid position 241, 243, 251, 253, 258, 264, 269, 271, 272, 274, 280, 281, 285, 288, 291, 293, 294, 296, 301, 309, 311, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 309 and (ii) a second engineered cysteine amino acid at amino acid position 241, 243, 251, 253, 258, 264, 269, 271, 272, 274, 280, 281, 285, 288, 291, 293, 294, 296, 301, 307, 311, 318, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 311 and (ii) a second engineered cysteine amino acid at amino acid position 241, 243, 251, 253, 258, 264, 269, 271, 272, 274, 280, 281, 285, 288, 291, 293, 294, 296, 301, 307, 309, 318, 329, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 318 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 329, 340, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 329 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 340, 341, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 340 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 341, 345, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 341 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 345, 357, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 345 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 357, 385, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 357 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 385, 386, 387, 401, 402, 411, 417, 433, 435, or 439, or a cysteine amino acid insertion between positions 239 and 240. In some aspects, the conjugate compound comprises (i) an engineered cysteine amino acid at amino acid position 385 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 386, 387, 401, 402, 411, 417, 433, 435, or 439, or a cysteine amino acid insertion between positions 239 and 240.

In some aspects, the conjugate compound comprises (i) an engineered cysteine amino acid at amino acid position 386 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 387, 401, 402, 411, 417, 433, 435, or 439, or a cysteine amino acid insertion between positions 239 and 240. In some aspects, the conjugate compound comprises (i) an engineered cysteine amino acid at amino acid position 387 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 401, 402, 411, 417, 433, 435, or 439, or a cysteine amino acid insertion between positions 239 and 240.

In some aspects, the conjugate compound comprises (i) an engineered cysteine amino acid at amino acid position 401 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 402, 411, 417, 433, 435, or 439, or a cysteine amino acid insertion between positions 239 and 240. In some aspects, the conjugate compound comprises (i) an engineered cysteine amino acid at amino acid position 402 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 411, 417, 433, 435, or 439, or a cysteine amino acid insertion between positions 239 and 240.

In some aspects, the conjugate compound comprises (i) an engineered cysteine amino acid at amino acid position 411 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 417, 433, 435, or 439, or a cysteine amino acid insertion between positions 239 and 240. In some aspects, the conjugate compound comprises (i) an engineered cysteine amino acid at amino acid position 417 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 433, 435, or 439, or a cysteine amino acid insertion between positions 239 and 240.

In some aspects, the conjugate compound comprises (i) an engineered cysteine amino acid at amino acid position 433 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 435, or 439, or a cysteine amino acid insertion between positions 239 and 240. In some aspects, the conjugate compound comprises (i) an engineered cysteine amino acid at amino acid position 435 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, or 439, or a cysteine amino acid insertion between positions 239 and 240.

In some aspects, the conjugate compound comprises (i) an engineered cysteine amino acid at amino acid position 439 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, or 435, or a cysteine amino acid insertion between positions 239 and 240. In some aspects, the conjugate compound comprises (i) an engineered cysteine amino acid inserted between positions 239 and 240 and (ii) a second engineered cysteine amino acid at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439.

In some aspects, the conjugate compound comprises at least a cysteine-engineered in the CH2 and/or the CH3 domain of the Fc domain. In some aspects, the conjugate compound comprises
  (i) an engineered cysteine amino acid in a CH2 domain, or
  (ii) an engineered cysteine amino acid in a CH3 domain, or
  (iii) more than one engineered cysteine amino acid in a CH2 domain, or
  (iv) more than one engineered cysteine amino acid in a CH3 domain, or
  (v) an engineered cysteine amino acid in a CH2 domain and an engineered cysteine amino acid in a CH3 domain, or
  (vi) an engineered cysteine amino acid in a CH2 domain and more than one engineered cysteine amino acid in a CH3 domain, or
  (vii) more than one engineered cysteine amino acid in a CH2 domain and an engineered cysteine amino acid in a CH3 domain, or
  (viii) more than one engineered cysteine amino acid in a CH2 domain and more than one engineered cysteine amino acid in a CH3 domain,
  wherein the engineered cysteine amino acids are selected from:
  (i) cysteine amino acid substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, a cysteine amino acid insertion between positions 239 and 240; or, (ii) amino acid substitutions at amino acid positions 241, 243, 251, 253, 258, 264, 271, 285, 288, 291, 296, 301, 307, 309, 311, 329, 385, 387, 433, or 435, a cysteine amino acid insertion between positions 239 and 240; or, (iii) amino acid substitutions at amino acid positions 258, or 435, or a cysteine amino acid insertion between positions 239 and 240.

In some aspects, such more than one engineered cysteine amino acids are two, three, four, or five engineered cysteine amino acids. In some aspects, the engineered cysteine amino acids in the CH2 domain are at positions 241, 243, 251, 253, 258, 264, 269, 271, 272, 274, 280, 281, 285, 288, 291, 293, 294, 296, 301, 307, 309, 311, 318, 329, 340, or inserted between positions 239 and 240. In some aspects, the engineered cysteine amino acids in the CH2 domain are at positions 241, 243, 251, 253, 258, 264, 271, 285, 288, 291, 296, 301, 307, 309, 311, 329, or inserted between positions 239 and 240. In some aspects, the engineered cysteine amino acids in the CH2 domain are at positions 258, or inserted between positions 239 and 240. In some aspects, the engineered cysteine amino acids in the CH3 domain are at positions 341, 345, 357, 385, 386, 387, 401, 402, 411, 417, 433, 435, or 439. In some aspects, the engineered cysteine amino acids in the CH3 domain are at positions 385, 387, 433, or 435. In some aspects, the engineered cysteine amino acid in the CH3 domain is at position 435.

In some aspects, the conjugate compound disclosed herein comprises a cysteine amino acid substitution selected from the group consisting of F241C, F243C, L251C, I253C, S254C, E258C, V264C, P271C, E272C, K274C, Q274C, D280C, G281C, H285C, K288C, P291C, E293C, E294C, Y296C, F296C, R301C, T307C, L309C, V309C, Q311C, E318C, P329C, K340C, G341C, E345C, E357C, G385C, Q386C, P387C, D401C, G402C, T411C, W417C, H433C, H435C, R435C, K439C, a cysteine amino acid insertion between S239 and V240, and combinations thereof.

In some aspects, the conjugate compound disclosed herein comprises a cysteine amino acid substitution selected from the group consisting of F241C, F243C, L251C, I253C, E258C, V264C, P271C, H285C, K288C, P291C, Y296C, F296C, R301C, T307C, L309C, V309C, Q311C, P329C, G385C, P387C, H433C, H435C, a cysteine amino insertion between S239 and V240, and combinations thereof.

In some aspects, the conjugate compound disclosed herein comprises an Fc domain comprising at least one engineered cysteine in a CH2 domain selected from amino acid substitutions F241C, F243C, L251C, I253C, S254C, E258C, V264C, P271C, E272C, K274C, Q274C, D280C, G281C, H285C, K288C, P291C, E293C, E294C, Y296C, R301C, T307C, L309C, V309C, Q311C, E318C, P329C, K340C, cysteine amino acid insertion between S239 and V240, and combinations thereof.

In some aspects, the conjugate compound disclosed herein comprises an Fc domain comprising at least one engineered cysteine in a CH3 domain selected from amino acid substitutions G341C, E345C, E357C, G385C, Q386C, P387C, D401C, G402C, T411C, W417C, H433C, H435C, R435C, K439C, and combinations thereof.

In some aspects, the conjugate compound disclosed herein comprises an Fc domain comprising at least one engineered cysteine in a CH2 domain selected from amino acid substitutions F241C, F243C, L251C, I253C, E258C, V264C, P271C, H285C, K288C, P291C, Y296C, R301C, T307C, L309C, Q311C, P329CC, cysteine amino acid insertion between S239 and V240, and combinations thereof. In some aspects, the conjugate compound disclosed herein comprises an Fc domain comprising at least one engineered cysteine in a CH3 domain selected from amino acid substitutions G385C, P387C, H433C, H435C, and combinations thereof.

In particular aspects, the conjugate compounds disclosed herein comprise an Fc domain comprising:

(a) a Cysteine (C) inserted between the Serine (S) located at position 239 and the Valine (V) located at position 240;

(b) a Cysteine (C) substituting the Glutamic acid (E) located at position 258;

(c) a Cysteine (C) substituting the Histidine (H) located at position 435;

(d) a Cysteine (C) substituting the Arginine (R) located at position 435; or, (e) a combination thereof, wherein the amino acid position numbering is according to the EU index as set forth in Kabat.

A person skilled in the art would understand that due to the existence of allelic variants, different amino acids in the EU positions disclosed herein can be replaced with cysteines. For example, in some aspects, a Cysteine (C) can substitute the Arginine (R) located at position 435 in the parent antibody or fragment thereof when such parent antibody is an IgG3.

In some aspects, the conjugate compounds disclosed herein comprise one engineered cysteine selected from the group consisting of insertion at position 241, 243, 251, 253, 258, 264, 271, 285, 288, 291, 296, 301, 307, 309, 311, 329, 385, 387, 433, or 435, or a cysteine amino acid insertion between positions 239 and 240, wherein the amino acid position numbering is according to the EU index as set forth in Kabat. In some aspects, the conjugate compound disclosed herein comprises one engineered cysteine selected from the group consisting of insertion at position 258, 435, or a cysteine amino acid insertion between positions 239 and 240, wherein the amino acid position numbering is according to the EU index as set forth in Kabat.

In some aspects, the conjugate compound disclosed herein comprises two engineered cysteines selected from the group consisting of insertion at position 241, 243, 251, 253, 258, 264, 271, 285, 288, 291, 296, 301, 307, 309, 311, 329, 385, 387, 433, or 435, or a cysteine amino acid insertion between positions 239 and 240, wherein the amino acid position numbering is according to the EU index as set forth in Kabat. In some aspects, the conjugate compound disclosed herein comprises two engineered cysteines selected from the group consisting of insertion at position 258, 435, or a cysteine amino acid insertion between positions 239 and 240, wherein the amino acid position numbering is according to the EU index as set forth in Kabat.

In some aspects, the conjugate compound disclosed herein comprises three engineered cysteines selected from the group consisting of insertion at position 241, 243, 251, 253, 258, 264, 271, 285, 288, 291, 296, 301, 307, 309, 311, 329, 385, 387, 433, or 435, or a cysteine amino acid insertion between positions 239 and 240, wherein the amino acid position numbering is according to the EU index as set forth in Kabat. In some aspects, the conjugate compound disclosed herein comprises three engineered cysteines selected from the group consisting of insertion at position 258, 435, or a cysteine amino acid insertion between positions 239 and 240, wherein the amino acid position numbering is according to the EU index as set forth in Kabat.

In some aspects, the conjugate compound disclosed herein comprises four engineered cysteine selected from the group consisting of insertion at position 241, 243, 251, 253, 258, 264, 271, 285, 288, 291, 296, 301, 307, 309, 311, 329, 385, 387, 433, or 435, or a cysteine amino acid insertion between positions 239 and 240, wherein the amino acid position numbering is according to the EU index as set forth in Kabat. In some aspects, the conjugate compound disclosed herein comprises four engineered cysteine selected from the group consisting of insertion at position 258, 435, or a cysteine amino acid insertion between positions 239 and 240, wherein the amino acid position numbering is according to the EU index as set forth in Kabat.

In some aspects, the conjugate compound comprises one engineered cysteine at position 258 and a second cysteine-engineered at position 435. In some aspects, the conjugate compound comprises one engineered cysteine at position 258 and a second cysteine-engineered at position 442. In some aspects, the conjugate compound comprises one engineered cysteine at position 435 and a second cysteine-engineered at position 442. In some aspects, the conjugate compound comprises one engineered cysteine at position 258 and a second cysteine-engineered between positions 239 and 240. In some aspects, the conjugate compound comprises one engineered cysteine at position 435 and a second cysteine-engineered between positions 239 and 240. In some aspects, the conjugate compound comprises one engineered cysteine at position 442 and a second cysteine-engineered between positions 239 and 240. In some aspects, the conjugate compound comprises three engineered cysteines at positions 258, 435, and 442. In other aspects, the conjugate compound comprises two engineered cysteines at positions 258, 435, and a third cysteine-engineered between positions 239 and 240. In other aspects, the conjugate compound comprises two engineered cysteines at positions 258 and 442 and a third cysteine-engineered between positions 239 and 240. In other aspects, the conjugate compound comprises two engineered cysteines at positions 435 and 442 and a third cysteine-engineered between positions 239 and 240. In some aspects, the conjugate compound comprises three engineered cysteines at positions 258, 435, and 442 and a fourth cysteine-engineered between positions 239 and 240.

In some specific aspects, the conjugate compound comprises a cysteine-engineered antibody comprising a pair or a trio of engineered cysteines selected from:
  (i) a cysteine amino acid substitution at position 258 of the parent antibody, and a cysteine amino acid insertion between positions 239 and 240 of the parent antibody;
  (ii) a cysteine amino acid substitution at position 289 of the parent antibody, and a cysteine amino acid insertion between positions 239 and 240 of the parent antibody;
  (iii) a cysteine amino acid substitution at position 339 of the parent antibody, and a cysteine amino acid insertion between positions 239 and 240 of the parent antibody;
  (iv) a cysteine amino acid substitution at positions 435 of the parent antibody, and a cysteine amino acid insertion between positions 239 and 240 of the parent antibody;
  (v) a cysteine amino acid substitution at position 442 of the parent antibody, and a cysteine amino acid insertion between positions 239 and 240 of the parent antibody;
  (vi) a first cysteine amino acid substitution at position 258 of the parent antibody, and a second cysteine amino acid substitution at position 289 of the parent antibody;
  (vii) a first cysteine amino acid substitution at position 258 of the parent antibody, and a second cysteine amino acid substitution at position 339 of the parent antibody;
  (viii) a first cysteine amino acid substitution at position 258 of the parent antibody, and a second cysteine amino acid substitution at position 435 of the parent antibody;
  (ix) a first cysteine amino acid substitution at position 258 of the parent antibody, and a second cysteine amino acid substitution at position 442 of the parent antibody;
  (x) a first cysteine amino acid substitution at position 435 of the parent antibody, and a second cysteine amino acid substitution at position 289 of the parent antibody;
  (xi) a first cysteine amino acid substitution at position 435 of the parent antibody, and a second cysteine amino acid substitution at position 339 of the parent antibody;
  (xii) a first cysteine amino acid substitution at position 435 of the parent antibody, and a second cysteine amino acid substitution at position 442 of the parent antibody;
  (xiii) a cysteine amino acid substitution at positions 258 and 289 of the parent antibody, and a cysteine amino acid insertion between positions 239 and 240 of the parent antibody;
  (xiv) a cysteine amino acid substitution at positions 258 and 339 of the parent antibody, and a cysteine amino acid insertion between positions 239 and 240 of the parent antibody;
  (xv) a cysteine amino acid substitution at positions 258 and 435 of the parent antibody, and a cysteine amino acid insertion between positions 239 and 240 of the parent antibody;
  (xvi) a cysteine amino acid substitution at positions 258 and 442 of the parent antibody, and a cysteine amino acid insertion between positions 239 and 240 of the parent antibody;
  (xvii) a cysteine amino acid substitution at positions 289 and 339 of the parent antibody, and a cysteine amino acid insertion between positions 239 and 240 of the parent antibody;
  (xviii) a cysteine amino acid substitution at positions 339 and 435 of the parent antibody, and a cysteine amino acid insertion between positions 239 and 240 of the parent antibody; and
  (xix) a cysteine amino acid substitution at positions 435 and 442 of the parent antibody, and a cysteine amino acid insertion between positions 239 and 240 of the parent antibody;
wherein the amino acid position numbering is according to the EU index as set forth in Kabat.

A person skilled in the art would understand that in some aspects, engineering of a single cysteine residue at a certain position often results in the display of two cysteine residues at such position in the resultant antibody or Fc Fusion protein due to the homodimeric nature of molecules comprising an Fc region. In some aspects the Fc regions of a conjugate compound may be differentially engineered with mutations to: promote and/or maintain heterodimerization (e.g., chimeric mutations, complementary mutations, lock and dock mutations, knobs into holes mutations, strand-exchange engineered domain (SEED) mutations, etc.); alter half-life (e.g., enhance FcRn binding). Accordingly, a conjugate compound can be engineered to form a heterodimer comprising for example one cysteine-engineered in one Fc region or fragment thereof at a certain position disclosed herein (e.g., a cysteine at position 258), and one cysteine-engineered in the second Fc region or fragment at a different position disclosed herein (e.g., a cysteine-engineered at position 435). The same would be applicable to aspects in which the Fc region comprises two, three or four cysteines engineered at the specific positions disclosed herein. Similarly, both Fc regions can comprise a different number of engineered cysteines at the specific positions disclosed herein, for example, one Fc region can comprise one, two, three or four engineered cysteines, whereas the second Fc region can comprise no engineered cysteines, or one, two, three or four cysteines engineered at the specific positions disclosed herein.

The engineered cysteines disclosed herein introduce thiol groups that can be used for derivatization with a variety of heterologous molecules (e.g., to generate diagnostics reagents, to produce antibody drug conjugates, to add moieties that can be improve the bioavailability of the parent antibody, or to add different antigen binding moieties to generate for example bispecific antibodies). Accordingly, the engineering of one or more cysteines in the EU positions disclosed above can result in compounds with one or more heterologous molecules occupying all the introduced thiol groups, or conjugate compounds in which one of more thiol groups are available for additional conjugations. Thus, is some aspects, the conjugate compounds comprise at least one, at least two, at least three, at least four, at least five, at least six, at least seven, at least eight, at least nine, at least ten, at least 11, at least 12, at least 13, at least 14, at least 15, or at least 16 thiol groups for the purpose of conjugation to a heterologous molecule. In some aspects, the conjugate compound comprises more than 16 thiol groups for the purpose of conjugation to a heterologous molecule.

In some aspects, 1, 2, 3, or 4 cysteine amino acids are engineered at the EU positions indicated in FIGS. 1 and 2. In some aspects, other cysteines can be engineered at additional EU positions suitable for cysteine-engineered described in the art. In some aspects, other amino acids can be modified at additional EU positions disclosed in the art. Accordingly, in some aspects the conjugate compounds disclosed herein further comprise at least one engineered cysteine residue selected from cysteine amino acid substitutions at amino acid positions 239, 248, 254, 273, 279, 282, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446.

Any form of an antibody or fragment thereof comprising a CH2 and/or CH3 domain can be engineered as disclosed herein, i.e., it can be mutated. For example, a parent Fc antibody fragment can be engineered to form a cysteine-engineered Fc fragment. Similarly, a parent monoclonal antibody can be cysteine-engineered as disclosed herein. The design, selection, and preparation methods disclosed herein and methods known in the art enable the production of antibodies with cysteines engineered at the EU positions disclosed herein, and further enable conjugate compounds such as antibody-drug conjugate (ADC) compounds with drug molecules at designated, designed, selective sites. The engineered cysteine residues allow specifically conjugating a heterologous moiety, for example, a drug moiety, through a thiol reactive group such as maleimide or haloacetyl.

Accordingly, the present disclosure provides a method for making a conjugate compound comprising reacting at least one engineered cysteine group of a cysteine-engineered antibody or Fc fusion protein with a heterologous moiety, wherein the Fc domain of the antibody or Fc fusion protein comprises at least one engineered cysteine amino acid selected from cysteine amino acid substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, a cysteine amino acid insertion between positions 239 and 240, and combinations thereof, wherein the amino acid position numbering is according to the EU index as set forth in Kabat. In some aspects, the engineered cysteine amino acid is selected from cysteine amino acid substitutions at amino acid positions 241, 243, 251, 253, 258, 264, 271, 285, 288, 291, 296, 301, 307, 309, 311, 329, 385, 387, 433, or 435, a cysteine amino acid insertion between positions 239 and 240, and combinations thereof. In other aspects, the engineered cysteine amino acid is selected from cysteine amino acid substitutions at amino acid positions 258, or 435, a cysteine amino acid insertion between positions 239 and 240, and combinations thereof.

In some aspects, the conjugation efficiency at an engineered cysteine at an amino acid position selected from 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, 439, and a cysteine amino acid insertion between positions 239 and 240, wherein the amino acid position numbering is according to the EU index as set forth in Kabat, is at least about 40%, at least about 45%, at least about 50%, at least 55%, at least about 60%, at least about 65%, at least about 70%, at least about 75%, at least about 80%, at least about 85%, at least 90%, at least about 95%, or at least about 100% of that obtained when reacting an engineered cysteine group of a comparable cysteine-engineered antibody or Fc fusion protein with a heterologous moiety having a cysteine amino acid substitution at amino acid position 289, wherein the amino acid position numbering is according to the EU index as set forth in Kabat.

In some aspects, the conjugation efficiency is at least 50% of that obtained when reacting an engineered cysteine group of a comparable cysteine-engineered antibody or Fc fusion protein with a heterologous moiety having a cysteine amino acid substitution at amino acid position 289, wherein the amino acid position numbering is according to the EU index as set forth in Kabat. In some aspects, the conjugation efficiency is at least 80% of that obtained when reacting an engineered cysteine group of a comparable cysteine-engineered antibody or Fc fusion protein with a heterologous moiety having a cysteine amino acid substitution at amino acid position 289, wherein the amino acid position numbering is according to the EU index as set forth in Kabat. In other aspects, the conjugation efficiency is more than 100% of that obtained when reacting an engineered cysteine group of a comparable cysteine-engineered antibody or Fc fusion protein with a heterologous moiety having a cysteine amino acid substitution at amino acid position 289, wherein the amino acid position numbering is according to the EU index as set forth in Kabat.

In certain aspects, the conjugate compounds disclosed here can be made according to the following general process:
(i) mutagenizing, e.g., by site-directed mutagenesis, at least a nucleic acid sequence encoding an antibody or Fc fusion protein by
(a) replacing at least a codon at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, with a codon encoding for a cysteine (C) amino acid or inserting a codon encoding for a cysteine (C) between the codons encoding the amino acids at positions 239 and 240, wherein the amino acid position numbering is according to the EU index as set forth in Kabat; or
(b) replacing at least a codon at amino acid position 241, 243, 251, 253, 258, 264, 271, 285, 288, 291, 296, 301, 307, 309, 311, 329, 385, 387, 433, or 435, with a codon encoding for a cysteine (C) amino acid or inserting a codon encoding for a cysteine (C) between the codons encoding the amino acids at positions 239 and 240, wherein the amino acid position numbering is according to the EU index as set forth in Kabat; or, (c) replacing at least a codon at amino acid position 258, or 435, with a codon encoding for a cysteine (C) amino acid or inserting a codon encoding for a cysteine (C) between the codons encoding the amino acids at positions 239 and 240, wherein the amino acid position numbering is according to the EU index as set forth in Kabat;

(ii) expressing the cysteine-engineered antibody or Fc fusion protein;

(iii) isolating the cysteine-engineered antibody or Fc fusion protein; and (iv) reacting at least one engineered cysteine group of the cysteine-engineered antibody or Fc fusion protein with a heterologous moiety.

In certain aspects, the conjugate compounds disclosed here can be made according to the following general process:

(i) operably linking a nucleic acid sequence encoding a variable heavy chain region or a heterologous protein to a nucleic acid sequence encoding an Fc region protein, wherein the nucleic acid sequence encoding the Fc region protein comprises:

(a) at least a codon encoding a cysteine at amino acid position 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or inserted between the codons encoding the amino acid at positions 239 and 240, wherein the amino acid position numbering is according to the EU index as set forth in Kabat; or (b) at least a codon encoding a cysteine at amino acid at position 241, 243, 251, 253, 258, 264, 271, 285, 288, 291, 296, 301, 307, 309, 311, 329, 385, 387, 433, or 435, or inserted between the codons encoding the amino acids at positions 239 and 240, wherein the amino acid position numbering is according to the EU index as set forth in Kabat; or, (c) at least a codon encoding a cysteine at amino acid position 258, or 435, or inserted between the codons encoding the amino acids at positions 239 and 240, wherein the amino acid position numbering is according to the EU index as set forth in Kabat;

(ii) expressing the cysteine-engineered antibody or Fc fusion protein;

(iii) isolating the cysteine-engineered antibody or Fc fusion protein; and (iv) reacting at least one engineered cysteine group of the cysteine-engineered antibody or Fc fusion protein with a heterologous moiety.

In some aspects, about 25%, about 30%, about 35%, about 40%, about 45%, about 50%, about 55%, about 60%, about 65%, about 70%, about 75%, about 80%, about 85%, or about 95% of the heterologous moiety chemically conjugated to an engineered cysteine at an amino acid position selected from 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, 439, and a cysteine amino acid insertion between positions 239 and 240, wherein the amino acid position numbering is according to the EU index as set forth in Kabat, is intact after 3 days of serum incubation. In some aspects, at least 70% of the heterologous moiety chemically conjugated is intact after 3 days of serum incubation. In some aspects, about 25%, about 30%, about 35%, about 40%, about 45%, about 50%, about 55%, about 60%, about 65%, about 70%, about 75%, about 80%, about 85%, or about 95% of the heterologous moiety chemically conjugated is intact after 7 days of serum incubation. In other aspects, at least 70% of the heterologous moiety chemically conjugated is intact after 7 days of serum incubation.

In some aspects, about 25%, about 30%, about 35%, about 40%, about 45%, about 50%, about 55%, about 60%, about 65%, about 70%, about 75%, about 80%, about 85%, or about 95% of the heterologous moiety chemically conjugated to an engineered cysteine at an amino acid position selected from 258, 435 and a cysteine amino acid insertion between positions 239 and 240, wherein the amino acid position numbering is according to the EU index as set forth in Kabat, is intact after 3 days of serum incubation. In some aspects, at least 70% of the heterologous moiety chemically conjugated is intact after 3 days of serum incubation. In some aspects, about 25%, about 30%, about 35%, about 40%, about 45%, about 50%, about 55%, about 60%, about 65%, about 70%, about 75%, about 80%, about 85%, or about 95% of the heterologous moiety chemically conjugated is intact after 7 days of serum incubation. In other aspects, at least 70% of the heterologous moiety chemically conjugated is intact after 7 days of serum incubation.

In some aspects, the conjugate compounds comprising a heterologous moiety chemically conjugated to an engineered cysteine at an amino acid position selected from 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, 439, and a cysteine amino acid insertion between positions 239 and 240, wherein the amino acid position numbering is according to the EU index as set forth in Kabat, exhibit an activity loss of less than about 5%, about 10%, about 20%, about 25%, about 30%, about 35%, about 40%, about 45%, or about 50% over a 3 day period when incubated with serum. In some aspects, the conjugate compounds exhibit an activity loss of less than about 5%, about 10%, about 20%, about 25%, about 30%, about 35%, about 40%, about 45%, or about 50% over a 7 day period when incubated with serum. In other aspects, the conjugate compounds exhibit an activity loss of less than about 50% over a 7 day period when incubated with serum.

In some aspects, the conjugate compounds comprising a heterologous moiety chemically conjugated to an engineered cysteine at an amino acid position selected from 258, 435 and a cysteine amino acid insertion between positions 239 and 240, wherein the amino acid position numbering is according to the EU index as set forth in Kabat, exhibit an activity loss of less than about 5%, about 10%, about 20%, about 25%, about 30%, about 35%, about 40%, about 45%, or about 50% over a 3 day period when incubated with serum. In some aspects, the conjugate compounds exhibit an activity loss of less than about 5%, about 10%, about 20%, about 25%, about 30%, about 35%, about 40%, about 45%, or about 50% over a 7 day period when incubated with serum. In other aspects, the conjugate compounds exhibit an activity loss of less than about 50% over a 7 day period when incubated with serum.

In some aspects, the conjugate compounds disclosed herein comprise at least one heterologous moiety chemically conjugated to an engineered cysteine. In other aspects, the conjugate compound comprises at least two, at least three, or at least 4 heterologous moieties, wherein at least one heterologous moiety is conjugated to an engineered cysteine. In other aspects, the conjugate compound comprises at least two, at least three, or at least 4 heterologous moieties, wherein each one of the heterologous moieties is conjugated to an engineered cysteine. In some aspects, the conjugate compound comprises at least 6, 8, 10, 12, 14, 16 or more heterologous moieties, wherein at least one heterologous moiety is conjugated to an engineered cysteine. In some aspects, the conjugate compound comprises at least 6, 8, 10, 12, 14, 16 or more heterologous moieties, wherein each one the heterologous moieties is conjugated to an engineered cysteine. In certain aspects, all the heterologous moieties are identical. In other aspects, at least one heterologous moiety is different from the rest.

In some aspects, the Fc domain of the cysteine-engineered antibody or Fc fusion protein is part of a monoclonal antibody, a bispecific antibody, a multispecific antibody, a chimeric antibody, a human antibody, or a humanized antibody.

In some aspects, the Fc domain of the cysteine-engineered antibody or Fc fusion protein is an IgG Fc domain or a fragment thereof. In some aspects, such IgG Fc domain or a fragment thereof is human. In some aspects, the IgG is an human IgG1, IgG2, IgG3 or IgG4 isotype or a fragment thereof. In some aspects, the Fc domain of the cysteine-engineered antibody or Fc fusion protein does not include a full-length CH2. In other aspects, the Fc domain of the cysteine-engineered antibody or Fc fusion protein does not include a full-length CH3 domain and/or full-length CH4 domain. In some aspects, the Fc fusion protein comprises a polypeptide which mediates binding to a target. For example, the Fc fusion protein can comprise an antigen binding domain selected from the group consisting of (a) an scFv; (b) a diabody; (c) an Fd fragment; (d) an Fv fragment; (e) a TANDAB®; (f) a F(ab')$_2$ fragment; (g) a FCAB™, and (h) a F(ab) fragment.

In some aspects, the cysteine-engineered antibody or Fc fusion protein can comprise a Fab, a Fab', a F(ab')$_2$, a Fd, a single chain Fv or scFv, a disulfide linked Fv, a V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc.

In some aspects, the Fc fusion protein comprises a protein scaffold (e.g., a tenascin or fibronectic-derived scaffold) or antibody mimetic. In other aspects, the Fc fusion protein comprises a polypeptide selected from the group consisting of (a) a ligand, (b) an enzyme, (c) the ligand-binding portion of a receptor, and (d) an adhesion protein.

In other aspects, the Fc domain of the cysteine-engineered antibody or Fc fusion protein is a mutant Fc domain. Numerous mutations in the Fc domain have been described in the literature. For example, Fc domain mutations are described in PCT Publ. Nos. WO2012/064733, WO2013/093809, WO2008/070593, and WO1996/014339; U.S. Publ. Nos. US2007/0269369, US2007/0111260, and US2010/0297103; and U.S. Pat. No. 7,855,275, all of which are herein incorporated by reference in their entireties. In some aspects, the Fc domain of the cysteine-engineered antibody or Fc fusion protein comprises at least one non naturally occurring amino acid residue selected from the group consisting of 234D, 234E, 234N, 234Q, 234T, 234H, 234Y, 234I, 234V, 234F 235A, 235D, 235R, 235W, 235P, 235S, 235N, 235Q, 235T, 235H, 235Y, 235I, 235V, 235F, 236E, 239A, 239D, 239E, 239N, 239Q, 239F, 239T, 239H, 239Y, 240I, 240A, 240T, 240M, 241W, 241 L, 241Y 241 E, 241 R. 243W, 243L 243Y, 243R, 243Q, 244H, 245A, 247L, 247V, 247G, 251F, 252Y, 254T 255L, 256E, 256M, 262I, 262A, 262T, 262E, 263I, 263A, 263T, 263M, 264L, 264I, 264W, 264T 264R, 264F, 264M, 264Y, 264E, 265G, 265N, 265Q, 265Y, 265F, 265V, 265I, 265L, 265H, 265T 266I, 266A, 266T, 266M, 267Q, 267L, 269Y, 269F, 269R, 270E, 280A, 284M, 292P 292L, 296E, 296Q, 296D, 296N, 296S, 296T, 296L, 296I, 296H, 296G, 297S, 297D, 297E, 298H 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y, and 443W, wherein the amino acid position numbering is according to the EU index as set forth in Kabat.

In some aspects, the Fc domain of the cysteine-engineered antibody or Fc fusion protein has reduced binding to an Fc receptor to reduce cytotoxicity, e.g., via ADCC. In some aspects, the Fc domain of the cysteine-engineered antibody or Fc fusion protein has increased binding to an Fc receptor to increase cytotoxicity, e.g., via ADCC.

Certain modifications can provide desired effector functions or serum half-life. Where it is desirable to eliminate or reduce effector function, so as to minimize side effects or therapeutic complications, certain other Fc regions can be used. The Fc region of antibodies and Fc fusion proteins can be modified to increase the binding affinity for FcRn and thus increase serum half-life. Accordingly, in some aspects, the Fc domain of the cysteine-engineered antibody or Fc fusion protein has reduced binding to the Fc receptor FcRn.

In some aspects, the Fc domain of the cysteine-engineered antibody or Fc fusion protein comprises a non-naturally occurring ADCC reducing amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Numerous specific mutations capable of reducing the ADCC activity of an antibody are known in the art and include, for example 234F, 235E, 235F, 235Q (or 235Y), 239A, 332Q, 331S and combinations thereof. For example, see the mutations described in WO8807089, WO9958572, WO9951642, WO2012175751, WO2011149999, WO2011066501, WO2000042072, WO2011120134, which are herein incorporated by reference in their entireties. Antibodies with reduced ADCC effector function also include those with substitution of one or more of Fc region residues 238, 265, 269, 270, 297, 327 and 329 (U.S. Pat. No. 6,737,056). Such Fc mutants also include Fc mutants with substitutions at two or more of amino acid positions 265, 269, 270, 297 and 327, including Fc mutant with substitution of residues 265 and 297 to alanine (U.S. Pat. No. 7,332,581). Optionally, mutations which reduce both ADCC and CDC may be incorporated.

(a) Heterologous Moieties

The cysteine-engineered antibodies or Fc fusion proteins disclosed herein can be conjugated with any heterologous moiety which can be covalently attached to the cysteine-engineered antibody or Fc fusion protein through a reactive cysteine thiol group. In an exemplary aspect, a conjugate compound comprises a cysteine-engineered antibody or Fc fusion protein and a heterologous moiety, wherein the heterologous moiety is attached to the cysteine-engineered antibody or Fc fusion protein through one or more of the engineered cysteines. In some aspects, one or more linkers are interposed between the heterologous moiety and the cysteine-engineered antibody or Fc fusion protein. Accordingly, a conjugated compound of the present disclosure can be represented by the formula CEP-(L-H)p, wherein CEP is the Cysteine Engineered Protein (i.e., antibody or Fc fusion protein), L is a linker, H is a heterologous moiety, and p is 1, 2, 3, or 4. The number of heterologous moieties that can be conjugated via a thiol group of an engineered cysteine to a cysteine-engineered antibody or Fc fusion protein is limited by the number of cysteine residues that are introduced as disclosed herein. Accordingly, the previous formula refers to conjugate compounds wherein the cysteine-engineered antibody or Fc fusion protein comprises 1, 2, 3, or 4 engineered cysteine amino acids.

In some aspects, the conjugate compounds disclosed herein comprise at least one heterologous moiety conjugated at one of the engineered cysteines wherein such heterologous moiety is a toxin, drug, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, non-natural amino acid, peptide, lipid, carbohydrate, scaffolding molecule, fluorescent tag, visualization peptide, biotin, serum half-life extender, capture tag, chelating agent, solid support, or a combination thereof. The engineered cysteines disclosed herein can be conjugated with any heterologous moiety which can be covalently attached to the reactive cysteine thiol group (Singh et al. (2002) Anal. Biochem. 304:147-15: Harlow E. and Lane, D. (1999) Using Antibodies: A Laboratory Manual, Cold Springs Harbor Laboratory Press, Cold Spring Harbor, N.Y.: Lundbiad R. L. (1991) Chemical Reagents for Protein Modification, 2nd ed. CRC Press, Boca Raton, Fla.).

In some aspects, the conjugate compounds disclosed herein comprise at least one heterologous moiety conjugated at one of the engineered cysteines wherein such heterologous moiety is a drug. In some aspects, the drug is a nitrogen mustard, ethylenimine derivative, alkyl sulfonates, nitrosourea, gemcitabine, triazene, folic acid analog, anthracycline, taxane, COX-2 inhibitor, pyrimidine analog, purine analog, antibiotic, enzyme inhibitor, epipodophyllotoxin, platinum coordination complex, vinca alkaloid, substituted urea, methyl hydrazine derivative, adrenocortical suppressant, hormone antagonist, endostatin, taxol, camptothecin, SN-38, doxorubicin, doxorubicin analog, antimetabolite, alkylating agent, antimitotic, anti-angiogenic agent, tyrosine kinase inhibitor, mTOR inhibitor, heat shock protein (HSP90) inhibitor, proteosome inhibitor, HDAC inhibitor, pro-apoptotic agent, methotrexate, CPT-11, or a combination thereof, and wherein conjugation is at one of the engineered cysteines. In particular aspects, the drug is amifostine, cisplatin, dacarbazine, dactinomycin, mechlorethamine, streptozocin, cyclophosphamide, carmustine, lomustine, doxorubicin lipo, gemcitabine, daunorubicin, daunorubicin lipo, procarbazine, mitomycin, cytarabine, etoposide, methotrexate, 5-fluorouracil, vinblastine, vincristine, bleomycin, paclitaxel, docetaxel, aldesleukin, asparaginase, busulfan, carboplatin, cladribine, 10-hydroxy-7-ethyl-camptothecin (SN38), gefitinib, dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

In some aspects, the drug is an auristatin (U.S. Pat. Nos. 5,635,483; 5,780,588), for example, MMAE (monomethyl auristatin E) or MMAF (monomethyl auristatin F). In other aspects, the drug is a dolastatin or dolastatin peptidic analog or derivative. Dolastatins and auristatins have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. No. 5,663,149). The dolastatin or auristatin drug moiety can be attached to the conjugate compound through the N (amino) terminus or the C (carboxyl) terminus of the peptidic drug moiety (See, e.g., WO2002088172).

In other aspects, the drug is a maytansinoid. In some aspects, the maytansinoid is N 2'-deacetyl-N 2'-(3-mercapto-1-oxopropyl)-maytansine (DM1), N 2'-deacetyl-N2'-(4-mercapto-1-oxopentyl)-maytansine (DM3) or N 2'-deacetyl-N 2'(4-methyl-4-mercapto-1-oxopentyl)-maytansine (DM4). Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Conjugates containing maytansinoids, methods of making same, and their therapeutic use are disclosed, for example, in U.S. Pat. Nos. 5,208,020, 5,416,064 and European Patent EP0425235B1; Liu et al., Proc. Natl. Acad. Sci. USA 93:8618-8623 (1996) (described immunoconjugates comprising a maytansinoid designated DM1); and Chari et al., Cancer Research 52:127-131 (1992).

Maytansinoid conjugate compounds can be prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020. Exemplary maytansinoid drug moieties include those having a modified aromatic ring, such as: C-19-dechloro (U.S. Pat. No. 4,256,746) prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR), +/−dechloro (U.S. Pat. No. 4,294,757) (prepared by acylation using acyl chlorides), and those having modifications at other positions. Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

In some aspects, the drug is calicheamicin. The calicheamicin family of antibiotics is capable of producing double-stranded DNA breaks at sub-picomolar concentrations. For the preparation of conjugates of the calicheamicin family see, e.g., U.S. Pat. Nos. 5,712,374, 5,714,586, 5,739,116, 5,767,285, 5,770,701, 5,770,710, 5,773,001, 5,877,296. Structural analogues of calicheamicin that can be used include, but are not limited to, γ1I, α2I, α3I, N-acetyl-γH, PSAG and θ11 (Hinman et al., Cancer Research 53:3336-3342 (1993), Lode et al., Cancer Research 58:2925-2928 (1998) and the aforementioned U.S. patents to American Cyanamid).

In some aspects, the drug is tubulysin. Tubulysins are members of a class of natural products isolated from myxobacterial species (Sasse et al., J. Antibiot. 53:879-885 (2000)). As cytoskeleton interacting agents, tubulysins are mitotic poisons that inhibit tubulin polymerization and lead to cell cycle arrest and apoptosis (Steinmetz et al., Chem. Int. Ed. 43:4888-4892 (2004); Khalil et al., ChemBioChem. 7:678-683 (2006); Kaur et al., Biochem. J. 396: 235-242 (2006)). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling et al., Mol. Diversity 9:141-147 (2005)). These compounds show high cytotoxicity tested against a panel of cancer cell lines with $IC_{50}$ values in the low picomolar range; thus, they are of interest as anticancer therapeutics. See, e.g., WO2012019123, which is herein incorporated by reference in its entirety. Tubulysin conjugates are disclosed, e.g., in U.S. Pat. No. 7,776,814.

In some aspects, the drug is a pyrrolobenzodiazepine (PBD). PBDs are relatively small molecules and some have the ability to recognize and covalently bind to specific sequences in the minor groove of DNA and thus exhibit antibiotic/antitumor activity. A number of PBDs and derivatives thereof are known in the art, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274). PBDs are further described WO 2000/012507, WO 2007/039752, WO 2005/110423, WO 2005/085251, and WO 2005/040170, and U.S. Pat. No. 7,612,062, each of which is incorporated by reference herein in its entirety.

In some aspects, the conjugate compounds disclosed herein comprise at least one heterologous moiety conjugated at one of the engineered cysteines wherein such heterologous moiety is a toxin. In some aspects, the toxin comprises, for example, abrin, brucine, cicutoxin, diphteria toxin, botulinum toxin, shiga toxin, endotoxin, tetanus toxin, pertussis toxin, anthrax toxin, cholera toxin, falcarinol, alpha toxin, geldanamycin, gelonin, lotaustralin, ricin, strychnine, tetrodotoxin, saponin, ribonuclease (RNase), DNase I, *Staphylococcal* enterotoxin-A, pokeweed antiviral protein, *Pseudomonas* exotoxin, *Pseudomonas* endotoxin, or a combination thereof. In other aspects, the toxin comprises, for example, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, mitogellin, restrictocin, phenomycin, neomycin, tricothecenes, or a combination thereof. See, for example, WO1993/021232.

In some aspects, the conjugate compounds disclosed herein comprise at least one heterologous moiety conjugated at one of the engineered cysteines wherein such heterologous moiety is a chelating agent. In some aspects, the chelating agent is, for example, DTPA, EC, DMSA, EDTA, Cy-EDTA, EDTMP, DTPA, CyDTPA, Cy2DTPA, BOPTA, DTPA-MA, DTPA-BA, DTPMP, DOTA, TRITA, TETA, DOTMA, DOTA-MA, HP-DO3A, pNB-DOTA, DOTP, DOTMP, DOTEP, DOTPP, DOTBzP, DOTPME, HEDP, DTTP, an N3S triamidethiol, DADS, MAMA, DADT, an N2S4 diaminetetrathiol, an N2P2 dithiol-bisphosphine, a 6-hydrazinonicotinic acid, a propylene amine oxime, a tetraamine, a cyclam, or a combination thereof.

In some aspects, the conjugate compounds disclosed herein comprise at least one heterologous moiety conjugated at one of the engineered cysteines wherein such heterologous moiety is a radionuclide. In some aspects, the radionuclide is, for example, chromium ($^{51}$Cr), cobalt ($^{57}$Co), fluorine ($^{18}$F), gadolinium ($^{153}$Gd, $^{159}$Gd), germanium ($^{68}$Ge), holmium (166Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thalliumtin ($^{201}$Tl), tin ($^{113}$Su, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn), or a combination thereof. In some specific aspects, the radionuclide is attached to the conjugate compound by a chelating agent.

In some aspects, the conjugate compounds disclosed herein comprise at least one heterologous moiety conjugated at one of the engineered cysteines wherein such heterologous moiety is a serum half-life extender. In some specific aspects, the serum half-life extender comprises, for example, albumin, albumin binding polypeptide, PAS, the β subunit of the C-terminal peptide (CTP) of human chorionic gonadotropin, polyethylene glycol (PEG), hydroxyethyl starch (HES), XTEN, albumin-binding small molecules, or a combination thereof.

In some aspects, the conjugate compounds disclosed herein comprise at least one heterologous moiety conjugated at one of the engineered cysteines wherein such heterologous moiety is a visualization label. Visualization labels include, without limitation, a chromophore, a fluorophore, a fluorescent protein, a phosphorescent dye, a tandem dye, a particle, a hapten, an enzyme, a radioisotope, or a combination thereof.

In some aspects, the visualization label is a visualization peptide. In some aspects, the visualization peptide enables visualization or localization of the conjugate compound in vitro, in vivo, ex vivo, or any combination thereof. In some aspects, the visualization peptide is a biotin acceptor peptide, a lipoic acid acceptor peptide, a fluorescent protein, a cysteine-containing peptide for ligation of a biarsenical dye or for conjugating metastable technetium, a peptide for conjugating europium clathrates for fluorescence resonance energy transfer (FRET)-based proximity assays, or any combination thereof. In some aspects, the fluorescent protein is green fluorescent protein (GFP), red fluorescent protein (RFP), yellow fluorescent protein (YFP), enhanced green fluorescent protein (EGFP), enhanced yellow fluorescent protein (EYFP), or any combination thereof. In some aspects, the fluorescent protein is a phycobiliprotein or a derivative thereof. Fluorescent proteins, especially phycobiliprotein, are useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This can be effective for detecting a low quantity of a target in a sample where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorophore then emits at a wavelength farther from the fluorescent proteins than could have been obtained with only the fluorescent protein. A functional combination can be phycobiliproteins and sulforhodamine fluorophores, or sulfonated cyanine fluorophores as known in the art. The fluorophore sometimes functions as the energy donor and the fluorescent protein is the energy acceptor.

In other aspects, the biarsenical dye is 4',5'-bis(1,3,2-dithioarsolan-2-yl)fluorescein (FlAsH). In some aspects, the biotin acceptor peptide facilitates conjugation of avidin- and streptavidin-based reagents. In some aspects, the lipoic acid acceptor peptide facilitates conjugation of thiol-reactive probes to bound lipoic acid or direct ligation of fluorescent lipoic acid analogs.

In some aspects, the conjugate compounds disclosed herein comprise at least one heterologous moiety conjugated at one of the engineered cysteines wherein such heterologous moiety is a fluorescent tag. In some aspects, the fluorescent tag comprises a fluorescein-type dye, a rhodamine-type dye, dansyl-type dye, a lissamine-type dye, a cyanine-type dye, a phycoerythrin-type dye, a Texas Red-type dye, or any combination thereof. Fluorophores suitable for conjugation to the cysteine-engineered antibodies or Fc fusion proteins disclosed herein include, without limitation; a pyrene (including any of the corresponding derivative compounds), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds), a carbocyanine (including any corresponding compounds), a carbostyryl, a porphyrin, a salicylate, an anthranilate, an azulene, a perylene, a pyridine, a quinoline, a borapolyazaindacene (including any coresponding compounds), a xanthene (including any corresponding compounds), an oxazine (including any corresponding compounds) or a benzoxazine, a carbazine (including any conesponding compounds), a phenalenone, a coumarin (including an conesponding compounds disclosed), a benzofuran (including an conesponding compounds) and benzphenalenone (including any conesponding compounds) and derivatives thereof. As used herein, oxazines include resorufins (including any corresponding compounds), aminooxazinones, diaminooxazines, and their benzo-substituted analogs, or any combination thereof.

In certain aspects, the fluorophores conjugated to cysteine-engineered antibodies or Fc fusion proteins disclosed herein include xanthene (rhodol, rhodamine, fluorescein and derivatives thereof) coumarin, cyanine, pyrene, oxazine, borapolyazaindacene, or any combination thereof. In some embodiments, such fluorophores are sulfonated xanthenes, fluorinated xanthenes, sulfonated coumarins, fluorinated coumarins, sulfonated cyanines, or any combination thereof. Also included are dyes sold under the tradenames, and generally known as, ALEXA FLUOR®, DYLIGHT®, CY DYES®, BODIPY®, OREGON GREEN®, PACIFIC BLUE®, IRDYEs®, FAM®, FITC®, and ROX®.

The choice of the fluorophore attached to cysteine-engineered antibodies or Fc fusion proteins disclosed herein will determine the absorption and fluorescence emission properties of the conjugate compound. Physical properties of a fluorophore label that can be used include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain aspects, the fluorophore has an absorption maximum at wavelengths greater than 480 nm. In some aspects, the fluorophore absorbs at or near 488 nm to 514 nm (particularly suitable for excitation by the output of the argon-ion laser excitation source) or near 546 nm (particularly suitable for excitation by a mercury arc lamp). In some aspects. a fluorophore can emit in the NIR (near infrared region) for tissue or whole organism applications. Other desirable properties of the fluorescent label can include cell permeability and low toxicity, for example if labeling of the antibody is to be performed in a cell or an organism (e.g., a living animal). In some specific aspects, the fluorescent tag is Alexa Fluor 488 C5-maleimide.

In some aspects, the conjugate compounds disclosed herein comprise at least one heterologous moiety conjugated at one of the engineered cysteines wherein such heterologous moiety is a capture tag. In some aspects, the capture tag is biotin or a His6 tag. Biotin is useful because it can function in an enzyme system to further amplify a detectable signal, and it can also function as a tag to be used in affinity chromatography for isolation purposes. For detection purposes, an enzyme conjugate that has affinity for biotin can be used, such as avidin-HRP. Subsequently a peroxidase substrate can be added to produce a detectable signal. In addition to biotin, other haptens can be used, including hormones, naturally occurring and synthetic drugs, pollutants, allergens, effector molecules, growth factors, chemokines, cytokines, lymphokines, amino acids, peptides, chemical intermediates, nucleotides and the like.

In some aspects, the conjugate compounds disclosed herein comprise at least one heterologous moiety conjugated at one of the engineered cysteines wherein such heterologous moiety is an enzyme. Enzymes are effective labels because amplification of the detectable signal can be obtained resulting in increased assay sensitivity. The enzyme itself often does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the measurable product, e.g., colorimetric, fluorescent or chemiluminescence. Such substrates are extensively used in the art and are known in the art.

In some embodiments, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants and reduced dihydroxanthenes, including dihydrofluoresceins and dihydrorhodamines including dihydrorhodamine 123. Peroxidase substrates that are tyramides represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

A colorimetric (and in some cases fluorogenic) substrate and enzyme combination sometimes uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In some embodiments, fluorogenic substrates include resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside and fluorinated coumarin beta-D-galactopyrano sides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are useful for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally productive.

In some aspects, the conjugate compounds disclosed herein comprise at least one heterologous moiety conjugated at one of the engineered cysteines wherein such heterologous moiety is a nucleic acid. The nucleic acid can be selected from the group consisting of DNA, RNA, short interfering RNA (siRNA), microRNA, hairpin or nucleic acid mimetics such as peptide nucleic acids. In certain aspects, the conjugated nucleic acid is at least 10, at least 20, at least 30, at least 40, at least 50, at least 60 at least 100, at least 200, at least 500, at least 1000, at least 5000, or more base pairs. The conjugated nucleic acid can be single stranded. In various aspects, the conjugated nucleic acid can be double stranded. In some aspects, the conjugated nucleic acid encodes an open reading frame. In some aspects, the open reading frame encoded by the conjugated nucleic acid corresponds to an apoptosis inducing protein, a viral protein, an enzyme, or a tumor suppressor protein. Techniques for delivery of such nucleic acids to cells are known in the art.

(b) Linkers

In some aspects, the heterologous moiety is conjugated to one of the engineered cysteines via a linker. As used herein, the term "linker" refers to a peptide or polypeptide sequence (e.g., a synthetic peptide or polypeptide sequence), or a non-peptide linker for which its main function is to connect a heterologous moiety to a cysteine-engineered antibody or Fc fusion protein via the thiol group of an engineered cysteine. In some aspects, a linker can be present between any two heterologous moieties or non-linker elements of the conjugate compounds of the present disclosure. For example, one or more linkers can be present between a cysteine-engineered antibody or Fc fusion protein and a heterologous moiety, or between a between a first heterologous moiety and a second heterologous moiety. In some aspects, two or more linkers can be linked in tandem. When multiple linkers are present in a conjugate compound disclosed herein, each of the linkers can be the same or different. Generally, linkers provide flexibility to the conjugate compound. Linkers are not typically cleaved, thus, in some aspects, the linker is a non-cleavable linker. However in certain embodiments, such cleavage can be desirable. Accordingly, in some aspects a linker can comprise one or more protease-cleavable sites, which can be located within the sequence of the linker or flanking the linker at either end of the linker sequence.

In some aspects, the conjugate compound comprises a non-peptide linker. In other aspects, the linker consists of a non-peptide linker. In some aspects, the non-peptidic linker comprises, e.g., maleimido caproyl (MC), val-cit, MC-val-cit, MC-val-cit-PABC, Mal-PEG2C2, Mal-PEG3C2 Mal-PEG6C2, maleimido propanoyl (MP), methoxyl polyethyleneglycol (MPEG), succinimidyl 4-(N-maleimidomethyl)-cyclohexane-1-carboxylate (SMCC), MBS (m-maleimidobenzoyl-N-hydroxysuccinimide ester), 4-succinimidyloxycarbonyl-alpha-methyl-alpha-(2-pyridyldithio) toluene (SMPT), succinimidyl 6-[3-(2-pyridyldithio)-propionamide]hexanoate (LC-SPDP), BMPEO, SPP, succinimidyl 4-(p-maleimidophenyl)butyrate (SMPB), N-succinimidyl-S-acetylthioacetate (SATA), N-succinimidyl(4-iodoacetyl)aminobenzonate (SIAB), or any combination thereof. See, e.g., U.S. Pat. No. 7,375,078.

In some aspects, the conjugate compound comprises a peptide linker. In some aspects, the linker consists of a peptide linker. In some aspects, the peptide linker comprises at least two amino, at least three, at least four, at least five, at least 10, at least 20, at least 30, at least 40, at least 50, at least 60, at least 70, at least 80, at least 90, or at least 100 amino acids. In other aspects, the peptide linker comprises at least 200, at least 300, at least 400, at least 500, at least 600, at least 700, at least 800, at least 900, or at least 1,000 amino acids. In yet other aspects, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of peptide linkers are well known in the art, for example peptide linkers according to the formula $[(Gly)_x\text{-}Ser_y]_z$, where x is from 1 to 4, y is 0 or 1, and z is from 1 to 50. In one aspect, the peptide linker comprises the sequence $G_n$, where n can be an integer from 1 to 100. In a specific aspect, the sequence of the peptide linker is GGGG. The peptide linker can comprise the sequence $(GA)_n$. The peptide linker can comprise the sequence $(GGS)_n$. In other aspects, the peptide linker comprises the sequence $(GGGS)_n$. In still other aspects, the peptide linker comprises the sequence $(GGS)_n(GGGGS)_n$. In these instances, n can be an integer from 1-100. In other instances, n can be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS, GGSGGSGGSGGSGGG, GGSGGSGGGGSGGGS, GGSGGSGGSGGSGGSGGS, or GGGGSGGGGSGGGGS. In other aspects, the linker is a poly-G sequence $(GGGG)_n$, where n can be an integer from 1-100.

In one aspect, the peptide linker is synthetic, i.e., non-naturally occurring. In one aspects, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion). In another aspect, the peptide linker can comprise non-naturally occurring amino acids. In another aspect, the peptide linker can comprise naturally occurring amino acids occurring in a linear sequence that does not occur in nature. In still another aspect, the peptide linker can comprise a naturally occurring polypeptide sequence.

III. Cysteine Engineering of Antibodies and Fc Fusion Proteins

In some aspects, the conjugate compound comprises a cysteine-engineered antibody or Fc fusion protein which specifically binds to at least one target. In some aspects, the cysteine-engineered antibody or Fc fusion protein can bind to more than one target. In some aspects, the cysteine-engineered antibody retains the antigen binding capability of the parent antibody counterpart. Thus, a cysteine-engineered antibody disclosed herein can be capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen can be a cluster differentiation factor (i.e., a CD protein). An antigen to which a cysteine-engineered antibody is capable of binding can be a member of a subset of one of the above-mentioned categories.

In some aspects, the conjugate compound comprises a cysteine-engineered antibody or Fc fusion protein which specifically binds to at least one target, and at least one heterologous moiety which specifically binds to at least one second target. In some aspects, a cysteine-engineered antibody or Fc fusion protein and a heterologous moiety can bind to the same target. In other aspects, a cysteine-engineered antibody or Fc fusion protein and a heterologous moiety can bind to different targets. Thus, in some aspects, the conjugate compounds are monospecific. In other aspects, conjugate compounds are bispecific, trispecific, tetraspecific, etc. In other aspects, conjugate compounds are multispecific. In some aspects, conjugate compounds are monovalent, bivalent, trivalent, tetravalent, etc. In yet other aspects, conjugate compounds are multivalent. In specific aspects, the cysteine-engineered antibodies and Fc fusion proteins and derived conjugate compounds are bivalent, e.g., the engineered antibody compound comprises two different specific antigen binding sites or the engineered Fc fusion protein comprises two different target binding domains. In specific aspects, the cysteine-engineered antibodies and fragments thereof and derived conjugate compounds are bispecific, i.e., the molecule can specifically bind to two different antigens (e.g., two different epitopes on the same or different molecules). In some specific aspects, the cysteine-engineered antibodies and fragments thereof and derived conjugate compounds are bispecific and tetravalent, e.g., derived from a parent antibody comprising four antigen-binding sites that are capable of binding to two different antigens (e.g., two different epitopes on the same or different molecules).

The present disclosure provides an assay for detecting the binding of a cysteine-engineered antibody or Fc fusion protein disclosed herein, or a conjugate compound disclosed herein to a target cell comprising:

(a) exposing cells to the a cysteine-engineered antibody or Fc fusion protein or conjugate compound; and (b) determining the extent of binding of the cysteine-engineered antibody or Fc fusion protein or conjugate compound to the target cells.

The target binding capability of a cysteine-engineered antibody or Fc fusion protein disclosed herein, or derived conjugate compound disclosed herein for an target can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can also be readily employed. See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein. The measured affinity of the interaction of a particular a cysteine-engineered antibody or Fc fusion protein, or derived conjugate compound disclosed herein with an target can vary if measured under different conditions (e.g., salt concentration, pH, temperature, etc.).

Virtually any molecule may be specifically bound by and/or incorporated into a conjugate compound comprising a cysteine-engineered antibody or Fc fusion protein and a heterologous moiety. In some aspects members (receptor or ligand) of the TNF superfamily, as well as subunits, domains, motifs and epitopes of proteins belonging to this family of proteins are specifically bound by and/or incorporated into a conjugate compound. The TNF superfamily comprises numerous molecules including, but are not limited to Tumor Necrosis Factor-alpha ("TNF-alpha"), Tumor Necrosis Factor-beta ("TNF-beta"), Lymphotoxin-alpha ("LT-alpha"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-1 (also referred to as BlyS, BAFF or THANK), DR4, DR5 (also known as Apo-2, TRAIL-R2, TR6, Tango-63, hAPO8, TRICK2, or KILLER), DR6, DcR1, DcR2, DcR3 (also known as TR6 or M68), CAR1, HVEM (also known as ATAR or TR2), GITR, ZTNFR-5, NTR-1, TNFL1, CD30, LTBr, 4-1BB receptor and TR9.

In some aspects, the conjugate compound specifically binds to and/or incorporates one or more molecules, as well as subunits, domains, motifs and epitopes of molecules selected from the group consisting of 5T4, ABL, ABCF1, ACVR1, ACVR1 B, ACVR2, ACVR2B, ACVRL1, ADORA2A, Aggrecan, AGR2, AICDA, AIF1, AIGI, AKAP1, AKAP2, AMH, AMHR2, ANGPT1, ANGPT2, ANGPTL3, ANGPTL4, ANPEP, APC, APOC1, AR, aromatase, ATX, AX1, AZGP1 (zinc-a-glycoprotein), B7.1, B7.2, B7-H1, BAD, BAFF, BAG1, BAIL BCR, BCL2, BCL6, BDNF, BLNK, BLR1 (MDR15), BlyS, BMP1, BMP2, BMP3B (GDFIO), BMP4, BMP6, BMP8, BMPR1A, BMPR1B, BMPR2, BPAG1 (plectin), BRCA1, C19orfO (IL27w), C3, C4A, C5, C5R1, CANT1, CASP1, CASP4, CAV1, CCBP2 (D6/JAB61), CCL1 (1-309), CCM (eotaxin), CCL13 (MCP-4), CCL15 (MIP-Id), CCL16 (mcc-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22 (MDC/STC-I), CCL23 (MPIF-I), CCL24 (MPIF-2/eotaxin-2), CCL25 (TECK), CCL26 (eotaxin-3), CCL2γ (CTACK/ILC), CCL28, CCL3 (MIP-la), CCL4 (MIPIb), CCL5 (RANTES), CCL7 (MCP-3), CCL8 (mcp-2), CCNA1, CCNA2, CCND1, CCNE1, CCNE2, CCRI (CKR1/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TERI/CKR-L1), CCR9 (GPR-9-6), CCRL1 (VSHK1), CCRL2 (L-CCR), CD164, CD19, CDIC, CD20, CD200, CD22, CD24, CD28, CD3, CD33, CD35, CD37, CD38, CD3E, CD3G, CD3Z, CD4, CD40, CD40L, CD44, CD45RB, CD52, CD69, CD72, CD74, CD79A, CD79B, CD8, CD80, CD81, CD83, CD86, CD137, CDH1 (Ecadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21Wap1/Cipl), CDKN1B (p27Kip1), CDKN1C, CDKN2A (p161NK4a), CDKN2B, CDKN2C, CDKN3, CEBPB, CERI, CHGA, CHGB, Chitinase, CHST10, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COLIA1, COL4A3, COL6A1, CR2, Cripto, CRP, CSF1 (M-CSF), CSF2 (GM-CSF), CSF3 (GCSF), CTLA4, CTL8, CTNNB1 (b-catenin), CTSB (cathepsin B), CX3CL1 (SCYD1), CX3CR1 (V28), CXCL1 (GRO1), CXCL10 (IP-IO), CXCLI1 (I-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCl, CYSLTR1, DAB21P, DES, DKFZp451J0118, DNCL1, DPP4, E2F1, Engel, Edge, Fennel, EFNA3, EFNB2, EGF, EGFR, ELAC2, ENG, Enola, ENO2, ENO3, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHRIN-A1, EPHRIN-A2, EPHRINA3, EPHRIN-A4, EPHRIN-A5, EPHRIN-A6, EPHRIN-B1, EPHRIN-B2, EPHRIN-B3, EPHB4, EPG, ERBB2 (Her-2), EREG, ERK8, Estrogen receptor, Earl, ESR2, F3 (TF), FADD, farnesyltransferase, FasL, FASNf, FCER1A, FCER2, FCGR3A, FGF, FGF1 (aFGF), FGF10, FGF1 1, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FILI (EPSILON), FBL1 (ZETA), FLJ12584, F1125530, FLRT1 (fibronectin), FLT1, FLT-3, FOS, FOSLI (FRA-1), FY (DARC), GABRP (GABAa), GAGEB1, GAGEC1, GALNAC4S-6ST, GATA3, GD2, GDF5, GFI1, GGT1, GM-CSF, GNAS1, GNRH1, GPR2 (CCR10), GPR31, GPR44, GPR81 (FKSG80), GRCC10 (C10), GRP, GSN (Gelsolin), GSTP1, HAVCR2, HDAC, HDAC4, HDAC5, HDAC7A, HDAC9, Hedgehog, HGF, HIF1A, HIP1, histamine and histamine receptors, HLA-A, HLA-DRA, HM74, HMOX1, HSP90, HUMCYT2A, ICEBERG, ICOSL, ID2, IFN-a, IFNA1, IFNA2, IFNA4,1FNA5, EFNA6, BFNA7, IFNB1, IFNgamma, IFNWl, IGBP1, IGF1, IGFIR, IGF2, IGFBP2, 1GFBP3, IGFBP6, DL-1, ILIO, ILIORA, ILIORB, IL-1, IL1R1 (CD121a), IL1R2 (CD121b), ILIRA, IL-2, IL2RA (CD25), IL2RB (CD122), IL2RG (CD132), IL-4, IL-4R (CD123), IL-5, IL5RA (CD125), IL3RB (CD131), IL-6, IL6RA, (CD126), IR6RB (CD130), IL-7, IL7RA (CD127), IL-8, CXCR1 (ILIRA), CXCR2, (IL8RB/CD128), IL-9, IL9R (CD129), IL-10, IL10RA (CD210), IL10RB (CDW210B), IL-11, IL11RA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, ILIA, ILIB, IL1F10, IL1F5, IL1F6, IL1F7, IL1F8, DL1F9, ILIHYI, ILIR1, IL1R2, ILIRAP, ILIRAPLI, IL1RAPL2, IL1 RL1, ILl RL2, ILIRN, IL2, IL20, IL20RA, IL21 R, IL22, IL22R, IL22RA2, IL23, DL24, IL25, IL26, IL27, IL28A, IL28B, IL29, IL2RA, IL2RB, IL2RG, IL3, IL30, IL3RA, IL4,1L4R, IL6ST (glycoprotein 130), ILK, INHA, INHBA, INSL3, INSL4, IRAK1, IRAK2, ITGA1, ITGA2,1TGA3, ITGA6 (a6 integrin), ITGAV, ITGB3, ITGB4 (134 integrin), JAG1, JAK1, JAK3, JTB, JUN, K6HF, KAI1, KDR, KITLG, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMAS, LEP (leptin), Lingo-p75, Lingo-Troy, LPS, LTA (TNF-b), LTB, LTB4R (GPR16), LTB4R2, LTBR, MACMARCKS, MAG or Omgp, MAP2K7 (c-Jun), MCP-1, MDK, MIB1, midkine, MIF, MISRII, MJP-2, MK, MKI67 (Ki-67), MMP2, MMP9, MS4A1, MSMB, MT3 (metallothionectin-UI), mTOR, MTSS1, MUC1 (mucin), MYC, MYD88, NCK2, neurocan, NFKBI, NFKB2, NGFB (NGF), NGFR, NgR-Lingo, NgRNogo66, (Nogo), NgR-p75, NgR-Troy, NMEI (NM23A), NOTCH, NOTCH1, NOX5, NPPB, NROB1, NROB2, NRID1, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZ1, OPRDI, P2RX7, PAP, PART1, PATE, PAWR, PCA3, PCDGF, PCNA, PDGFA, PDGFB, PDGFRA, PDGFRB, PECAMI, peg-asparaginase, PF4 (CXCL4), PGF, PGR, phosphacan, PIAS2, PI3 Kinase, PIK3CG, PLAU (uPA), PLG, PLXDCI, PKC, PKC-beta, PPBP (CXCL7), PPID, PRE PRKCQ, PRKD1, PRL, PROC, PROK2, PSAP, PSCA, PTAFR, PTEN, PTGS2 (COX-2), PTN, RAC2 (P21Rac2), RANK, RANK ligand, RARB, RGS1, RGS13, RGS3, RNFI10 (ZNF144), Ron, ROBO2, RXR, S100A2, SCGB 1D2 (lipophilin B), SCGB2A1 (mammaglobin 2), SCGB2A2 (mammaglobin 1), SCYE1 (endothelial Monocyte activating cytokine), SDF2, SERPENA1, SERPINA3, SERPINB5 (maspin), SERPINEI (PAI-1), SERPINFI, SHIP-1, SHIP-2, SHB1, SHB2, SHBG, SfcAZ, SLC2A2, SLC33A1, SLC43A1, SLIT2, SPP1, SPRR1B (Sprl), ST6GAL1, STAB1, STAT6, STEAP, STEAP2, TB4R2, TBX21, TCP10, TDGF1, TEK, TGFA, TGFB1, TGFBII1, TGFB2, TGFB3, TGFBI, TGFBR1, TGFBR2, TGFBR3, THIL, THBS1 (thrombospondin-1), THBS2, THBS4, THPO, TIE (Tie-1), TIMP3, tissue factor, TLR10, TLR2, TLR3, TLR4, TLR5, TLR6, TLR7, TLR8, TLR9, TNF, TNFa, TNFAIP2 (B94), TNFAIP3, TNFRSFI1A, TNFRSF1A, TNFRSF1B, TNFRSF21, TNFRSF5, TNFRSF6 (Fas), TNFRSF7, TNFRSF8, TNFRSF9, TNFSF10 (TRAIL), TNFSF1 1 (TRANCE), TNFSF12 (APO3L), TNFSF13 (April), TNFSF13B, TNFSF14 (HVEM-L), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase lia), TP53, TPM1, TPM2, TRADD, TRAF1, TRAF2, TRAF3, TRAF4, TRAF5, TRAF6, TRKA, TREM1, TREM2, TRPC6, TSLP, TWEAK, Tyrosinase, uPAR, VEGF, VEGFB, VEGFC, versican, VHL C5, VLA-4, Wnt-1, XCL1 (lymphotactin), XCL2 (SCM-Ib), XCRI (GPR5/CCXCR1), YY1, and ZFPM2.

In some aspects, the conjugate compound comprises a cysteine-engineered antibody or Fc fusion protein, or a heterologous moiety which specifically binds to and/or incorporates one or more a non-protein molecules, for example, a nucleic acid (e.g., a DNA or an RNA), a lipid, a glycolipid, a polysaccharide, etc. In some aspects, the conjugate compound comprises a cysteine-engineered antibody or Fc fusion protein, or a heterologous moiety which specifically binds to and/or incorporates a tumor-associated glycolipid antigen, as well as subunits, domains, motifs and epitopes of the same; see, e.g., U.S. Pat. No. 5,091,178).

In some aspects, the conjugate compound comprises a cysteine-engineered antibody or Fc fusion protein comprising a domain (e.g., an epitope binding domain, or ligand domain) that competes with ligands for binding PDGFRalpha, PDGFRbeta, PDGF, VEGF, VEGF-A, VEGF-B, VEGF-C. VEGF-D, VEGFE, VEGFF, VEGFR-1, VEGFR-2, VEGFR-3, FGF, FGF2, HGF, KDR, fit-1, FLK-1 Ang-2, Ang-1, PLGF, CEA, CXCL13, Baff, IL-21, CCL21, TNF-alpha, CXCL12, SDF-1, bFGF, MAC-1, IL23p19, FPR, IGFBP4, CXCR3, TLR4, CXCR2, EphA2, EphA4, EphrinB2, EGFR (ErbB1), HER2 (ErbB2 or p185neu), HER3 (ErbB3), HER4 ErbB4 or tyro2), SC1, LRPS, LRP6, RAGE, Nav1.7, GLP1, RSV, RSV F protein, Influenza HA protein, Influenza NA protein, HMGB1, CD16, CD19, CD20, CD21, CD28, CD32, CD32b, CD64, CD79, CD22, ICAM-1, FGFR1, FGFR2, HDGF, EphB4, GITR, 13-amyloid, hMPV, PIV-1, PIV-2, OX4OL, IGFBP3, cMet, PD-1, PLGF, Neprolysin, CTD, IL-18, IL-6, CXCL-13, IL-1R1, IL-15, IL-4R, IgE, PA1-1, NGF, EphA2, CEA, uPARt, DLL-4, av136, a5131, interferon receptor type I and type II. CD19, ICOS, IL-17, Factor II, Hsp90, IGF, CD19, GM-CSFR, PIV-3, CMV, IL-13, IL-9, and EBV.

In some aspects, the conjugate compound comprises a cysteine-engineered antibody or Fc fusion protein which binds to the same target as an antibody selected from the group consisting of abagovomab, abatacept (also known as ORENCIA®), abciximab (also known as REOPRO®, c7E3 Fab), adalimumab (also known as HUMIRA®), adecatumumab, alemtuzumab (also known as CAMPATH®, Mab-Campath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (also known as SIMULECT®), bavituximab, bectumomab (also known as LYMPHOSCAN®), belimumab (also known as LYMPHOSTAT-B®), bertilimumab, besilesomab, bevacizumab (also known as AVASTIN®), biciromab brallobarbital, bivatuzumab mertansine, campath, canakinumab (also known as ACZ885), cantuzumab mertansine, capromab (also known as PROSTASCINT®), catumaxomab (also known as REMOVAB®), cedelizumab (also known as CIMZIA®), certolizumab pegol, cetuximab (also known as ERBITUX®), clenoliximab, dacetuzumab, dacliximab, daclizumab (also known as ZENAPAX®), denosumab (also known as AMG 162), detumomab, dorlimomab aritox, dorlixizumab, duntumumab, durimulumab, durmulumab, ecromeximab, eculizumab (also known as SOLIRIS®), edobacomab, edrecolomab (also known as Mab17-1A, PAN-OREX®), efalizumab (also known as RAPTIVA®), efungumab (also known as MYCOGRAB®), elsilimomab, enlimomab pegol, epitumomab cituxetan, efalizumab, epitumomab, epratuzumab, erlizumab, ertumaxomab (also known as REXOMUN®), etanercept (also known as ENBREL®), etaracizumab (also known as etaratuzumab, VITAX1N®, ABEGRIN™), exbivirumab, fanolesomab (also known as NEUTROSPEC®), faralimomab, felvizumab, fontolizumab (also known as HUZAF®), galiximab, gantenerumab, gavilimomab (also known as ABXCBL®), gemtuzumab ozogamicin (also known as MYLOTARG®), golimumab (also known as CNTO 148), gomiliximab, ibalizumab (also known as TNX-355), ibritumomab tiuxetan (also known as ZEVALIN®), igovomab, imciromab, infliximab (also known as REMICADE®), inolimomab, inotuzumab ozogamicin, ipilimumab (also known as MDX-010, MDX-101), iratumumab, keliximab, labetuzumab, lemalesomab, lebrilizumab, lerdelimumab, lexatumumab (also known as, HGS-ETR2, ETR2-ST01), lexitumumab, libivirumab, lintuzumab, lucatumumab, lumiliximab, mapatumumab (also known as HGSETR1, TRM-1), maslimomab, matuzumab (also known as EMD72000), mepolizumab (also known as BOSATRIA®), metelimumab, milatuzumab, minretumomab, mitumomab, morolimumab, motavizumab (also known as NUMAX™), muromonab (also known as OKT3), nacolomab tafenatox, naptumomab estafenatox, natalizumab (also known as TYSABRI®, ANTEGREN®), nebacumab, nerelimomab, nimotuzumab (also known as THERACIM hR3®, THERA-CIM-hR3®, THERALOC®), nofetumomab merpentan (also known as VERLUMA®), ocrelizumab, odulimomab, ofatumumab, omalizumab (also known as XOLAIR®), oregovomab (also known as OVAREX®), otelixizumab, pagibaximab, palivizumab (also known as SYNAGIS®), panitumumab (also known as ABX-EGF, VECTIBIX®), pascolizumab, pemtumomab (also known as THERAGYN®), pertuzumab (also known as 2C4, OMNITARG®), pexelizumab, pintumomab, priliximab, pritumumab, ranibizumab (also known as LUCENTIS®), raxibacumab, regavirumab, reslizumab, rituximab (also known as RITUXAN®, MabTHERA®), rovelizumab, ruplizumab, satumomab, sevirumab, sibrotuzumab, siplizumab (also known as MEDI-507), sontuzumab, stamulumab (also known as MYO-029), sulesomab (also known as LEUKOSCAN®), tacatuzumab tetraxetan, tadocizumab, talizumab, taplitumomab paptox, tefibazumab (also known as AUREX1S®), telimomab aritox, teneliximab, teplizumab, ticilimumab, tocilizumab (also known as ACTEMRA®), toralizumab, tositumomab, trastuzumab (also known as HERCEPTIN®), tremelimumab (also known as CP-675,206), tucotuzumab celmoleukin, tuvirumab, urtoxazumab, ustekinumab (also known as CNTO 1275), vapaliximab, veltuzumab, vepalimomab, visilizumab (also known as NUVION®), volociximab (also known as M200), votumumab (also known as HUMASPECT®), zalutumumab, zanolimumab (also known as HuMAX-CD4), ziralimumab, or zolimomab aritox. In some aspects, the conjugate compound comprises a cysteine-engineered antibody or Fc fusion protein comprising an antigen-binding region from an antibody selected from the previous list of antibodies.

The conjugate compounds disclosed herein can specifically bind to and/or incorporate molecules from multiple sources, for example, viral, bacterial (e.g., mycoplasma), fungal, or animal targets. In some cases, the animal molecule is a human molecule. In some aspects, the conjugate compounds disclosed herein can specifically bind to and/or incorporates molecules from parasites (e.g., fungi, bacteria, nemotodes, etc.). In some aspects, the molecule is an antigen. Accordingly, in some aspects, the conjugate compound can target a bacterial antigen, and the heterologous moiety is an antibacterial agent. In other aspects, the target is a viral antigen and the heterologous moiety is an antiviral agent. In yet other aspects, the conjugate compound can target a tumor antigen (e.g., a human tumor antigen) and the heterologous moiety is an antitumor agent. In some aspects, the conjugate compound can target a fungal antigen and the heterologous moiety is an antifungal agent. In some aspects, the conjugate compound can target a parasite antigen and the heterologous moiety is antiparasitic agent. In other aspects, the conjugate compound can target a mycoplasmal antigen and the heterologous moiety is an antimycoplasmal agent. In some aspects, the conjugate compound can target a differentiation or histocompatibility antigen and the heterologous moiety is a cytotoxic agent. Cysteine-engineered antibodies and Fc fusion proteins including the disclosed cysteine mutations (substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, cysteine amino acid insertion between positions 239 and 240, and any combinations thereof) and optionally one or more cysteine mutations at additional positions suitable for cysteine-engineering described in the art (e.g., substitutions at amino acid positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446) can be prepared according to methods known in the art. See, e.g., U.S. Pat. No. 4,816,567.

Nucleic acids, e.g., DNA, encoding the disclosed cysteine mutations can be prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies and Fc fusion proteins can be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine-engineered antibodies and Fc fusion proteins. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e., mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis can be carried out within the gene expressing the protein to be mutagenized in an expression plasmid and the resulting plasmid can be sequenced to confirm the introduction of the desired cysteine replacement mutations (Liu et al (1998) J. Biol. Chem. 273:20252-20260). Site-directed of protocols and formats, including those commercially available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they can be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

The polynucleotide(s) encoding cysteine-engineered antibodies or Fc fusion proteins of the present disclosure can further be modified in a number of different manners using recombinant DNA technology. In some aspects, the constant domains of the light and heavy chains of an antibody, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

Human antibodies can be directly prepared using various techniques known in the art Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., J. Immunol. 147:86-95 (1991); and U.S. Pat. No. 5,750,373). One or more cDNAs encoding the antibody in the immortalized B lymphocyte can then be prepared and inserted into an expression vector and/or a heterologous host cell for expression of a non-naturally-occurring recombinant version of the antibody.

Also, the cysteine-engineered antibodies or Fc fusion proteins disclosed herein can be selected from a phage library, where that phage library expresses human antibodies or fragments thereof as fusion proteins with heterologous phage proteins, as described, for example, in Vaughan et al., Nat. Biotech. 14:309-314 (1996); Sheets et al., Proc. Natl. Acad. Sci. 95:6157-6162 (1998); Hoogenboom and Winter, J. Mol. Biol. 227:381 (1991), and Marks et al., J. Mol. Biol. 222:581 (1991)). Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963, each of which is incorporated by reference in its entirety.

In some aspects, an cysteine-engineered antibody or Fc fusion protein of the present disclosure can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. Humanization, resurfacing or engineering of the cysteine-engineered antibodies or fragments thereof disclosed herein can be performed using any known method, such as but not limited to those described in, Damschroder et al., Mol. Immunol. 44:3049-3060 (2007); Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; WO90/14443; WO90/14424; WO90/14430; WO2005/042743; WO2006/102095 and EP229246, each of which is entirely incorporated herein by reference, including the references cited therein.

IV. Expression and Purification of Cysteine-engineered Antibodies and Fc Fusion Proteins In certain aspects, the present disclosure provides polynucleotides comprising nucleic acid sequences that encode a cysteine-engineered antibody or Fc fusion protein including the disclosed cysteine mutations (substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, cysteine amino acid insertion between positions 239 and 240, and any combinations thereof). These polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain aspects the DNA is a cDNA that is used to produce a non-naturally-occurring recombinant cysteine-engineered antibody or Fc fusion protein.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide (either natural or heterologous) which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. In certain aspects, the polynucleotides are altered to optimize codon usage for a certain host cell.

In certain aspects the polynucleotides comprise the coding sequence for the mature cysteine-engineered antibody or Fc fusion protein fused in the same reading frame to a heterologous marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The polynucleotides can contain alterations in the coding regions, non-coding regions, or both. In some aspects, these polynucleotide variants contain alterations that produce silent substitutions, additions, or deletions, but do not alter the properties or activities of the encoded polypeptide. In some aspects, the polynucleotide variants are produced by silent substitutions due to the degeneracy of the genetic code. Polynucleotide variants can also be produced for a variety of reasons, e.g., to optimize codon expression for a particular host (change codons in the human mRNA to those preferred by a bacterial host such as E. coli).

In some aspects, a polynucleotide encoding a cysteine-engineered antibody or Fc fusion protein disclosed herein can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Vectors and cells comprising the polynucleotides described herein are also provided. Once assembled (by synthesis, site-directed mutagenesis or another method), the polynucleotide sequences encoding a particular isolated polypeptide of interest (e.g., a cysteine-engineered antibody or Fc fusion protein) can be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding the cysteine-engineered antibodies or Fc fusion proteins disclosed herein. Recombinant expression vectors are replicable DNA constructs which have synthetic or cDNA-derived DNA fragments encoding, for example, a polypeptide chain of an anti-HER2 antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from E. coli, including pCR 1, pBR322, pMB9 and their derivatives, wider host range plasmids, such as M13 and filamentous single-stranded DNA phages.

Suitable host cells for expression of cysteine-engineered antibodies or Fc fusion proteins include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Publ. No. 2008/0187954, U.S. Pat. Nos. 6,413,746 and 6,660,501, and Int'l Pat. Publ. No. WO 04009823, each of which is hereby incorporated by reference in its entirety.

Various mammalian or insect cell culture systems can also be advantageously employed to express recombinant cysteine-engineered antibodies or Fc fusion proteins of the present disclosure. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow & Summers, BioTechnology 6:47 (1988).

Cysteine-engineered antibodies or Fc fusion proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some aspects, an anion exchange resin can be employed, for example, a matrix or substrate having pendant diethylaminoethyl (DEAE) groups. The matrices can be acrylamide, agarose, dextran, cellulose or other types commonly employed in protein purification. In some aspects, a cation exchange step can be employed. Suitable cation exchangers include various insoluble matrices comprising sulfopropyl or carboxymethyl groups.

Additionally, or optionally, one or more reversed-phase high performance liquid chromatography (RP-HPLC) steps employing hydrophobic RP-HPLC media, e.g., silica gel having pendant methyl or other aliphatic groups, can be employed to further purify a cysteine-engineered antibody or fragment thereof. Some or all of the foregoing purification steps, in various combinations, can also be employed to provide a homogeneous recombinant protein.

A recombinant cysteine-engineered antibody or Fc fusion protein produced in culture can be isolated, for example, by initial extraction from cell pellets, followed by one or more concentration, salting-out, aqueous ion exchange or size exclusion chromatography steps. High performance liquid chromatography (HPLC) can be employed for final purification steps. Cells employed in expression of a recombinant protein can be disrupted by any convenient method, including freeze-thaw cycling, sonication, mechanical disruption, or use of cell lysing agents. Methods known in the art for purifying antibodies and other proteins also include, for example, those described in U.S. Pat. Publ. Nos. US2008/0312425, US2008/0177048, and US2009/0187005, each of which is hereby incorporated by reference in its entirety.

V. Conjugation of Heterologous Moieties to Cysteine-Engineered Antibodies and Fc Fusion Proteins Cysteine-engineered antibodies and Fc fusion including the disclosed cysteine mutations (substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, cysteine amino acid insertion between positions 239 and 240, and any combinations thereof) can be site-specifically and efficiently coupled with at least one heterologous moiety using thiol-reactive reagents. In some aspects, the conjugation of a heterologus moiety can occur at a thiol group provided by at least one engineered cysteine residue at one or more positions disclosed herein (e.g., positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, or a cysteine amino acid insertion between positions 239 and 240), and optionally at least one engineered cysteine residue at one or more positions known in the art (e.g., positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446).

Various methods for conjugating a heterologous moiety to an engineered cysteine residue are known in the art. Reagents for such conjugation typically bear reactive functionality which may react directly with a cysteine thiol of a cysteine (e.g., an engineered csteine cysteine of the invention) to form the conjugate compound, or with a linker reagent to form a linker-label intermediate, or with a linker protein to form the conjugate compound. In the case of a linker organic chemistry reactions, conditions, and reagents which may be used include but are not limited to: reaction of a cysteine group with a linker reagent, to form a protein linker intermediate, via a covalent bond, followed by reaction with an activated heterologous moiety; and reaction of a nucleophilic group of a heterologous moiety with a linker reagent, to form heterologous moiety-linker intermediate, via a covalent bond, followed by reaction with an cysteine group (e.g., an engineered cysteine of the invention).

In certain aspects, bifunctional linkers are useful in the present invention. For example, the bifunctional linker comprises a thiol modification group for covalent linkage to the cysteine residue(s) and at least one attachment moiety (e.g., a second thiol modification moiety) for covalent or non-covalent linkage to the conjugate compound. A variety of proteins and compounds, (and linkers) can be used to prepare a compound of the invention. Cysteine thiol groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as halo acetamides; (iii) aldehydes, ketones, carboxyl, and maleimide groups; and (iv) disulfides, including pyridyl disulfides, via sulfide exchange. Nucleophilic groups on a heterologous moiety or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents. In certain aspects, labelling reagents include maleimide, haloacetyl, iodoacetamide succinimidyl ester, isothiocyanate, sulfonyl chloride, 2,6-dichlorotriazinyl, The efficiency of conjugation of a heterologus molecule to an cysteine-engineered antibody or Fc fusion protein disclosed herein can be determined by assessing the presence of free thiols remaining after the conjugation reaction. The presence of free thiol groups can be determined by various art accepted techniques. In certain aspects, the method herein provides for efficiently conjugating a heterologus moiety wherein the conjugation efficiency is at least 5%, at least 10%, at least 15%, at least 20%, at least 25%, at least 30%, at least 35%, at least 40%, at least 45%, at least 50%, at least 55%, at least 60%, at least 70%, at least 75%, at least 80%, at least 85%, at least 90%, at least 95%, at least 98% or more as measured by the level of free thiol groups remaining after the conjugation reaction.

In some aspects, the method herein provides for conjugating a heterologus moiety to a cysteine-engineered antibody or Fc fusion protein disclosed herein containing free cysteine residues that comprise sulfhydryl groups that are blocked or capped. Such caps include proteins, peptides, ions and other materials that interact with the sulfhydryl group and prevent or inhibit conjugate formation. In some aspects, the cysteine-engineered antibodies or Fc fusion proteins disclosed herein can require uncapping prior to a conjugation reaction. In specific aspects, the cysteine-engineered antibodies or Fc fusion proteins are uncapped and display a free sulfhydryl group capable of conjugation. In specific aspects, the cysteine-engineered antibodies or Fc fusion proteins disclosed herein are subjected to an uncapping reaction that does not disturb or rearrange the naturally occurring disulfide bonds.

In some aspects, the cysteine-engineered antibodies or Fc fusion proteins disclosed herein can be subjected to conjugation reactions where the cysteine-engineered antibody or Fc fusion protein to be conjugated is present at a concentration of at least 1 mg/ml, at least 2 mg/ml, at least 3 mg/ml, at least 4 mg/ml, at least 5 mg/ml or higher.

The thiol-reactive reagent can be, for example, a multifunctional linker reagent, a capture (i.e., affinity) label reagent (e.g., a biotin-linker reagent), a detection label (e.g., a fluorophore reagent), a solid phase immobilization reagent (e.g., SEPHAROSE™, polystyrene, or glass), or a drug-linker intermediate. One example of a thiol-reactive reagent is N-ethyl maleimide (NEM). In an exemplary aspect, reaction of a cysteine-engineered antibody or Fc fusion protein with a multifunctional linker reagent provides an intermediate conjugate compound with a functionalized linker which can be further reacted with a heterologous moiety (e.g., a drug moiety).

Such an approach can be applied to the conjugation of other thiol-reactive agents in which the reactive group is, for example, a maleimide, an iodoacetamide, a pyridyl disulfide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

Accordingly, a cysteine-engineered antibody or Fc fusion protein disclosed herein can be conjugated using thiol-conjugation methods known in the art to at least one heterologous moiety such as a toxin, drug, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, non-natural amino acid, peptide, lipid, carbohydrate, scaffolding molecule, fluorescent tag, visualization peptide, biotin, serum half-life extender, capture tag, chelating agent, solid support, or a combination thereof, wherein conjugation is at one of the engineered cysteines.

VI. Pharmaceutical Compositions

The present disclosure provides formulations comprising at least one conjugate compound disclosed herein formulated together with a diluent, carrier, or excipient. The present disclosure also provides pharmaceutical compositions comprising at least one conjugate compound disclosed herein formulated together with a pharmaceutically acceptable diluent, carrier, or excipient. Such formulations or pharmaceutical compositions can include one or a combination of, for example, but not limited to, two or more different conjugate compounds. For example, a formulation or pharmaceutical composition disclosed herein can comprise a combination of conjugate compounds that bind to different targets, e.g., different epitopes, or that have complementary activities.

To prepare pharmaceutical or sterile compositions including a conjugate compound disclosed herein, the conjugate compound can be mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions.

Pharmaceutical compositions comprising conjugate compounds disclosed herein also can be administered in combination therapy, such as, combined with other agents. For example, the combination therapy can include a conjugate compound disclosed herein combined with at least one other therapy where the therapy can be surgery, immunotherapy, chemotherapy, radiation treatment, or drug therapy.

The pharmaceutical compounds can include one or more pharmaceutically acceptable salt. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also can include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that can be employed in the pharmaceutical compositions disclosed herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions can also contain adjuvants such as preservatives, wetting agents, emulsifying agents and dispersing agents. Prevention of presence of microorganisms can be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it can be suitable to include isotonic agents, for example, sugars, poly-alcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, appropriate methods of preparation include vacuum drying and freeze-drying (lyophilization) that yield a powder of the active ingredient plus any additional desired ingredient from a previously sterile-filtered solution thereof.

In one aspect, the compositions herein are pyrogen-free formulations that are substantially free of endotoxins and/or related pyrogenic substances. Endotoxins include toxins that are confined inside a microorganism and are released when the microorganisms are broken down or die. Pyrogenic substances also include fever inducing, thermostable substances (glycoproteins) from the outer membrane of bacteria and other microorganisms. Both of these substances can cause fever, hypotension and shock if administered to humans. Due to the potential harmful effects, even low amounts of endotoxins can be appropriately removed from intravenously administered pharmaceutical drug solutions. The Food & Drug Administration ("FDA") has set an upper limit of 5 endotoxin units (EU) per dose per kilogram body weight in a single one-hour period for intravenous drug applications. When therapeutic proteins are administered in amounts of several hundred or thousand milligrams per kilogram body weight even trace amounts of endotoxin may appropriately be removed.

In an aspect, endotoxin and pyrogen levels in the composition are less than 10 EU/mg, less than 5 EU/mg, less than 1 EU/mg, less than 0.1 EU/mg, less than 0.01 EU/mg, or less than 0.001 EU/mg. In certain embodiments, endotoxin and pyrogen levels in the composition are less than about 10 EU/mg, less than about 5 EU/mg, less than about 1 EU/mg, or less than about 0.1 EU/mg, less than about 0.01 EU/mg, or less than about 0.001 EU/mg.

VII. Diagnostic Methods

In certain aspects, conjugate compounds herein presented can be used in vivo and/or in vitro for diagnostic assays. Such diagnostic assays comprise, for example, (i) detecting the presence or absence of a disease or disorder, (ii) monitoring or prognosing the development or progression of a disease or disorder (such as, but not limited to cancer), (iii) clinical testing procedures, such as determining the efficacy of a particular therapy, or (iv) identifying candidate patients for a certain treatment.

In some aspects, the technologies disclosed herein provide methods of determining the presence of a target molecule of interest in a sample suspected of containing such a molecule. In some aspects, the method comprises exposing the sample to a conjugate compound disclosed herein, and determining binding of conjugate compound to the target molecule of interest in the sample where binding of the conjugate compound to the target molecule of interest in the sample is indicative of the presence of the target molecule of interest in the sample. In some aspects, the sample is a biological sample. In certain aspects, the biological sample is from a mammal experiencing or suspected of experiencing disease or disorder associated with the target molecule of interest.

For example, detecting the binding of a conjugate compound disclosed herein to a target molecule of interest (e.g., a target on the surface of a cell) can be achieved by:
(a) exposing a sample to be tested (e.g., cells) to the conjugate compound, optionally along with a control sample under conditions that allow for formation of a complex between the conjugate compound and the target molecule of interest; and
(b) determining the extent of binding of the conjugate compound to the target molecule.

The conjugate compounds disclosed herein can be used in method of detecting cancer, autoimmune, inflammatory, or infectious diseases or disorders in a subject in need thereof, wherein the method comprises administering to the subject the conjugate compound. Complex formation between the conjugate compound and the target can be detected, e.g., using an ELISA. When using a control sample along with the test sample, complex can be detected in both samples and any statistically significant difference in the formation of complexes between the samples is indicative of the presence of the target molecule of interest in the test sample.

In certain aspects, a conjugate compound disclosed herein can be used to detect the overexpression or amplification of a target molecule of interest using an in vivo diagnostic assay. In some aspects, the conjugate compound is added to a sample where the conjugate compound binds the target molecule of interest to be detected and is tagged with a detectable label (e.g. a radioactive isotope or a fluorescent label) and externally scanning the patient for localization of the label. FISH assays such as the INFORM™ (sold by Ventana, Ariz.) or PATHVISION™ (Vysis, Ill.) can be carried out on formalin-fixed, paraffin-embedded tissue to determine the extent (if any) of overexpression of a target molecule of interest, for example, in a tumor.

In certain aspects, a conjugate compound disclosed herein can be used in a method of diagnosing a cell proliferative disorder associated with an increase in cells expressing a target molecule of interest. In some aspects, the method comprises contacting test cells in a biological sample with a conjugate compound disclosed herein; determining the level of a target molecule of interest in test cells in the sample by detecting binding of the conjugate compound disclosed herein; and comparing the level of conjugate compound bound to cells in a control sample, where the level of conjugate compound bound is normalized to the number molecule of interest expressing cells in the test and control samples, and where a higher level of conjugate compound bound in the test sample as compared to the control sample indicates the presence of a cell proliferative disorder associated with cells expressing the target molecule of interest.

In certain aspects, a conjugate compound disclosed herein can be used in a method of detecting soluble molecule of interest in blood or serum. In some aspects, the method comprises contacting a test sample of blood or serum from a mammal suspected of experiencing a disorder associated with a molecule of interest with a conjugate compound disclosed herein and detecting an increase in soluble molecule of interest in the test sample relative to a control sample of blood or serum from a normal mammal. In some aspects, the method of detecting is useful as a method of diagnosing a disorder associated with an increase in soluble molecule of interest in blood or serum of a mammal.

In certain aspects, conjugate compounds disclosed herein can be used as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) (see Chen et al. (2004) Bioconjugate Chem. 15:41-49); (v) bioluminescence; (vi) fluorescence; and (vii) ultrasound Immunoscintigraphy is an imaging procedure in which antibody-derived compounds labeled with radioactive substances are administered to an animal or human patient and a picture is taken of sites in the body where the antibody localizes (U.S. Pat. No. 6,528,624). Imaging biomarkers can be objectively measured and evaluated as an indicator of normal biological processes, pathogenic processes, or pharmacological responses to a therapeutic intervention. Imaging biomarkers can provide pharmacodynamic (PD) therapeutic information about: (i) expression of a target protein, (ii) binding of a therapeutic to the target protein, i.e. selectivity, and (iii) clearance and half-life pharmacokinetic data.

VIII. Treatment Methods

The present disclosure also provides a method of treating cancer, autoimmune, inflammatory, or infectious diseases or disorders in a subject in need thereof, comprising administering to the subject a conjugate compound disclosed herein. In some aspects, the method further comprises the administration of an additional therapy, wherein the additional therapy is, for example, chemotherapy, biological therapy, immunotherapy, radiation therapy, hormonal therapy, and surgery. Also provided is a method of delivering a heterologous moiety, for example, a therapeutic agent, to a cell, comprising treating the cell with a conjugate compound disclosed herein. In some aspects, the conjugate compound can be internalized by a cell.

In various aspects, a conjugate compound disclosed herein can be administered to cells, for example cancer cells. The biological effect of the conjugate compound can be, e.g., cell death, cell proliferation inhibition, lack of effect, changes in cell morphology, or changes in cellar growth pattern. In some aspects, the conjugate compound comprises a detectable label as described above. In certain aspects, the label indicates the location of a tumor antigen within the cell.

In certain aspects, the conjugate compound can be administered to a subject in need of treatment. In various aspects, a conjugate compound carries a drug or toxin targeted to a tumor antigen. In some aspects, the conjugate compound carries a detectable label by which a target, e.g., an antigen, can be identified or localized. Some aspects comprise the detection of the biological effect, e.g., a therapeutic affect, of the conjugate compound. In certain aspects, the condition of the subject can be monitored. The medical dose of conjugate compound can be adjusted in response to monitoring.

The conjugate compounds disclosed herein and compositions comprising the same are useful for many purposes, for example, as therapeutics to prevent, manage or treat a wide range of chronic and acute diseases and disorders including, but not limited to, autoimmune and/or inflammatory disorders hyperproliferative disorders such as benign or malignant tumors, leukemia and lymphoid malignancies; infectious disease, including viral, bacterial and fungal diseases. In some aspects the compositions and methods disclosed herein can be used with one or more conventional therapies that are used to prevent, manage or treat the above diseases and disorders. Also provided, in some aspects are methods of using conjugate compounds disclosed herein to inactivate various infectious agents such as viruses, fungi, eukaryotic microbes, and bacteria.

Provided also, in some aspects, are methods of using conjugate compounds disclosed herein and compositions comprising the same to deplete a cell population. In an aspect, methods herein can be used in the depletion of the following cell types: eosinophil, basophil, neutrophil, T cell, B cell, mast cell, monocytes, endothelial cell and tumor cell.

In certain aspects, the conjugate compounds disclosed herein and compositions comprising the same can also be useful in the diagnosis and detection of diseases of symptoms thereof. In some aspects, the compositions can be useful in the monitoring of disease progression. In various aspects, the compositions can be useful in the monitoring of treatment regimens. In certain aspects, the compositions are useful for diagnosis in an ex vivo application, such as a diagnostic kit.

In some aspects, the conjugate compounds disclosed herein and compositions comprising the same can target antigens are cell surface receptors that internalize. In certain aspects, the target antigen is an extracellular antigen. In some aspects, the target is an intranuclear antigen. In some aspects, the conjugate compounds disclosed herein, once bound, internalize into cells where internalization is at least about 10%, at least about 20%, at least about 30%, at least about 40%, at least about 50%, at least about 60%, at least about 70%, at least about 80%, or at least about 90%, at least about 100%, at least about 1 10%, at least about 130%, at least about 140%, at least about 150%, at least about 160%, or at least about 170% more than control antibodies.

In certain embodiments, the conjugate compounds disclosed herein, once bound, internalize into cells where internalization is 1-10%, 10-20%, 20-30%, 30-40%, 40-50%, 50-60%, 60-70%, 70-80%, 80-90%, 90-100%, 100-110%, 110-120%, 120-130%, 130-140%, 140-150%, 150-160%, 160-170%, or more than control antibodies.

IX. Kits

The present disclosure also provides articles of manufacture, e.g., kits, that comprise a conjugate compound disclosed herein that can be used to perform the methods described herein. In certain aspects, a kit comprises at least one purified conjugate compound in one or more containers. In some aspects, the kits contain all of the components necessary and/or sufficient to perform a detection assay, including all controls, directions for performing assays, and, for example, any necessary software for analysis and presentation of results. One skilled in the art will readily recognize that the conjugate compounds disclosed herein can be readily incorporated into one of the established kit formats that are well known in the art. In some aspects, the kit comprises a container and a label or package insert on or associated with the container. Suitable containers include, for example, bottles, vials, syringes, blister pack, etc. The containers can be formed from a variety of materials such as glass or plastic. In some aspects, the container can hold a composition comprising a conjugate compound disclosed herein which is effective for treating a specific disease or condition and can have a sterile access port (for example the container can be an intravenous solution bag or a vial having a stopper pierceable by a hypodermic injection needle). The label or package insert can indicate that the composition is used for treating the condition of choice, such as cancer. Alternatively, or additionally, the kit can further comprise a second (or third) container comprising a pharmaceutically-acceptable buffer, such as bacteriostatic water for injection (BWFI), phosphate-buffered saline, Ringer's solution and dextrose solution. The kit can further include other materials desirable from a commercial and user standpoint, including other buffers, diluents, filters, needles, and syringes All of the references cited above, as well as all references cited herein, are incorporated herein by reference in their entireties.

The following examples are offered by way of illustration and not by way of limitation

EXAMPLES

Example 1

Fc Cysteine Scanning 187 amino acids of the Fc region were individually mutated to cysteine using QuikChange mutagenesis. The expression and aggregation levels were examined in a high throughput small scale transfection and expression system. The conjugation efficiency was initially examined in a high throughput automated solid phase conjugation method using a PhyNexus Micro-Extractor Automated instrument and normalized to the conjugation efficiency of Fc-T289. (Fc-T289C has a conjugation efficiency of higher than 95% in this assay.)

Manual liquid-phase, medium scale, conjugation was performed to confirm the conjugation efficiency of the mutations that had conjugation efficiency of at least about 50% of that seen for T289C. The Fc mutants were expressed in shake flasks and the expression level in conditioned media was determined. The Fc-mutants were purified over protein A and the aggregation level was analyzed by SEC.

Table 2 shows the conjugation and small scale expression data for mutants having a conjugation efficiency of at least 50% of that seen for T289C in the Phynexus method. Conjugation efficiencies of >100% are bolded and underlined; 80-100% are underlined; 50-80% are in plain text. Clones with a conjugation efficiency of less that 50% are not shown. Also provided in Table 3 are the conjugation efficiencies of selected mutants as determined using manual liquid-phase conjugation. Table 3 shows the expression level and percent monomer content for selected mutants.

The conjugation efficiency of the E258C and H435C with AF488 was also measured by mass spectrometry and compared to the efficiency of previously reported Fc mutations S239C, T289C and the light chain mutation V205C (referred to herein as LC-V205C). As summarized in Table 4, all the mutations have a conjugation efficiency of nearly 100% (DAR=2 is 100% conjugation). The wild type antibody is included as a negative control (i.e., no engineered cysteine residues).

As can be seen from these studies, cysteines engineered into the majority of the sites provided in Table 2 below have a conjugation efficiency of at least ~50 and are well expressed. These sites may be useful for the generation of antibody or Fc-fusion protein conjugates. In particular, engineered cysteines at a number of positions including 258, 274, 286, 289, 291, 293, 296, 318, 329, 340, 341, 342, 345, 401, 415, 433, 435 and 443, exhibit very high conjugation efficiency in one or both assay formats and are well expressed. Use of engineered cysteine residues at one or more of these sites is contemplated for the efficient generation of site specific antibody or Fc-fusion protein conjugates.

TABLE 2

Summary of Conjugation Efficiency Studies

| Domain | Position | Mutation | Phynexus conjugation % of T289C | Manual conjugation % of T289C | 96-well expression (Octet) mg/L |
|---|---|---|---|---|---|
| CH2 | 241 | F241C | 66.3 | 100.1 | 229 |
| CH2 | 243 | F243C | 64.1 | 115.4 | 211 |
| CH2 | 246 | K246C | 68.0 | 104.2 | 209.5 |
| CH2 | 251 | L251C | 52.3 | N/D | 232.5 |
| CH2 | 253 | I253C | 57.2 | N/D | 105.5 |
| CH2 | 254 | S254C | 101.2 | 90.6 | 193.5 |
| CH2 | 258 | E258C | 114.3 | 143.4 | 120.5 |
| CH2 | 264 | V264C | 85.6 | 148 | 239 |
| CH2 | 269 | E269C | 115.6 | 123.5 | 234 |
| CH2 | 271 | P271C | 107.9 | 101.2 | 189 |
| CH2 | 272 | E272C | 122.6 | 130 | 177.5 |
| CH2 | 274 | K274C | 95.4 | 146.8 | 198 |
| CH2 | 280 | D280C | 67.0 | expression low | 69 |
| CH2 | 281 | G281C | 107.6 | 141.7 | N/D |
| CH2 | 283 | E283C | 100.9 | 90.6 | 183 |
| CH2 | 284 | V284C | 62.4 | 125.5 | 246.5 |
| CH2 | 285 | H285C | 78.2 | 176 | 249 |
| CH2 | 286 | N286C | 123.6 | 123.2 | 236 |
| CH2 | 288 | K288C | 86.0 | 128.1 | 193 |
| CH2 | 291 | P291C | 128.8 | 138 | 192 |
| CH2 | 293 | E293C | 104.6 | 120 | 176 |
| CH2 | 294 | E294C | 76.9 | 90.6 | 212.5 |
| CH2 | 296 | Y296C | 118.1 | 130.8 | 215.5 |
| CH2 | 299 | T299C | 53.1 | N/D | 167 |
| CH2 | 301 | R301C | 62.2 | 130.5 | 253 |
| CH2 | 307 | T307C | 50.8 | N/D | 189 |
| CH2 | 309 | L309C | 84.7 | monomer % low | 220 |
| CH2 | 311 | Q311C | 55.2 | N/D | 192 |
| CH2 | 318 | E318C | 97.5 | 104 | 236.5 |
| CH2 | 329 | P329C | 90.4 | 122.6 | 203 |
| CH2 | 340 | K340C | 95.0 | 123.6 | 220 |
| CH3 | 341 | G341C | 124.3 | 146.5 | 116.5 |
| CH3 | 342 | Q342C | 117.1 | 126 | 107.5 |
| CH3 | 345 | E345C | 123.7 | 121.2 | 122 |
| CH3 | 355 | R355C | 91.3 | 85.5 | 122 |
| CH3 | 357 | E357C | 58.5 | 65.4 | 128 |
| CH3 | 358 | L358C | 51.8 | 79.5 | 120.5 |
| CH3 | 375 | S375C | 61.3 | 72.0 | 123.5 |
| CH3 | 385 | G385C | 77.2 | 125.2 | 195 |
| CH3 | 386 | Q386C | 69.0 | 129.4 | 176 |
| CH3 | 387 | P387C | 53.4 | 105.9 | 236 |
| CH3 | 390 | N390C | 78.5 | 126.4 | N/D |
| CH3 | 401 | D401C | 106.6 | 93.8 | 149.3 |
| CH3 | 402 | G402C | 78.0 | 86.4 | 201.5 |
| CH3 | 411 | T411C | 53.9 | N/D | 146.3 |
| CH3 | 413 | D413C | 93.2 | 44.9 | 153.3 |
| CH3 | 415 | S415C | 121.6 | 95.6 | 109.8 |
| CH3 | 417 | W417C | 57.3 | 32.5 | 88.1 |
| CH3 | 418 | Q418C | 71.8 | 91.0 | 117.3 |
| CH3 | 433 | H433C | 84.8 | 136.5 | 166 |
| CH3 | 435 | H435C | 51.2 | 118.5 | 79 |
| CH3 | 439 | K439C | 93.7 | 77.7 | 162 |
| CH3 | 443 | L443C | 90.5 | 94.3 | 175 |

TABLE 3 expression level and percent monomer content for selected mutants.

| Mutant | Expression (mg/L) | Monomer % |
|---|---|---|
| 1C1-WT | 130 | 96.3 |
| S254C | 107 | 76.4 |
| E258C | 152 | 95.4 |
| V264C | 216 | 94.7 |
| E269C | 130 | 94.4 |
| P271C | 131 | 94.5 |
| E272C | 113 | 81 |
| K274C | 110 | 91.8 |

TABLE 3-continued expression level and percent monomer content for selected mutants.

| Mutant | Expression (mg/L) | Monomer % |
|---|---|---|
| E283C | 120 | 96 |
| H285C | 150 | 86.4 |
| N286C | 150 | 88.1 |
| K288C | 105 | 93.9 |
| P291C | 97 | 73 |
| E293C | 125 | 85.7 |
| E294C | 173 | 80.7 |
| Y296C | 115 | 90.3 |
| R329C | 109 | 95 |
| L309C | 137 | 40.2 |
| E318C | 131 | 95.5 |
| K340C | 111 | 95.4 |
| G341C | 187 | 92.4 |
| Q342C | 85 | 95.8 |
| E345C | 113 | 96.4 |
| R355C | 122 | 95.9 |
| L358C | 87.8 | 95 |
| S375C | 101.5 | 96 |
| G385C | 87.2 | 72 |
| Q386C | 98.7 | 88 |
| P387C | 57.9 | 67 |
| N390C | 89.5 | 96 |
| D401C | 140 | 77 |
| G402C | 76.3 | 88 |
| T411C | 116.4 | 95 |
| D413C | 79.4 | 82 |
| S415C | 59.4 | 51 |
| W417C | 138 | 94 |
| Q418C | 58.7 | 91 |
| H433C | 84.9 | 66 |
| H435C | 91.9 | 90 |
| K439C | 103.5 | 98 |
| L443C | 98.4 | 96 |

TABLE 4

Conjugation Efficiency Measured by Mass Spectrometry

| Ab-conjugate | DAR (IgG) | +2 drugs ratio (IgG) |
|---|---|---|
| 1C1-E258C-AF488 | 2.04 | 98% (HC) |
| 1C1-H435C-AF488 | 1.98 | 96% (HC) |
| 1C1-S239C-AF488 | 1.98 | 96% (HC) |
| 1C1-LC-V205C-AF488 | 2.06 | 99% (LC) |
| 1C1-T289C-AF488 | 2.00 | 94% (HC) |

Example 2

Insertion Mutants and Initial Serum Stability Screen

In addition to the cysteine substitutions described in Example 1, two insertion mutants were generated in which a cysteine residue was inserted between residues 239 and 240 (designated C239ins) or between residues 238 and 239 (designated 238-ins). C239ins exhibited a conjugation efficiency comparable to T289C (see, Table 6 and data not shown). This was unexpected as the conjugation efficiency for the V240C mutation was very low (only ~11%).

The serum stability of a number of these variants was examined. For the initial stability assays Alexa Fluor 488 C5-maleimide (AFF488) was conjugated to the selected sites as a surrogate drug cargo to facilitate analysis. Samples were incubated with normal human serum (NHS) or PBS buffer for 3-7 days. A fluorescence size-exclusion chromatography (SEC) assay was used to monitor the stability of AFF488 containing conjugates after incubation with NHS or PBS. Percent fluorescence remaining in the IgG peak was used to estimate the stability. For samples incubated with human serum the percentage of AF488 transferred to human serum albumin (HSA), the predominant recipient of drug exchange in serum, can be measured directly as percent of signal in HSA peak. FIGS. 2-8 show the SEC profiles for mutants E258C, H435C, L443C, C239ins, S239C, LC-V205C, and T289C, respectively and include samples incubated with NHS (panels A and C) and PBS (panels B and D) at day 0 (panels A and B) and day 7 (panels C and D). The results of these studies are plotted in FIG. 9 and summarized in Table 5.

The four conjugation sites (E258C, H435C, L443C and C239ins) tested in these studies were found to have at least 70% of the conjugate compound intact after 7 days of serum incubation, similar to the stability observed for several antibodies comprising the previously reported LC-V205C and S239C mutations (see TABLE 5).

TABLE 5

Stability of selected Cys mutants conjugated with AF488 7 days of serum incubation

| Ab-conjugate | IgG-AF488% retained (day 7) | HSA-AF488% |
|---|---|---|
| 1C1-E258C-AF488 | 81.48 | 14.2 |
| 1C1-H435C-AF488 | 89.92 | 9.01 |
| 1C1-L443C-AF488 | 83.83 | 13.14 |
| 1C1-239ins-AF488 | 75.77 | 17.0 |
| 1C1-S239C-AF488 | 77.05 | 17.6 |
| 1C1-LC-V205C-AF488 | 89.53 | 9.04 |
| 1C1-T289C-AF488 | 45.48 | 41.76 |

Example 3

Fc Receptor Binding and Thermal Stability Measurements

The binding of several mutants to a variety of Fc receptors was tested. E258C, S239C, C239ins, and LC-V205C binding to FcRn was comparable to wild type (WT) in an ELISA assay (FIG. 10A). In addition, the binding of E258C, LC-V205C and S239C to FcRn was essentially the same when conjugated to A488 (FIG. 10B). These data indicate that these mutations, even when conjugated to a drug, do not impact FcRn binding. In contrast, the H435C mutation abolished FcRn binding (data not shown) which corresponds to previously reported observations that a positively charged residue at position EU 435 is required for FcRn binding.

BIACORE analysis was performed to determine the affinity of the C239ins, S442C, and L234F/S239A/S442C triple mutation for the human Fc Receptors, FcγRI, FcγRIIa, FcγRIIb, FcγRIIIa (both the 158V and 158F alleles) and FcRn. The data presented in FIG. 11 demonstrate that the C239ins reduced binding to FcγRI, abolished binding to FcγRIIa, FcγRIIb, FcγRIIIa (both the 158V and 158F alleles) but had a negligible impact on FcRn binding. In contrast, S442C had little impact on binding to any Fc Receptor tested. As expected the addition of L234F and S239A, mutations reported to reduce binding to certain FcγRs, resulted in much reduced binding to FcγRIIa, FcγRIIb, FcγRIIIa (both the 158V and 158F alleles). Thus the C239ins mutation may be particularly useful for generation of site specific antibody or Fc-fusion conjugates when effector function is undesirable.

Differential scanning calorimetry (DSC) was used to examine the thermal stability of E258C, S239C, LC-V205C, C239ins and H435C as compared to wild type (WT). As shown in FIG. 12, the DSC profiles of E258C, S239C, and Lc-V205C mutations were essentially the same as WT indicating that these mutations did not affect thermostability of the model 1C1 IgG1 as measured by DSC. A new lower melting peak appears for both C239ins and H435C, however Tm1 is still above 60° C. for both mutations indicating only a minimal impact on thermal stability for these mutations.

Example 4

Serum Stability of Single Mutation Toxin Conjugates—Cytotoxicity

1C1-Fc-Cys mutant-conjugates: 2 drugs/Ab were tested for serum stability in a cytotoxicity assay: 1C1-S239C, 1C1-E258C, 1C1-H435C, 1C1-L443C, 1C1-LC-V205C, 1C1-239ins, and 1C1-T289C. Also tested were 1C1-ccADC a 6 drug/Ab control prepared using classical conjugation, R347-S239C—negative control for cytotoxicity assay and 1C1-WT—acts as non-conjugated. Each antibody-drug conjugate (ADC) comprises an auristatin based toxin.

As shown in Table 6, each of the cys mutants has a conjugation efficiency of 88-98%, in contrast wild type shows a back ground conjugation of just 2%. The ADCs were incubated with serum for 0, 3 or 7 days and assayed for cytotoxicity as described in Example 6 below. The cytotoxicity curves for each of the single mutations and controls are plotted in FIGS. 13A, B and C (days 0, 3 and 7, respectively). The $EC_{50}$ values are also provided in the tables below the plots. All the data from this study are summarized in Table 7 and the fold $EC_{50}$ loss at day 3 and 7 are provided.

The 1C1-E258C-ADC, 1C1-H435C-ADC, 1C1-L443C-ADC, and 1C1-239ins-ADC, were stable after serum incubation and comparable to other sites reported to be stable in serum (e.g., LC-V205C) when linked using maleimide chemistry. The $EC_{50}$ of these mutations was retained, even after 7 days of serum incubation. 1C1-T289C-ADC lost some activity. See Table 7. Similar studies were performed using an 1C1-238-ins-ADC however this mutation exhibited an $EC_{50}$ loss of more than 6.25 fold over the course of 7 days (data not shown) indicating that conjugates using maleimide chemistry at this site are not stable and quickly lose activity upon incubation in serum.

Four engineered cysteine sites in Fc region located at EU positions 258, 435 and 443 (E258C, H435C, L443C), and a newly engineered insertion site located between EU positions 239 and 240 (239ins) were identified as being high accessible for conjugation and has having exemplary serum stability.

TABLE 6

1C1-Fc-Cys mutant's Conjugation Efficiency

| Position | Mass spec |
| --- | --- |
| 1C1-S239C | 97% |
| 1C1-E258C | 97% |
| 1C1-T289C | 92% |
| 1C1-H435C | 88% |
| 1C1-L443C | 97% |
| 1C1-LC-V205C | 98% |
| 1C1-239ins | 96% |
| R347-S239C | 97% |
| 1C1-WT | 2% |

TABLE 7

EC50 of 1C1-single Cys mutation-ADCs on DU145 cells and Cytotoxicity loss after serum incubation.

| ADC | $EC_{50}$ (ng/ml) | | | $EC_{50}$ loss (fold) | |
| --- | --- | --- | --- | --- | --- |
| | Day 0 | Day 3 | Day 7 | Day 3 | Day 7 |
| 1C1-S239C-ADC | 47.4 | 72.1 | 75.6 | 1.52 | 1.59 |
| 1C1-LC-V205C-ADC | 47.2 | 37.8 | 42.2 | 0.80 | 0.89 |
| 1C1-T289C-ADC | 78.3 | 181.7 | 199.3 | 2.32 | 2.55 |
| 1C1-E258C-ADC | 59 | 48.9 | 53.9 | 0.83 | 0.91 |
| 1C1-H435C-ADC | 70.1 | 75.7 | 95.2 | 1.08 | 1.36 |
| 1C1-239ins-ACD | 60.9 | 84.3 | 91 | 1.38 | 1.49 |
| 1C1-L443C-ADC | 52 | 54 | 51.2 | 1.04 | 0.98 |
| 1C1-ccADC | 8.3 | 15.8 | 24 | 1.90 | 2.89 |

Example 5

Serum Stability of Double Cys Mutation Toxin Conjugates—Cytotoxicity

In certain applications it may be desirable to have more than two drugs per antibody (i.e., a DAR of 4 or more). The Cys mutations described above were tested in various combinations with each other and/or with other mutations, including in some instances the mutations L234F-L235F (designated "FF") to ablate Fc-mediated effector function, and tested for serum stability using the cytotoxicity assay described in Example 6. 1C1-Fc-2Cys mutants and conjugates: 4 drugs/Ab conjugates were tested for serum stability in a cytotoxicity assay: 1C1-239ins-E258C, 1C1-239ins-H435C, 1C1-239ins-S442C, 1C1-FF-E258C-H435C, 1C1-FF-E258C-S442C, and 1C1-FF-H435C-S442C. Also included were 1C1-T289C—2 drugs/Ab comparator and R347-S239C—2 drug/Ab negative control for cytotoxicity assay. All ADC comprise an auristatin based toxin conjugated using maleimide chemistry.

As shown in Table 8, each of the cys mutants has a conjugation efficiency of ~92-100%. The ADCs were incubated with serum for 0, 3 or 7 days and assayed for cytotoxicity as described in Example 6 below. The cytotoxicity curves for each of the combination mutations and controls are plotted in FIGS. 14A, B and C (days 0, 3 and 7, respectively). The $EC_{50}$ values are also provided in the tables below the plots. All the data from this study are summarized in Table 9 and the fold $EC_{50}$ loss at day 3 and 7 are provided.

All 1C1-double Cys mutant ADCs tested were stable after serum incubation. The $EC_{50}$ was retained, especially after 7 days of serum incubation. 1C1-T289C-ADC lost some activity. See TABLE 9.

TABLE 8

1C1-Fc-Cys mutant's Conjugation Efficiency

| Position-conjugate | by Mass spec |
| --- | --- |
| 1C1-239ins-E258C-ADC | ~100% |
| 1C1-239ins-H435C-ADC | ~100% |
| 1C1-239ins-S442C-ADC | ~100% |
| 1C1-FF-E258C-H435C-ADC | ~100% |
| 1C1-FF-E258C-S442C-ADC | ~100% |
| 1C1-FF-H435C-S442C-ADC | ~100% |
| 1C1-T289C-ADC | ~92% |

TABLE 9

EC50 of 1C1-double Cys mutant ADCs on DU145 cells and Cytotoxicity loss after serum incubation.

| ADC | EC50 | | | EC50 loss (fold) | |
|---|---|---|---|---|---|
| | Day 0 | Day 3 | Day 7 | Day 3 | Day 7 |
| 1C1-239ins-E258C-ADC | 25.2 | 32.43 | 25.87 | 1.29 | 1.03 |
| 1C1-239ins-H435C-ADC | 32.79 | 44.75 | 41.84 | 1.36 | 1.28 |
| 1C1-239ins-S442C-ADC | 46.01 | 47.94 | 35.11 | 1.04 | 0.76 |
| 1C1-FF-E258C-H435C-ADC | 34.91 | 43.41 | 41.96 | 1.24 | 1.20 |
| 1C1-FF-E258C-S442C-ADC | 31.7 | 44.21 | 30.66 | 1.39 | 0.97 |
| 1C1-FF-H435C-S442C-ADC | 35.69 | 48.12 | 40.67 | 1.35 | 1.14 |
| 1C1-T289C-ADC | 85 | 402.6 | 243.4 | 4.74 | 2.86 |

Example 6

Materials and Methods

Fc Cysteine Mutation:

The heavy chain of human IgG1 comprising 1C1 antibody was cloned into the pOE-single cassette vector (MedImmune LLC) for convenience of mutagenesis. 187 amino acids on the Fc fragment were mutated to cysteine individually by using the QuikChange II XL Site-Directed Mutagenesis Kit (Agilent Technologies Inc., Santa Clara, Calif.) in 96-well plate format according to manufacturer's instruction. Cysteine mutation in each position was confirmed by sequencing. Similar methodology was used to generate the Cysteine insertion mutations.

High Throughput Small Scale Transfection and Expression:

1C1 kappa chain was cloned into pOE-kappa vector (MedImmune LLC), DNA of 1C1 kappa chain vector and 1C1 heavy chain vector (wild-type or with mutated cysteine) were co-transfected into 293F cells (Life Technologies, Grand Island, N.Y.) in 96-well plates, conditioned medium (CM) containing expressed 1C1 antibody was harvested on day 5 after transfection, antibody concentration in CM was determined by Octet using standard curve made with purified 1C1 WT antibody, expression was also analyzed by protein gel to estimate the aggregation level.

High Throughput Automated Solid Phase Site-Specific Conjugation:

Alexa Fluor 488 C5-maleimide (Life Technologies Grand Island, N.Y.) was used as a surrogate drug cargo to facilitate analysis. High throughput automated conjugation was performed by using PhyNexus Micro-Extractor Automated (MEA) instrument (PhyNexus, Inc., San Jose, Calif.). 1C1 antibody in CM was captured on immobilized protein A in Phynexus Pipet Tips, reduced by Tris (2-carboxyethyl) phosphine (TCEP)(Thermo Scientific, Rockford, Ill.) to remove capped cysteine, oxidized by Dehydroascorbic acid (dhAA) (Sigma-Aldrich Corp., St. Louis, Mo.) to re-form the intra chain disulfide bonds of the antibody, and conjugated with 10 fold molar excess of Alexa Fluor 488 C5-maleimide. The reaction was stopped by N-acetyl-L-cysteine (NAC) (Sigma-Aldrich Corp., St. Louis, Mo.), conjugated antibody was eluted by IgG elution buffer.

Conjugation Efficiency Analysis:

1C1-T289C, which has a conjugation efficiency of higher than 95% by mass spec analysis, was chosen as the conjugation benchmark control. Conjugation efficiency was analyzed by fluorescence SEC, T289C-AF488 was used to make standard curve: different amounts of T289C-AF488 were loaded onto HPLC-SEC with a fluorescence detector (Ex=494, Em=519). The area under the curve (AUC) value at 280 nm (as X axis) and 494 nm (as Y axis) were used to make the standard curve. The standard curve was linear, $R^2$ is very close to 1. 25 ul of 1C1-mutant-AF488 was loaded onto the SEC column, the area values of 280 and 494 of each sample were used to calculate the conjugation efficiency using T289C-AF488 standard curve. The conjugation efficiency was showed as % of T289C conjugation, some mutant's conjugation efficiency was also measured by mass spec, and they correlated well.

Medium Scale Expression and Manual Conjugation:

Manual conjugation was performed to confirm the conjugation efficiency. 1C1-Fc mutants with higher than 50% of the benchmark T289C conjugation level from the automated solid phase conjugation method were expressed in 293F cells in shake flasks and expression level in conditioned medium was measured by protein A HPLC. 1C1-Fc mutants were purified by protein A affinity chromatography and aggregation level was analyzed by SEC. For manual conjugation, 2 mg of 1C1-Fc mutants were reduced in 50 mM of TCEP at 37C for 3 h to uncap engineered cysteines, followed by extensive dialysis in conjugation buffer (PBS+1 mM EDTA, pH7.2) to remove free cysteine, then oxidized in 50 mM of dhAA at room temperature for 4h to re-form the intra chain disulfide bonds. This material was conjugated with 8 fold molar excess of Alexa Fluor 488 C5-maleimide at room temperature for 1 h, the reaction was stopped by N-acetyl-L-cysteine (NAC), free unconjugated AF488 was removed by diluting and concentrating the samples for 3 cycles in spin concentrator, conjugated 1C1-Fc mutants were concentrated to a final volume 0.3-0.5 ml, protein concentration was measured by nano-drop. Conjugation efficiency was measured by fluor SEC and mass spec.

ADC Serum Incubation for Stability Determination:

100 ug of AF488 conjugated 1C1-Fc mutants in 50 ul of PBS (20% of final volume) was mixed with 200 ul of normal human serum or PBS (80% of final volume). After filtering, 10 ul of mixture was loaded to HPLC fluor SEC column to get fluorescence profiles of day 0 control of serum incubation. The rest of each mixture was incubated at 37° C. for 3 days and 7 days. Fluorescence profiles were obtained the same way as 0 day samples. Serum stability was analyzed by dividing the fluorescence peak (area) of antibody-drug conjugate (ADC) by total fluorescence (area) to get percentage of ADC fluorescence for each time point. Fluorescence % remaining in IgG peak at 0 day, 3 days and 7 days was used to estimate the stability. A new fluorescence peak in the human serum albumin (HSA) area was observed for the samples of 3 days or 7 days serum incubation. This peak was calculated to estimate the percentage of conjugates transferred to HSA.

FcRn Binding ELISA:

Half-well ELISA plates were coated with 5 ug/ml of each 1C1 Fc-Cys mutant at 4° C. overnight, washed with PBST, pH5.8, and blocked with fish-gelatin blocking buffer, pH 5.8 at RT for 1 h. 0.02-100 ug/ml of FcRn-biotin (diluted in fish-gelatin blocking buffer, pH 5.8, total 11 dilutions) was added to wells and incubated at room temperature for 2 h. Plates were washed with PBST, pH5.8, and streptavidin-HRP was added and incubated at RT for 40 min, ELISA was developed with TMB and stopped with 0.2N H2SO4. OD450 was measured by EnVision 2104 multilabel reader (PerkinElmer, Waltham, Mass.), EC50 was analyzed by Prism 5 software using a log (agonist) vs. response with variable slope as the model (GraphPad Software, San Diego, Calif.).

Measurement of Equilibrium Binding Constants FcγRs:

The binding constants ($K_D$) for the binding of IgG to hFcγRs were measured on a ProteOn XPR36 instrument. Briefly, the antibodies were immobilized at high density on a GLC sensor chip using a standard amino coupling chemistry as outlined by the instrument manufacturer. The final surface density of IgG measured approximately 3000 RU. A reference flow cell was also prepared on this sensor chip using the identical immobilization protocol minus IgG. Stock solutions of each hFcγR were prepared at either 4000 nM, 16,000 nM, or 32,000 nM in instrument buffer (phosphate buffered saline [PBS]/Tween/Ethylenediaminetetraacetic acid [EDTA] buffer containing 50 mM phosphate, pH 7.4, 0.15 M NaCl, 3 mM EDTA, and 0.005% Tween-20), and then serially diluted (1:3) in the same buffer to obtain the desired concentration series for each receptor: 1.82 nM-4,000 nM (hFcγRI), 197.5 nM-16,000 nM (hFcγRIIA), 395.1 nM-16,000 nM (hFcγRIIb), 21.9 nM-16,000 nM (hFcγRIIIA-158V), and 395-32,000 mM (hFcγRIIIA-158F). Each concentration of FcγR was injected over both the 5T4-108-maia IgG and reference cell surfaces at a flow rate of 25 μL/min for 8 min, during which binding data were collected. Between injections, the surfaces were regenerated (i.e., bound FcγR was removed) with a 60-sec pulse of 5 mM HCl. Several buffer injections were also interspersed throughout the injection series. Later, one of these buffer injections along with the reference cell data was used to correct the binding data for any injection artifacts (e.g., nonspecific binding) through a technique commonly referred to as "double-referencing" (Myszka, 1999). After all binding data were collected, individual data sets were averaged for binding (Response at equilibrium [Req]) at each concentration (C), and then fit to a 1:1 binding isotherm (Req vs. C) plot. From this, the equilibrium binding constants, $K_D$, were derived using the vendor's evaluation software, version 3.1.0.6.

Measurement of Equilibrium Binding Constants Human FcRn Protein;

The affinity ($K_D$) for the binding of IgG to human FcRn protein (huFcRn) was measured on a ProteOn XPR36 instrument. Briefly, the antibodies were immobilized at high density on a GLC sensor chip using a standard amino coupling chemistry, as described above. A stock solutions of huFcRn protein was prepared at 3000 nM in instrument buffer (50 mM sodium phosphate buffer, pH 6, containing 150 mM NaCl, and 0.05% Tween-20), and then serially diluted (3:1) to 1.37 nM in the same buffer. Each concentration of FcRn was sequentially injected over the 5T4-108-maia IgG and reference cell surfaces, connected in series, at a flow rate of 25 μL/min for 16 min. Binding data were collected, followed by a 60-sec injection of 50 mM sodium phosphate buffer, pH 7.4, containing 150 mM NaCl, and 0.05% Tween 20 between injections of each receptor or buffer blank to regenerate the IgG surface (i.e., remove bound FcRn protein). Several buffer injections were also interspersed throughout the injection series. Later, one of these buffer injections was used along with the reference cell data to correct the raw data sets for injection artifacts (e.g., nonspecific binding) through "double-referencing" (Myszka, 1999). After all binding data was collected, individual data sets were averaged for binding (Req) at each concentration (C), and then fit to a 1:1 binding isotherm (Req vs. C) plot. From this, the equilibrium binding constants, $K_D$, were derived using the vendor's BIAevaluation software, v. 4.1.

Thermal Stability Measurement:

The thermal unfolding profiles of 1C1 Fc-Cys mutants were measured by differential scanning calorimetry (VP-DSC, MicroCal, LLC, Northampton, Mass.), 0.503 ml of 1C1 Fc-Cys mutant at 1mg/ml concentration in 25 mM histidine buffer, pH6.0 was loaded into chamber, scanned at 1° C./min from 20° C. to 110° C. Transition mid-points ($T_m$ values) from the thermogram data were determined using the non-two-state model within the Origin 7 software provided by the manufacturer.

Conjugation with Toxin:

2 mg of each 1C1 Fc-Cys mutant and benchmark control mutant was conjugated manually with toxin 1 or toxin 2 using the same method as conjugation to AF488 described above. Free drug was removed by CHT type II (Ceramic Hydroxyapatite) liquid chromatography, eluted with 0-2M NaCl gradient in 10 mM phosphate buffer, pH 7.0. The monomeric ADC peak was collected and dialyzed in 25 mM histidine, pH 6.0 plus 7% sucrose, and concentrated to 0.3 to 0.5 ml. Conjugation efficiency was analyzed by mass spectrometry.

Cytotoxicity Assay to Determine the Serum Stability of ADC:

ADC serum incubation was set up the same way as described above. DU-145 cells were plated into white-walled 96-well plates (VWR, Radnor, Pa.): 2000 cells in 80 ul/well, and grown overnight in 37° C., 5% CO2 incubator. ADC-serum samples were diluted to 0.004-80 ug/ml with culture medium, 20 ul of diluted ADC—serum was added into 80 ul of cells, in triplicate. The final concentrations of ADC in the culture were 0.0008 to 16 ug/ml, cells were incubated at incubator for another 3 days, and viable cells were determined by using CellTiter-Glo Luminesecent Cell Viability Assay kit (Promega, Madison, Wis.). Luminescence signal was measured by EnVision 2104 multilabel reader (PerkinElmer, Waltham, Mass.) and EC50 of cell killing was analyzed by Prism 5 software using a log (agonist) vs. response with variable slope as the model (GraphPad Software, San Diego, Calif.).

The embodiments provided herein have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments are sufficient to allow others, applying knowledge within the skill of the art, to readily modify and/or adapt for various applications such specific embodiments, without undue experimentation, without departing from the general concepts presented herein. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of this disclosure should not be limited by any of the above-described exemplary embodiments, but should be defined only in accordance with the following claims and their equivalents.

What is claimed is:

1. A conjugate compound comprising a cysteine-engineered antibody or Fc fusion protein and at least one heterologous moiety, wherein:
   (i) the Fc domain of the antibody or Fc fusion protein comprises a cysteine amino acid insertion between positions 239 and 240, wherein the amino acid position numbering is according to the EU index as set forth in Kabat; and
   (ii) wherein at least one heterologous moiety is conjugated to the cysteine amino acid insertion between positions 239 and 240.

2. The conjugate compound according to claim 1, further comprising:
   (a) a Cysteine (C) substituting the Glutamic acid (E) located at position 258;
   (b) a Cysteine (C) substituting the Histidine (H) located at position 435;
   (c) a Cysteine (C) substituting the Arginine (R) located at position 435; or
   (d) a combination thereof,
   wherein the amino acid position numbering is according to the EU index as set forth in Kabat.

3. The conjugate compound according to claim 1, wherein the Fc domain further comprises at least one engineered cysteine amino acid selected from cysteine amino acid substitutions at amino acid positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446.

4. The conjugate compound according to claim 1, wherein each one of the heterologous moieties is conjugated to an engineered cysteine.

5. The conjugate compound according to claim 1, wherein the Fc domain of the antibody or Fc fusion protein is a human IgG Fc domain.

6. The conjugate compound according to claim 5, wherein the human IgG is an IgG1, IgG2, IgG3, or IgG4.

7. The conjugate compound according to claim 1, wherein the Fc fusion protein comprises an antigen binding domain selected from the group consisting of: (a) an scFv; (b) a diabody; (c) an Fd fragment; (d) an Fv fragment; (e) a F(ab')$_2$ fragment; and (f) a F(ab) fragment.

8. The conjugate compound according to claim 1, wherein the antibody is a monoclonal antibody, a bispecific antibody, a multispecific antibody, a chimeric antibody, a human antibody, or a humanized antibody.

9. The conjugate compound according to claim 1, wherein at least one heterologous moiety is a toxin, drug, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, non-natural amino acid, peptide, lipid, carbohydrate, scaffolding molecule, fluorescent tag, visualization peptide, biotin, serum half-life extender, capture tag, chelating agent, solid support, or a combination thereof, and wherein conjugation is at one of the engineered cysteines.

10. The conjugate compound according to claim 9, wherein the drug is an auristatin, a tubulysin, a pyrrolobenzodiazepine (PBD), or a maytansinoid.

11. The conjugate compound according to claim 1, wherein the cysteine-engineered antibody or Fc fusion protein specifically binds to at least one target.

12. The conjugate compound according to claim 11, wherein the target is a tumor antigen and the heterologous moiety is an antitumor agent.

13. The conjugate compound of claim 1, further comprising one or more engineered cysteine amino acids selected from cysteine amino acid substitutions at amino acid positions 241, 243, 251, 253, 258, 264, 269, 271, 272, 274, 280, 281, 285, 288, 291, 293, 294, 296, 301, 307, 309, 311, 318, 329, 340, 341, 345, 357, 385, 386, 387, 401, 402, 411, 417, 433, 435, or 439, wherein the amino acid position numbering is according to the EU index as set forth in Kabat.

14. The conjugate compound of claim 13, wherein the engineered cysteine amino acid is selected from cysteine amino acid substitutions at amino acid positions 241, 243, 251, 253, 258, 264, 271, 285, 288, 291, 296, 301, 307, 309, 311, 329, 385, 387, 433, or 435, and combinations thereof.

15. The conjugate compound of claim 14, wherein the engineered cysteine amino acid is selected from cysteine amino acid substitutions at amino acid positions 258 or 435, and combinations thereof.

* * * * *

UNITED STATES PATENT AND TRADEMARK OFFICE
CERTIFICATE OF CORRECTION

PATENT NO. : 10,744,204 B2
APPLICATION NO. : 15/302036
DATED : August 18, 2020
INVENTOR(S) : Gao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this
Twentieth Day of December, 2022

*Katherine Kelly Vidal*

Katherine Kelly Vidal
*Director of the United States Patent and Trademark Office*